(12) United States Patent
Kim

(10) Patent No.: US 9,333,250 B2
(45) Date of Patent: May 10, 2016

(54) METHODS AND COMPOSITIONS FOR TREATING BACTERIAL INFECTION

(75) Inventor: Kwang S. Kim, Reistertown, MD (US)

(73) Assignee: The Johns Hopkins University, Baltimore, MD (US)

( * ) Notice: Subject to any disclaimer, the term of this patent is extended or adjusted under 35 U.S.C. 154(b) by 1750 days.

(21) Appl. No.: 12/226,088

(22) PCT Filed: Apr. 6, 2007

(86) PCT No.: PCT/US2007/008732
§ 371 (c)(1),
(2), (4) Date: Aug. 4, 2009

(87) PCT Pub. No.: WO2007/117680
PCT Pub. Date: Oct. 18, 2007

(65) Prior Publication Data
US 2010/0136027 A1    Jun. 3, 2010

Related U.S. Application Data

(60) Provisional application No. 60/789,791, filed on Apr. 6, 2006.

(51) Int. Cl.
*A61K 39/108* (2006.01)
*C07K 14/245* (2006.01)
*G01N 33/53* (2006.01)
*A61K 39/00* (2006.01)

(52) U.S. Cl.
CPC ............ *A61K 39/0258* (2013.01); *C07K 14/245* (2013.01); *G01N 33/5308* (2013.01); *A61K 2039/505* (2013.01); *A61K 2039/53* (2013.01)

(58) Field of Classification Search
None
See application file for complete search history.

(56) References Cited

U.S. PATENT DOCUMENTS

2010/0136027 A1* 6/2010 Kim .......................... 424/164.1

FOREIGN PATENT DOCUMENTS

WO    WO 2007/117680 A2 * 10/2007

OTHER PUBLICATIONS

Bonacorsi et al, The Journal of Infectious Diseases, Jun. 15, 2003; 187:1895-906.*
Schneider et al, Infection and Immunity, Oct. 2004, p. 5993-6001 vol. 72, No. 10.*
Yao et al, Infection and Immunity, Apr. 2006, p. 2196-2206 vol. 74, No. 4.*
Hentschel et al, Microbes and Infection, 3, 2001, 545-548.*
Bonacorsi et al, Medecine et Maladies Infectieuses, (Apr. 2000) vol. 30, No. 4, pp. 217-224 (abstract only).*
Bloch et al, FEMS microbiology Letters, 1996, 144:171-176.*
Houdouin et al, Infection and Immunity, Oct. 2002, p. 5865-5869 vol. 70, No. 10.*
Lloyd et al, Journal of Bacteriology, Jun. 2009, p. 3469-3481 vol. 191, No. 11.*
Xie et al, The Journal of Infectious Diseases 2006; 194:358-64.*
Elliott et al, Abstracts of the General Meeting of the American Society for Microbiology, (2002) vol. 102, pp. 54. print. Meeting Info.: 102nd General Meeting of the American Society for Microbiology. Salt Lake City, UT, USA. May 19-23, 2002. American Society for Microbiology (abstract only).*
Bingen-Bidois, Martine et al., "Phylogenetic Analysis and Prevalence of Urosepsis Strains of *Escherichia coli* Bearing Pathogenicity Island-Like Domains," Infection and Immunity, vol. 70(6):3216-3226 (2002).
International Search Report for Application No. PCT/US07/08732, 3 pages, dated Oct. 7, 2008.

* cited by examiner

*Primary Examiner* — Nita M Minnifield
(74) *Attorney, Agent, or Firm* — Mintz Levin Cohn Ferris Glovsky and Popeo, P.C.; Peter F. Corless; Christopher R. Cowles

(57) ABSTRACT

The present invention relates to methods and compositions for the treatment of bacterial infection, for example extraintestinal *E. coli* infection such as *E. coli* bacteremia, meningitis and sepsis. The invention relates also to methods of diagnosis and prevention.

7 Claims, 12 Drawing Sheets

METHODS AND COMPOSITIONS FOR TREATING BACTERIAL INFECTION

RELATED APPLICATIONS

This application claims the benefit of U.S. Provisional Application No. 60/789,791, filed on Apr. 6, 2006. The entire content of the aforementioned application is hereby incorporated herein by reference.

STATEMENT OF RIGHTS TO INVENTIONS MADE UNDER FEDERALLY SPONSORED RESEARCH

This work may be supported by grants from the National Institutes of Health. The government may have certain rights in the invention.

FIELD OF THE INVENTION

The present invention relates to methods and compositions for the treatment of bacterial infection, for example extraintestinal *E. coli* infection such as *E. coli* bacteremia, meningitis and sepsis. The invention relates also to methods of diagnosis and prevention.

BACKGROUND OF THE INVENTION

*Escherichia coli* is the most common gram-negative organism causing nosocomial bacteremia in infants, children and adults. *E. coli* is also the most common cause of gram-negative bacteremia in patients with cancer and leukemia as well as in veterans and elderly patients. The mortality and morbidity associated with *E. coli* bacteremia is substantial. For example, *E. coli* sepsis is associated with estimated 40,000 deaths each year at a cost of 2.0 billion dollars per annum in the US (67). A recent report has also shown that community-acquired bacteremia is responsible for at least one third of deaths in infants and children in sub-Saharan Africa, and *E. coli* was the most common cause for bacteremia in infants (68).

At present, there are no preventive measures available against *E. coli* bacteremia. A major contributing factor is an incomplete understanding of the pathogenesis of *E. coli* bacteremia, e.g., what are the microbial determinants contributing to *E. coli* bacteremia. Previous studies have identified several microbial factors associated with the pathogenesis of *E. coli* bacteremia. For example, the K1 capsular polysaccharide and O-lipopolysaccharide (LPS) have previously been shown to be critical for induction of *E. coli* bacteremia. However, the feasibility of using the K1 capsule and O-LPS for the prevention of *E. coli* bacteremia, has not been realized, and where attempted has been shown to be limited.

Thus, there remains a need in the art for the identification of microbial targets for the prevention of bacterial infections, and in particular *E. coli* extraintestinal infections.

SUMMARY OF THE INVENTION

The instant invention provides methods and compositions for the treatment of extraintestinal *E. coli* infection, including bacteremia and meningitis. The invention has a number of aspects and embodiments which will be described below.

In one aspect, the invention provides a method for immunizing a subject against a bacterial infection, the method comprising administering to the subject a polypeptide or nucleic acid encoding an *Escherichia coli* (*E. coli*)-derived island (RDI) or fragment thereof, thereby immunizing the subject.

In another aspect, the invention provides a method of treating or preventing a bacterial infection in a subject, the method comprising administering to the subject a composition comprising a molecule that targets an *Escherichia coli* (*E. coli*-derived island (RDI) or fragment thereof, thereby treating or preventing a bacterial infection in a subject.

In one embodiment, the molecule is an antibody.

In another embodiment, the method stabilizes, reduces the symptoms of, or ameliorates a disease or disorder characterized by a bacterial infection.

In still another embodiment, the *E. coli*-derived island is selected from the group consisting of: RD218, C5, 1HE3034, RS167, A90, S88, S95, and MG1655 *E. coli* derived islands.

In one particular aspect, the invention features a method for diagnosing a bacterial infection, the method comprising determining the level of expression of an RDI nucleic acid molecule, polypeptide or fragment thereof in a subject sample, wherein an increased level of expression relative to a reference, indicates that the subject has or has a propensity to develop extraintestinal *E. coli* infection.

In a particular embodiment of any one of the above aspects, the bacterial infection is an *E. coli* infection. In a further embodiment, the *E. coli* infection is an extraintestinal *E. coli* infection. In yet a further embodiment, the extraintestinal *E. coli* infection is selected from the group consisting of: bacteremia, sepsis, meningitis, urinary tract infection, and pneumonia.

In another aspect, the invention features a method for identifying microbial determinants involved in a bacterial infection, the method comprising systematic genome comparison.

In another particular aspect, the invention features a method for identifying microbial determinants involved in a bacterial infection, the method comprising in silico gene comparison.

In one embodiment of the above aspects, the in silico method comprises microarray gene comparison or systematic genome comparison.

In another embodiment of any one of the above aspects, the bacterial infection is an *E. coli* infection. In a further embodiment, the *E. coli* infection is an extraintestinal *E. coli* infection. In yet a further embodiment, the extraintestinal *E. coli* infection is selected from the group consisting of: bacteremia, sepsis, meningitis, urinary tract infection, and pneumonia.

In another particular aspect, the invention features a vector comprising an *E. coli* RDI nucleic acid molecule, or fragment thereof, encoding a polypeptide selected from the group of RDIs 1, 4, 7, 12, 13, 16, 20, 21, and 22.

In one embodiment, the vector is a cloning or expression vector. In another embodiment, the vector is a viral vector. In a further embodiment, the vector comprises a second polynucleotide sequence encoding an antigenic polypeptide of interest.

In another embodiment, a host cell comprises the vector as described in the above-mentioned aspects and embodiments. In another particular embodiment, the cell expresses one or more *E. coli* RDIs or fragments thereof. In one embodiment, the cell is in vitro. In another embodiment, the cell is in vivo. In a further embodiment, the cell is a mammalian cell. In still a further embodiment, the cell is a human cell.

In another aspect, the invention features an antibody reactive with an *E. coli*-derived (RDI) polypeptide or protein or portion thereof.

In one embodiment, the antibody is monoclonal. In another embodiment, the antibody is polyclonal. In another particular embodiment, the *E. coli*-derived (RDI) polypeptide or protein is selected from RDIs 1, 4, 7, 12, 13, 16, 20, 21, and 22.

In another aspect, the invention features a pharmaceutical composition comprising a molecule that binds or interacts with an *E. coli* RDI or fragment thereof, in a pharmaceutically acceptable excipient, wherein the *E. coli* RDI or fragment thereof is capable of modulating an immune response in a subject.

In one embodiment, the molecule is an antibody. In another embodiment, the *E. coli* RDI or fragment thereof is selected from RDIs 1, 4, 7, 12, 13, 16, 20, 21, and 22. In another particular embodiment, the *E. coli* RDI or fragment thereof comprises at least one open reading frame or a fragment thereof.

In a particular embodiment, the pharmaceutical composition comprises an effective amount of the vector of any of the aspects as described herein, in a pharmaceutically acceptable excipient.

In another aspect, the invention features an immunogenic composition comprising an *E. coli* RDI or fragments thereof in a pharmaceutically acceptable excipient.

In one embodiment, the *E. coli* RDI or fragments thereof are selected from polypeptides, nucleic acids, and vectors. In another embodiment, the immunogenic composition of the aspect further comprises an antigen of interest. In another particular embodiment, the *E. coli* RDI or fragment thereof enhances an immune response against the antigen of interest. In another further embodiment, the antigen of interest is at least a fragment of a polypeptide expressed by a pathogen.

In another embodiment, the pathogen is a bacterium. In a further embodiment, the bacterium is a gram-negative bacterium. In another further embodiment, the gram-negative bacterium is *E. coli*.

In another aspect, the invention features a method of modulating an immune response in a subject in need thereof, the method comprising administering to the subject an *E. coli* RDI or fragment thereof capable of modulating an immune response or a polynucleotide encoding the fragment.

In another aspect, the invention features a method of enhancing an immune response in a subject against an immunogenic composition, the method comprising administering an effective amount of a pharmaceutical composition comprising one or more *E. coli* RDIs or fragments thereof as described in the above-mentioned aspects, or polynucleotides encoding the fragments to a subject before, during, or after the administration of an immunogenic composition as described in the above-mentioned aspects, such that the subjects immune response is enhanced.

In one embodiment, the immune response is an adaptive immune response.

In another embodiment of the above aspect, the method enhances an immune response against a bacterial infection.

In a further embodiment, the bacterial infection is an *E. coli* infection. In another embodiment, the *E. coli* infection is an extraintestinal *E. coli* infection. In still another embodiment, the extraintestinal *E. coli* infection is selected from the group consisting of: bacteremia, sepsis, meningitis, urinary tract infection, and pneumonia.

In another aspect, the invention features a kit for immunizing a subject against a bacterial infection, the kit comprising a pharmaceutical composition according to the above-mentioned aspects and instructions for use.

In another aspect, the invention features a kit for immunizing a subject against a bacterial infection, the kit comprising an immunogenic composition according to the above-mentioned aspects, and instructions for use.

In still another aspect, the invention features a kit for treating or preventing a bacterial infection in a subject, the kit comprising a pharmaceutical composition according to the above-mentioned aspects, and instructions for use.

In a further aspect, the invention features a kit for treating or preventing a bacterial infection in a subject, the kit comprising an immunogenic composition according to the above-mentioned aspects, and instructions for use.

In another embodiment, the invention features a diagnostic kit for the diagnosis of a bacterial infection, the kit comprising an immunogenic composition according to the above-mentioned aspects, and instructions for use.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

The terms "administration" or "administering" are defined to include an act of providing a compound or pharmaceutical composition of the invention to a subject in need of treatment.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine, phosphothreonine. Amino acids are well known in the art. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

By "antibody" is meant any immunoglobulin, including antibodies and fragments thereof, that binds a specific epitope. The term encompasses polyclonal, monoclonal, and chimeric antibodies (e.g., bispecific antibodies). An "antibody combining site" is that structural portion of an antibody molecule comprised of heavy and light chain variable and hypervariable regions that specifically binds antigen. Exemplary antibody molecules are intact immunoglobulin molecules, substantially intact immunoglobulin molecules, and those portions of an immunoglobulin molecule that contains the paratope, including Fab, Fab', F(ab')$_2$ and F(v) portions, which portions are preferred for use in the therapeutic methods described herein.

By "bacterial infection" is meant to refer to any disease or condition that is caused by bacteria. In preferred embodiments, bacterial infection is caused by any gram-negative bacteria. An exemplary gram negative bacterium according to methods of the invention is *E. coli*. Exemplary bacterial infections include extraintestinal *E. coli* infections, for example bacteremia, sepsis, meningitis, urinary tract infection, and pneumonia.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

By an "effective amount" is meant an amount sufficient to affect beneficial or desired results, e.g., such as an effective amount of nucleic acid transfer and/or expression, and/or the attainment of a desired therapeutic endpoint. An effective amount can be administered in one or more administrations, applications or dosages. In one aspect, an effective amount of a nucleic acid delivery vector is an amount sufficient to transform/transduce/transfect at least one cell in a population of cells comprising at least two cells.

By "therapeutically effective amount" is meant an amount sufficient to prevent, correct and/or normalize an abnormal physiological response. In exemplary embodiments, a "therapeutically effective amount" is an amount sufficient to reduce by at least about 30 percent, more preferably by at least 50 percent, most preferably by at least 90 percent, a clinically significant feature of pathology, for example a feature or features of a bacterial infection.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers.

By "extraintestinal" is meant outside of the intestinal region. In preferred embodiments, the bacteria are extraintestinal bacteria.

By "fragment" is meant a portion (e.g., at least 10, 25, 50, 100, 125, 150, 200, 250, 300, 350, 400, or 500 amino acids or nucleic acids) of a protein or nucleic acid molecule that is substantially identical to a reference protein or nucleic acid and retains the biological activity of the reference. In some embodiments the portion retains at least 50%, 75%, or 80%, or more preferably 90%, 95%, or even 99% of the biological activity of the reference protein or nucleic acid described herein.

By "host cell" is meant any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

By "in silico" is meant to refer to experiments performed on computer or via computer simulation.

By "immunizing" or "immunize" is meant to include the process by which an individual is exposed to an agent that is designed to fortify his or her immune system against that agent. Vaccination is a form of immunization.

By "immune response" is meant the process whereby inflammatory cells are recruited from the blood to lymphoid as well as non-lymphoid tissues via a multifactorial process that involves distinct adhesive and activation steps. Inflammatory conditions cause the release of chemokines and other factors that, by upregulating and activating adhesion molecules on inflammatory cells, promote adhesion, morphological changes, and extravasation concurrent with chemotaxis through the tissues. "Adaptive immunity" refers to antigen-specific immune response.

By "isolated," "purified," or "biologically pure" is meant material that is free to varying degrees from components which normally accompany it as found in its native state. Various levels of purity may be applied as needed according to this invention in the different methodologies set forth herein; the customary purity standards known in the art may be used if no standard is otherwise specified.

By "microarray" is meant a collection of nucleic acid molecules or polypeptides from one or more organisms arranged on a solid support (for example, a chip, plate, or bead).

By "*E. coli* derived island (RDI)" is meant to include any genomic island, a genomic island including a set of genes, from a gram-negative bacteria. A gram-negative bacterial cell is intended to include the art recognized definition of this term. Typically, Gram-negative bacteria include *Gluconobacter, Rhizobium, Bradyrhizobium, Alcaligenes, Rhodobacter, Rhodococcus, Azospirillum, Rhodospirillum, Sphingomonas, Burkholderia, Desulfomonas, Geospirillum, Succinomonas, Aeromonas, Shewanella, Halochromatium, Citrobacter, Escherichia, Klebsiella, Zymomonas* (e.g., *Zymomonas mobilis*), *Zymobacter* (e.g., *Zymobacter palmae*), and *Acetobacter* (e.g., *Acetobacter pasteurianus*). In certain embodiments, RDIs are derived from *E. coli*, and can include *Escherichia coli* (*E. coli*)-derived islands (RDIs) or fragments thereof. In preferred embodiments, microbial determinants are RDIs selected from RDI 1, 4, 7, 12, 13, 16, 20, 21, and 22.

By "nucleic acid" is meant an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly.

By "pharmaceutically acceptable carrier" is meant to encompass any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin *Remington's Pharm. Sci.*, 15th Ed. (Mack Publ. Co., Easton (1975)).

By "protein" is meant any chain of amino acids, or analogs thereof, regardless of length or post-translational modification.

By "reference" is meant a standard or control condition.

By "specifically binds" is meant a molecule (e.g., peptide, polynucleotide, antibody) that recognizes and binds a protein or nucleic acid molecule, or fragment thereof, of the invention, but which does not substantially recognize and bind other molecules in a sample, for example, a biological sample, which naturally includes a protein of the invention.

By "subject" is meant a vertebrate, preferably a mammal, more preferably a human. Mammals include, but are not limited to, murines, simians, humans, farm animals, sport animals, and pets.

By "viral vector" is meant a virus or viral particle that comprises a polynucleotide to be delivered into a host cell, either in vivo, ex vivo or in vitro. Examples of viral vectors include, but are not limited to, adenovirus vectors, adeno-associated virus vectors, retroviral vectors, and the like. In aspects where gene transfer is mediated by an adenoviral vector, a vector construct refers to the polynucleotide comprising the adenovirus genome or part thereof, and a selected, non-adenoviral gene, in association with adenoviral capsid proteins.

BRIEF DESCRIPTION OF THE DRAWINGS

FIG. 4A: ibeA; FIG. 4B: cnfl; FIG. 4C: iha; FIG. 4D: fuA; FIG. 4E: hlyE and hlyA; FIG. 4F: iucA.

DETAILED DESCRIPTION OF THE INVENTION

Figure 1:
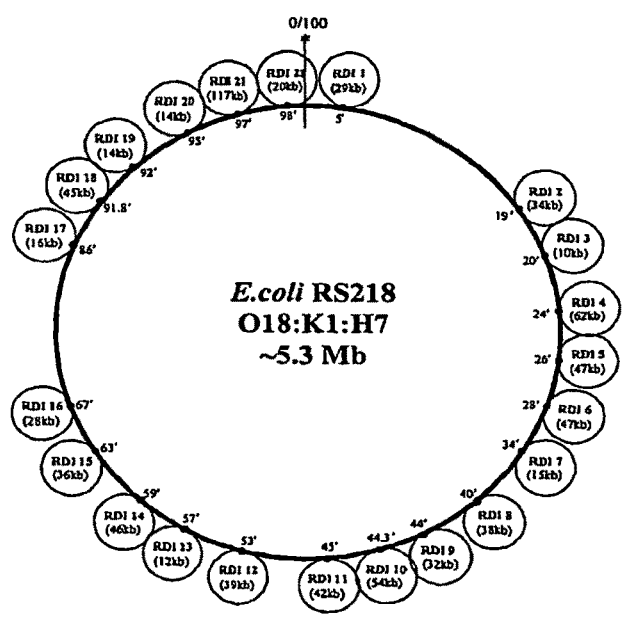
FIG. 1 is a schematic showing a genomic map of E. coli RS 218-derived islands (RDIs).

In general, the invention features methods and compositions for the treatment of bacterial infection, for example extraintestinal E. coli infection such as E. coli bacteremia, meningitis and sepsis. The invention relates also to methods of diagnosis and prevention. The invention is based in part on the finding that the K1 capsule polysaccharide and O-LPS are shown to be important in induction of E. coli bacteremia. Thus, identifying potential microbial targets, including bacterial RDIs, for example E. coli RDIs, will help in identifying potential microbial targets to treat and prevent the aforementioned bacterial infections.

E. Coli and Extraintestinal Infection

Extraintestinal pathogenic Escherichia coli (ExPEC) possess virulence traits that allow them to invade, colonize, and induce disease in bodily sites outside of the gastrointestinal tract. As an extraintestinal pathogen, Escherichia coli is best known for causing urinary tract infection (UTI), bacteremia, and neonatal bacterial meningitis (NBM). However, E. coli can also infect almost any anatomical site, and can cause pathologies including pneumonia, deep surgical wound infection, and vertebral osteomyelitis with associated epidural/psoas/iliacus abscesses (60). E. coli is the most common gram-negative organism causing nosocomial bacteremia in infants, children and adults. For example, the SCOPE (Surveillance and Control of Pathogens of Epidemiological Importance) project focused on nosocomial bloodstream infections in the U.S., and revealed that E. coli is the most common cause of gram-negative bloodstream infections (78). The SENTRY Antimicrobial Surveillance Program from three regions of the world (North and Latin America and Europe) from 1997 to 2002 also revealed that E. coli is the most frequently isolated gram-negative organism from patients with bloodstream infections (79). A population-based assessment revealed that E. coli is the most common community-onset bacteremia in seniors (84). A recent report has also shown that community-acquired bacteremia is responsible for at least one third of deaths in infants and children in sub-Saharan Africa and E. coli was the most common cause for bacteremia in infants (86). The mortality and morbidity associated with E. coli bacteremia is substantial. For example, E. coli sepsis is associated with estimated 40,000 deaths each year at a cost of 2.0 billion dollars per annum in the US (85). At present, there are no measures available to prevent E. coli bacteremia.

A major contributing factor to high morality associated with E. coli bacteremia is the incomplete understanding of microbial determinants contributing to E. coli bacteremia. The K1 capsule polysaccharide and O-LPS are shown to be important in induction of E. coli bacteremia (87, 88), but the feasibility of using the K1 capsule and O-LPS for the prevention of E. coli bacteremia has been shown to be limited (89-91). For example, the K1 antigen is immunologically poor and its antibody has been shown to cross react with host structures. Further, there are many different serotypes of O-LPS associated with E. coli bacteremia and functional activity of O-LPS antibody is serotype-specific.

Genome sequencing of E. coli should provide comprehensive information on microbial determinants involved in bacteremia. In the examples provided herein, E. coli K1 determinants contributing to bacteremia are identified using two complimentary functional genomic approaches. The first approach utilizes systematic genome comparison between clinical E. coli K1 strain RS 218 and non-pathogenic laboratory strain E. coli MG1655. The second approach utilizes E. coli microarray to examine and compare expression profiling during experimental E. coli bacteremia. The functional genomic approaches described herein are useful for any gram negative bacterial strain where a pathogenic strain (for example, a clinically identified strain of gram negative bacteria) can be examined and compared to a non-pathogenic laboratory strain using systematic genome comparison or microarray expression profiling.

E. Coli and Pathogenesis

E. coli is a gram-negative, rod-shaped bacterium about 2.5 micrometers long that contains flagella, and a genome of 4,639,221 base pairs encoding at least 4000 genes. The K-12 strain was first isolated in 1921 from the stool of a malaria patient and it has been maintained in laboratory stocks as a pure strain for the last 75 years. E. coli K-12 was the bacterial strain of choice in biochemistry labs because it was easy to grow and amenable to metabolic studies. Like all gram-negative bacteria, E. coli have no nuclear membrane and the chromosome is a large circular duplex molecule with a membrane attachment site and a single origin of replication. E. coli cells can support the replication of DNA plasmids, many of which encode antibiotic-resistance genes.

E. coli K1 strain RS218 is a prototype strain for neonatal meningitis and has a larger genomic size compared to the laboratory K-12 strain MG1655 (89, 90). The K1 antigen is considered the major determinant of virulence among strains of E. coli that cause neonatal meningitis. K1 is a homopolymer of sialic acid, and it inhibits phagocytosis, complement, and responses from the host's immunological mechanisms.

It is well known that virulence factors are usually clustered together in the bacterial chromosome and form so-called "genomic islands" (8). Besides pathogenic factors, genomic islands may also contain genes that contribute to general adaptability, fitness, and competitiveness of the bacteria in a specific niche (9,10). Genomic islands of pathogenic *E. coli* are comprised of large genomic regions and can be distinguished through genome sequence comparison of pathogenic strain(s) with non-pathogenic strain(s) (11).

*E. coli* is the most common gram negative bacteria causing neonatal meningitis (89, 90). *E. coli* K1 meningitis is a serious infectious disease associated with high mortality and morbidity (1,2). Neonatal meningitis affects 1/2,000-4,000 infants. Eighty percent of *E. coli* strains involved synthesize K-1 capsular antigens (K-1 is only present 20-40% of the time in intestinal isolates).

The development of *E. coli* K1 meningitis is considered a complex and multistage process (3). Initial stages of disease include mucosal colonization by the pathogen, and microbial invasion into the intravascular space, followed by intravascular survival and multiplication. On the next stage, after reaching a high degree of bacteremia bacteria penetrate the blood-brain barrier (BBB) and invade the central nervous system (CNS) (4,5). Bacterial invasion into the CNS subsequently results in inflammation and intracranial complications such as pleocytosis, BBB disruption and neuronal injury (3,6,7).

Polypeptides

In general, polypeptides of the invention may be produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, 10801 University Boulevard, Manassas, Va. 20110-2209). The method of transformation or transfection and the choice of expression vehicle will depend on the host system selected. Transformation and transfection methods are well known in the art, and are described in standard laboratory manuals, such as Current Protocols in Molecular Biology, Ausubel F et al. Expression vehicles may be chosen from those provided, e.g., in Cloning Vectors: A Laboratory Manual (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

One particular bacterial expression system for polypeptide production is the *E. coli* pET expression system (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Once the recombinant polypeptide of the invention is expressed, it is isolated, e.g., using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., Current Protocols in Molecular Biology).

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980). Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.). These general techniques of polypeptide expression and purification can also be used to produce and isolate useful peptide fragments.

Polynucleotides

In general, the invention includes any nucleic acid sequence encoding a RDI or fragment thereof, where the RDI or fragment is useful for treating or preventing a bacterial infection, for example, but not limited to, an extraintestinal *E. coli* infection. An isolated nucleic acid molecule is readily manipulatable by recombinant DNA techniques well known in the art. Thus, a nucleotide sequence contained in a vector in which 5' and 3' restriction sites are known, or for which polymerase chain reaction (PCR) primer sequences have been disclosed, is considered isolated, but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, as the term is used herein, because it is readily manipulatable by standard techniques known to those of ordinary skill in the art.

Modulation of an Immune Response Using a RDI Polynucleotide

Polynucleotide therapy featuring a polynucleotide encoding a RDI or fragment thereof is another therapeutic approach for treating a bacterial infection, for example an *E. coli* infection, or preventing or ameliorating a bacterial infection, for example an *E. coli* infection. Such nucleic acid molecules can be delivered to cells of a subject in need of treatment, e.g. a subject suffering from or at risk for a bacterial infection, for example an *E. coli* infection. The nucleic acid molecules must be delivered to the cells of a subject in a form in which they can be taken up so that therapeutically effective levels of a RDI or fragment thereof can be produced.

A vector, for example a cloning or expression vector, can be employed for the introduction of therapeutic to a cell of a patient requiring modulation of an immune response. In certain embodiments, a vector comprising an *E. coli* RDI nucleic acid molecule, or fragment thereof, of a polypeptide selected from the group including, but not limited to: RDIs 1, 4, 7, 12, 13, 16, 20, 21, and 22 can be used. A nucleic acid molecule can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al, Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types epithelial cells, dendritic cell, and monocyte macrophages can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding a RDI or a fragment thereof; can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77 S-83S, 1995). Retroviral vectors are particularly well developed and have been used in clinical settings (Rosenberg et al., N. Engl. J. Med 323:370, 1990; Anderson et al., U.S. Pat. No. 5,399,346). Most preferably, a viral vector is used to administer a RDI polynucleotide systemically.

Methods of Treatment and Prevention

Included in the invention are methods for treating and preventing a bacterial infection. Presently, treatment and prevention methods for bacterial infection such as extraintestinal *E. coli* infection including bacteremia, sepsis, meningitis, urinary tract infection, and pneumonia are limited. Accordingly, identifying potential microbial targets, including RDIs, for example *E. coli* RDIs, will help in identifying potential microbial targets to treat and prevent the aforementioned bacterial infections.

Therapy may be provided wherever anti-bacterial therapy is performed: at home, the doctor's office, a clinic, a hospital's outpatient department, or a hospital. Treatment may generally begin at a hospital or healthcare provider so that the doctor can observe the therapy's effects closely and make any adjustments that are needed. The duration of the therapy depends on the kind of bacterial infection being treated, the age and condition of the patient, the stage and type of the patient's disease, and how the patient's body responds to the treatment. Drug administration may be performed at different intervals (e.g., daily, weekly, or monthly). Therapy may be given in on-and-off cycles that include rest periods so that the patient's body has a chance to regain its strength.

Depending on the type of bacterial infection and its stage or progression, the therapy can be used for treatment or prevention. As described above, if desired, treatment with an immunogenic or pharmaceutical composition of the invention may be combined with therapies for the treatment of a bacterial infection (e.g. an *E. coli* infection, such as an extraintestinal *E. coli* infection, for instance meningitis, UTI, sepsis, pneumonia).

After a subject is diagnosed as having a bacterial infection (e.g., an *E. coli* infection, such as an extraintestinal *E. coli* infection, for instance meningitis, UTI, sepsis, pneumonia) method of treatment is selected. A number of standard treatment regimens are known to clinicians.

Methods of Diagnosis

Included in the invention are methods for diagnosing a bacterial infection. Presently, there are no preventative measures against bacterial infection such as, but not limited to, extraintestinal *E. coli* infection, for example *E. coli* bacteremia. Accordingly, identification of microbial determinants, for example RDIs, including *E. coli* RDIs, that contribute to extraintestinal *E. coli* infection are correlated with a diseased state and are useful in diagnostic methods.

The diagnostic methods of the invention include determining the level of expression of an RDI nucleic acid molecule, polypeptide or fragment in a subject sample, where an increased level of expression relative to a reference indicates that the subject has or has a propensity to develop extraintestinal *E. coli* infection.

In certain embodiments, the bacterial infection is any *E. coli* infection. The *E. coli* infection can be any extraintestinal *E. coli* infection, which can be an infection selected from, but not limited to, bacteremia, sepsis, meningitis or urinary tract infection.

In one embodiment, a subject having a bacterial infection will show an alteration in the detection of microbial determinants, for example E. coli RDIs. Alterations in gene expression are detected using methods known to the skilled artisan and described herein. Such information can be used to diagnose a bacterial infection. In another embodiment, alterations in gene expression, for example an alteration in the expression of bacterial RDIs is detected using real-time quantitative PCR (Q-rt-PCR) to detect changes in gene expression.

Primers used for amplification of an RDI nucleic acid molecule are useful in diagnostic methods of the invention. The primers of the invention embrace oligonucleotides of sufficient length and appropriate sequence so as to provide specific initiation of polymerization on a significant number of nucleic acids. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a locus strand. The primer must be sufficiently long to prime the synthesis of extension products in the presence of the inducing agent for polymerization. The exact length of primer will depend on many factors, including temperature, buffer, and nucleotide composition. The oligonucleotide primer typically contains between 12 and 27 or more nucleotides, although it may contain fewer nucleotides. Primers of the invention are designed to be "substantially" complementary to each strand of the genomic locus to be amplified and include the appropriate G or C nucleotides as discussed above. This means that the primers must be sufficiently complementary to hybridize with their respective strands under conditions that allow the agent for polymerization to perform. In other words, the primers should have sufficient complementarity with the 5' and 3' flanking sequences to hybridize therewith and permit amplification of the genomic locus. While exemplary primers are provided herein, it is understood that any primer that hybridizes with the target sequences of the invention are useful in the method of the invention for detecting RDI nucleic acid molecules.

In one embodiment, RDI-specific primers amplify a desired genomic target using the polymerase chain reaction (PCR). The amplified product is then detected using standard methods known in the art. In one embodiment, a PCR product (i.e., amplicon) or real-time PCR product is detected by probe binding. In one embodiment, probe binding generates a fluorescent signal, for example, by coupling a fluorogenic dye molecule and a quencher moiety to the same or different oligonucleotide substrates (e.g., TaqMan® (Applied Biosystems, Foster City, Calif., USA), Molecular Beacons (see, for example, Tyagi et al., Nature Biotechnology 14(3):303-8, 1996), SCORPIONS (Molecular Probes Inc., Eugene, Oreg., USA)). In another example, a PCR product is detected by the binding of a fluorogenic dye that emits a fluorescent signal upon binding (e.g., SYBRGREEN (Molecular Probes)). Such detection methods are useful for the detection of an RDI PCR product.

In another embodiment, hybridization with PCR probes that are capable of detecting an RDI nucleic acid molecule, including genomic sequences, or closely related molecules, may be used to hybridize to a nucleic acid sequence derived from a patient having a bacterial infection, for example an E. coli extraintestinal bacterial infection. The specificity of the probe determines whether the probe hybridizes to a naturally occurring sequence, allelic variants, or other related sequences. Hybridization techniques may be used to identify mutations indicative of a bacterial infection, or may be used to monitor expression levels of these genes (for example, by Northern analysis (Ausubel et al., supra).

In yet another embodiment, humans may be diagnosed for a propensity to develop a bacterial infection by direct analysis of the sequence of an RDI nucleic acid molecule. The sequence of an RDI nucleic acid molecule derived from a subject is compared to a reference sequence. An alteration in the sequence of the RDI nucleic acid molecule relative to the reference indicates that the patient has or has a propensity to develop a bacterial infection as described herein.

In another approach, diagnostic methods of the invention are used to assay the expression of an RDI polypeptide in a biological sample relative to a reference (e.g., the level of RDI polypeptide present in a corresponding control tissue). In one embodiment, the level of an RDI polypeptide is detected using an antibody that specifically binds an RDI polypeptide. Exemplary antibodies that specifically bind an RDI polypeptide are described herein. Such antibodies are useful for the diagnosis of a bacterial infection. Methods for measuring an antibody-RDI complex include, for example, detection of fluorescence, luminescence, chemiluminescence, absorbance, reflectance, transmittance, birefringence or refractive index. Optical methods include microscopy (both confocal and non-confocal), imaging methods and non-imaging methods. Methods for performing these assays are readily known in the art. Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra. Immunoassays can be used to determine the quantity of RDI in a sample, where an increase in the level of the RDI polypeptide is diagnostic of a patient having a bacterial infection.

In general, the measurement of an RDI polypeptide or nucleic acid molecule in a subject sample is compared with a diagnostic amount present in a reference. A diagnostic amount distinguishes between a neoplastic tissue and a control tissue. The skilled artisan appreciates that the particular diagnostic amount used can be adjusted to increase sensitivity or specificity of the diagnostic assay depending on the preference of the diagnostician. In general, any significant increase (e.g., at least about 10%, 15%, 30%, 50%, 60%, 75%, 80%, or 90%) in the level of an RDI polypeptide or nucleic acid molecule in the subject sample relative to a reference may be used to diagnose a bacterial infection. In one embodiment, the reference is the level of RDI polypeptide or nucleic acid molecule present in a control sample obtained from a patient that does not have a bacterial infection. In another embodiment, the reference is a baseline level of RDI present in a biologic sample derived from a patient prior to, during, or after treatment for a bacterial infection. In yet another embodiment, the reference is a standardized curve.

Methods of Detection

The methods of the invention also feature methods for detecting microbial determinants of bacterial infection. In preferred embodiments, two complimentary functional genomic approaches are used to identify E. coli K1 determinants contributing to bacteremia using. A first approach utilizes systematic genome comparison between clinical E. coli K1 strain RS 218 and non-pathogenic laboratory strain E. coli MG1655. A second approach utilizes in silico gene comparison. For example, in preferred embodiments, microarray may be used to examine and compare expression profiling during experimental E. coli bacteremia. Genome sequencing of the most common prototype *E. coli* K1 strain for bacteremia and meningitis, strain RS 218 (018:K1:H7) provides new tools for identifying microbial determinants contributing to *E. coli* bacteremia such as comparative genomics and microbial DNA microarrays.

Microbial DNA microarrays offer an opportunity for exploring the molecular pathogenesis of infectious, e.g., analysis of the entire gene expression profile of a bacterial pathogen during its interaction with the host. A common technical issue in the expression analysis of bacterial pathogens is the extraction of adequate quantities of intact bacterial RNA. The quality and the biological significance of microarray data is entirely dependent upon the structural integrity and the biological quality of the RNA (137). Prevention of transcriptional changes associated with preparative procedures of bacterial RNA is critical, but challenging since bacteria are capable of rapid transcriptional responses to their environment. An idea of how variable and sensitive the bacterial expression pattern might be is obtained from the average half-life of *E. coli* mRNA, experimentally estimated between 5 and 7 minutes (146-148). A number of protocols have been developed for the microarray analysis of bacteria during pathogen-host interaction. Most of them are designed to obtain a sample of pure bacterial RNA free of the host "contamination," and are well documented in the art (137-139, 141, 142, 145). This approach is preferable because host RNA may compete with bacterial RNA during cDNA synthesis and labeling, impede a correct quantification of the starting amount of bacterial RNA and limit the total amount of RNA to be used for probe generation. Elimination of the host component is, therefore, important. Nevertheless, such task needs to be achieved without allowing any alteration of the bacterial RNA and protocols must be properly validated. Selection of appropriate experimental models of infection is also important. The model must reflect the complexities of relevant host-pathogen interactions. The necessity to investigate the bacterial pathogen using such complex environment adds to the difficulty of obtaining microarray-grade, unbiased RNA.

Thus, use of a microbial DNA microarray that covers the genomes of several pathogenic *E. coli*, including *E. coli* K1 strain RS 218 is advantageous in certain embodiments. In addition, using a protocol to isolate microarray-grade bacterial RNA from infected rat blood is used in other exemplary embodiments to investigate what microbial factors contribute to the development of bacteremia in the infant rat model described herein.

The nucleotide sequences or portions thereof, of this invention are useful as probes for the detection of any one of the RDIs or fragments thereof in for example, a biological sample. Isolation of nucleic acids from a biological sample may be performed by standard methodology (Ausubel et al., (1987) in "Current Protocols in Molecular Biology", John Wiley and Sons, New York, N.Y.). Detection may be performed by a variety of conventional methodologies standard methodology, including, but not limited to, Northern Blot Analysis, PCR etc (Ausubel et al., (1987) in "Current Protocols in Molecular Biology", John Wiley and Sons, New York, N.Y.). The probes of the present invention are preferably labeled to provide for detection. Examples of labels include, but are not limited to, radioactive labels, fluorescent labels, photometric labels or chemical labels (Ausubel et al., (1987) in "Current Protocols in Molecular Biology", John Wiley and Sons, New York, N.Y.) In a preferred embodiment a biological sample is assayed for the presence of any bacterial RDI. In preferred embodiments the RDI is a gram negative bacterial RDI, and in exemplary embodiments is an RDI selected from RDI 1, 4, 7, 12, 13, 16, 20, 21, or 22 genes or gene products.

The nucleotide sequences of this invention can also be used as probes to isolate homologs in other species.

The nucleotide sequences or portions thereof, are useful in diagnostic assays for bacterial infection, for example extraintestinal bacterial infection, for example meningitic *E. coli*, in particular neonatal meningitic *E. coli*. The diagnostic assays may be performed as described above to detect nucleic acid sequences from a biological sample which are complimentary to the nucleic acid sequences of the invention. By way of example, the diagnostic assay may comprise an array of the nucleic acids of the invention attached to a support (e.g., dot blots on a nylon hybridization membrane Sambrook et al.,) that is contacted with the nucleic acids isolated from the biological sample nylon. In a preferred embodiment for the diagnostic assay the nucleic acid sequences comprise a microarray.

The nucleic acid sequences of the invention may be utilized as probes in microarrays comprising a solid phase on the surface of which are immobilized a population of the nucleic acids of the invention. Microarrays can be generated in a number of ways. The probes can be attached to a solid support or surface, which may be made from, for example, glass, plastic (e.g., polypropylene, nylon), polyacrylamide, nitrocellulose, or other materials. Methods for attaching the nucleic acids to the surface of the solid phase include, but are not limited to, printing on glass plates (Schena et al, 1995, Science 270:467-470; DeRisi et al, 1996, Nature Genetics 14:457-460; Shalon et al., 1996, Genome Res. 6:639-645; and Schena et al., 1995, Proc. Natl. Acad. Sci. U.S.A. 93:10539-11286); or ink jet printer; for oligonucleotide synthesis (U.S. application Ser. No. 09/008,120, filed Jan. 16, 1998).

The microarrays can also be high-density oligonucleotide arrays. Techniques are known for producing arrays containing thousands of oligonucleotides complementary to defined sequences (see, Fodor et al., 1991, Science 251:767-773; Pease et al., 1994, Proc. Natl. Acad. Sci. U.S.A. 91:5022-5026; Lockhart et al., 1996, Nature Biotechnology 14:1675; U.S. Pat. Nos. 5,578,832; 5,556,752; and 5,510,270; Blanchard et al., Biosensors & Bioelectronics 11:687-690). Other methods for making microarrays may also be utilized (Maskos and Southern, 1992, Nuc. Acids. Res. 20:1679-1684; U.S. Pat. No. 6,136,592; WO 200054883; WO 200055363; WO 200053812; WO 200014273). The microarrays may be used as is or incorporated into a biochip, multiwell or other device.

Preferably the microarrays of the present invention comprise, in addition to one or more of the nucleic acids of the present invention, nucleic acids from non-pathogenic, for example non-bacteremic, for example non-meningitic strains of *E. coli* as a control. In a preferred embodiment, any one of a bacterial RDI, in preferred embodiments a gram negative bacterial RDI, and in exemplary embodiments an RDI selected from the RDIs 1, 4, 7, 12, 13, 16, 20, 21, or 22 sequences or fragments is included in the microarray.

One of skill in the art will understand that the hybridization and wash conditions are chosen so that the nucleic acid sequences to be analyzed by the invention (e.g., the nucleic acids isolated from the biological sample) "specifically bind" or "specifically hybridize" to the nucleic acid sequences the array. Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, Current Protocols in Molecular Biology, Greene Publishing and Wiley-Interscience, New York).

Examples of biological samples that can be used in the above assays include, but are not limited to, cerebrospinal fluid, blood, urine, biopsy specimens, pathology specimens, and necropsy specimens.

Immunological Compositions

The invention also provides for a method of inducing an immunological response in a subject, particularly a human, which comprises inoculating the subject with the polypeptides of the invention, or fragments thereof, in a suitable carrier for the purpose of inducing or enhancing an immune response. In one embodiment, the invention provides immunogenic compositions comprising an E. coli RDI or fragments thereof in a pharmaceutically acceptable excipient. The immunogenic compositions of the invention can be administered to a subject to modulate an immune response. The administration of this immunological composition may be used either therapeutically in subjects already experiencing a bacterial infection, or may be used prophylactically to prevent a pathogen infection.

The preparation of vaccines is known to one skilled in the art. The vaccine includes an RDIs or fragment thereof. The RDIs, or fragments or variants thereof are delivered in vivo in order to induce an immune response. The polypeptides might be fused to a recombinant protein that stabilizes the polypeptide of the invention, aids in its solubilization, facilitates its production or purification.

Typically vaccines are prepared in an injectable form, either as a liquid solution or as a suspension. Solid forms suitable for injection may also be prepared as emulsions, or with the polypeptides encapsulated in liposomes. Vaccine antigens are usually combined with a pharmaceutically acceptable carrier, which includes any carrier that does not induce the production of antibodies harmful to the subject receiving the carrier. Suitable carriers typically comprise large macromolecules that are slowly metabolized, such as proteins, polysaccharides, polylactic acids, polyglycolic acids, polymeric amino acids, amino acid copolymers, lipid aggregates, and inactive virus particles. Such carriers are well known to those skilled in the art. These carriers may also function as adjuvants.

The RDIs, or fragments or variants thereof are useful as an adjuvant. Adjuvants are immunostimulating agents that enhance vaccine effectiveness. The RDIs, or fragments or variants thereof are administered in combination with an antigen of interest, such that the presence of the RDIs enhances the effectiveness of the immune response generated against the antigen of interest. The RDI composition may be combined with, any other adjuvant known in the art. Effective adjuvants include, but are not limited to, aluminum salts such as aluminum hydroxide and aluminum phosphate, muramyl peptides, bacterial cell wall components, saponin adjuvants, and other substances that act as immunostimulating agents to enhance the effectiveness of the composition.

Immunogenic compositions, i.e. the antigen, pharmaceutically acceptable carrier and adjuvant, also typically contain diluents, such as water, saline, glycerol, ethanol. Auxiliary substances may also be present, such as wetting or emulsifying agents, pH buffering substances, and the like. Proteins may be formulated into the vaccine as neutral or salt forms. The vaccines are typically administered parenterally, by injection; such injection may be either subcutaneously or intramuscularly. Additional formulations are suitable for other forms of administration, such as by suppository or orally. Oral compositions may be administered as a solution, suspension, tablet, pill, capsule, or sustained release formulation.

In addition, it is possible to prepare live attenuated microorganism vaccines that express recombinant polypeptides, for example of RDI, fragment thereof, or variant. Suitable attenuated microorganisms are known in the art, and include, for example, viruses and bacteria.

Vaccines are administered in a manner compatible with the dose formulation. The immunogenic composition of the vaccine comprises an immunologically effective amount of the antigenic polypeptides and other previously mentioned components. By an immunologically effective amount is meant a single dose, or a vaccine administered in a multiple dose schedule, that is effective for the treatment or prevention of an infection. The dose administered will vary, depending on the subject to be treated, the subject's health and physical condition, the capacity of the subject's immune system to produce antibodies, the degree of protection desired, and other relevant factors. Precise amounts of the active ingredient required will depend on the judgment of the practitioner, but typically range between 5 µg to 250 µg of antigen per dose.

Pharmaceutical Compositions

The present invention contemplates pharmaceutical preparations comprising RDI molecules or other functional substitutes, for example RDI analogs, together with pharmaceutically acceptable carriers. Polypeptides of the invention may be administered as part of a pharmaceutical composition. The compositions should be sterile and contain a therapeutically effective amount of the polypeptides in a unit of weight or volume suitable for administration to a subject.

Pharmaceutical compositions of the invention to be used for therapeutic administration should be sterile. Sterility is readily accomplished by filtration through sterile filtration membranes (e.g., 0.2 µm membranes), by gamma irradiation, or any other suitable means known to those skilled in the art. Therapeutic polypeptide compositions generally are placed into a container having a sterile access port, for example, an intravenous solution bag or vial having a stopper pierceable by a hypodermic injection needle. These compositions ordinarily will be stored in unit or multi-dose containers, for example, sealed ampoules or vials, as an aqueous solution or as a lyophilized formulation for reconstitution. As an example of a lyophilized formulation, 10 mL vials are filled with 5 mL of sterile-filtered 1% (w/v) aqueous solution, such as an aqueous solution of RDI polypeptide, and the resulting mixture can then be lyophilized. The infusion solution can be prepared by reconstituting the lyophilized material using sterile Water-for-Injection (WFI).

The polypeptides or analogs may be combined, optionally, with a pharmaceutically acceptable excipient. The term "pharmaceutically-acceptable excipient" as used herein means one or more compatible solid or liquid filler, diluents or encapsulating substances that are suitable for administration into a human. The term "carrier" denotes an organic or inorganic ingredient, natural or synthetic, with which the active ingredient is combined to facilitate administration. The components of the pharmaceutical compositions also are capable of being co-mingled with the molecules of the present invention, and with each other, in a manner such that there is no interaction that would substantially impair the desired pharmaceutical efficacy.

RDIs of the present invention can be contained in a pharmaceutically acceptable excipient. The excipient preferably contains minor amounts of additives such as substances that enhance isotonicity and chemical stability. Such materials are non-toxic to recipients at the dosages and concentrations employed, and include buffers such as phosphate, citrate, succinate, acetate, lactate, tartrate, and other organic acids or their salts; tris-hydroxymethylaminomethane (TRIS), bicarbonate, carbonate, and other organic bases and their salts; antioxidants, such as ascorbic acid; low molecular weight (for example, less than about ten residues) polypeptides, e.g., polyarginine, polylysine, polyglutamate and polyaspartate; proteins, such as serum albumin, gelatin, or immunoglobulins; hydrophilic polymers, such as polyvinylpyrrolidone (PVP), polypropylene glycols (PPGs), and polyethylene glycols (PEGs); amino acids, such as glycine, glutamic acid, aspartic acid, histidine, lysine, or arginine; monosaccharides, disaccharides, and other carbohydrates including cellulose or its derivatives, glucose, mannose, sucrose, dextrins or sulfated carbohydrate derivatives, such as heparin, chondroitin sulfate or dextran sulfate; polyvalent metal ions, such as divalent metal ions including calcium ions, magnesium ions and manganese ions; chelating agents, such as ethylenediamine tetraacetic acid (EDTA); sugar alcohols, such as mannitol or sorbitol; counterions, such as sodium or ammonium; and/or nonionic surfactants, such as polysorbates or poloxamers. Other additives may be included, such as stabilizers, anti-microbials, inert gases, fluid and nutrient replenishers (i.e., Ringer's dextrose), electrolyte replenishers, and the like, which can be present in conventional amounts.

The compositions, as described above, can be administered in effective amounts. The effective amount will depend upon the mode of administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject having an inflammatory disease or disorder, an effective amount is sufficient to reduce an inflammation. In some cases this is a local (site-specific) reduction of inflammation. In other cases, it is inhibition of systemic infection and/or sepsis. With respect to a subject having a neoplastic disease or disorder, an effective amount is an amount sufficient to stabilize, slow, or reduce the proliferation of the neoplasm. Generally, doses of active polypeptide compounds of the present invention would be from about 0.01 mg/kg per day to about 1000 mg/kg per day. It is expected that doses ranging from about 50 to about 2000 mg/kg will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of the RDI compositions of the present invention.

A variety of administration routes are available. The methods of the invention, generally speaking, may be practiced using any mode of administration that is medically acceptable, meaning any mode that produces effective levels of the active compounds without causing clinically unacceptable adverse effects. In one embodiment, a composition of the invention comprising an RDI or a nucleic acid molecule encoding the RDI is administered by inhalation. This method of administration is particularly advantageous because it provides the RDI or nucleic acid molecule directly to the lung epithelium. Other modes of administration include oral, rectal, topical, intraocular, buccal, intravaginal, intracisternal, intracerebroventricular, intratracheal, nasal, transdermal, within/on implants, e.g., fibers such as collagen, osmotic pumps, or grafts comprising appropriately transformed cells, etc., or parenteral routes. A particular method of administration involves coating, embedding or derivatizing fibers, such as collagen fibers, protein polymers, etc. with therapeutic proteins. Other useful approaches are described in Otto, D. et al., J. Neurosci. Res. 22: 83-91 and in Otto, D. and Unsicker, K. J. Neurosci. 10: 1912-1921.

The term "parenteral" includes subcutaneous, intrathecal, intravenous, intramuscular, intraperitoneal, or infusion. Compositions comprising RDIs can be added to a physiological fluid such as blood or synovial fluid. For CNS administration, a variety of techniques are available for promoting transfer of the therapeutic across the blood brain barrier including disruption by surgery or injection, drugs which transiently open adhesion contact between the CNS vasculature endothelial cells, and compounds that facilitate translocation through such cells. Oral administration can be preferred for prophylactic treatment because of the convenience to the patient as well as the dosing schedule.

Pharmaceutical compositions of the invention can optionally further contain one or more additional proteins as desired, including plasma proteins, proteases, and other biological material, so long as it does not cause adverse effects upon administration to a subject. Suitable proteins or biological material may be obtained from human or mammalian plasma by any of the purification methods known and available to those skilled in the art; from supernatants, extracts, or lysates of recombinant tissue culture, viruses, yeast, bacteria, or the like that contain a gene that expresses a human or mammalian plasma protein which has been introduced according to standard recombinant DNA techniques; or from the fluids (e.g., blood, milk, lymph, urine or the like) or transgenic animals that contain a gene that expresses a human plasma protein which has been introduced according to standard transgenic techniques.

Pharmaceutical compositions of the invention can comprise one or more pH buffering compounds to maintain the pH of the formulation at a predetermined level that reflects physiological pH, such as in the range of about 5.0 to about 8.0. The pH buffering compound used in the aqueous liquid formulation can be an amino acid or mixture of amino acids, such as histidine or a mixture of amino acids such as histidine and glycine. Alternatively, the pH buffering compound is preferably an agent which maintains the pH of the formulation at a predetermined level, such as in the range of about 5.0 to about 8.0, and which does not chelate calcium ions. Illustrative examples of such pH buffering compounds include, but are not limited to, imidazole and acetate ions. The pH buffering compound may be present in any amount suitable to maintain the pH of the formulation at a predetermined level.

Pharmaceutical compositions of the invention can also contain one or more osmotic modulating agents, i.e., a compound that modulates the osmotic properties (e.g, tonicity, osmolality and/or osmotic pressure) of the formulation to a level that is acceptable to the blood stream and blood cells of recipient individuals. The osmotic modulating agent can be an agent that does not chelate calcium ions. The osmotic modulating agent can be any compound known or available to those skilled in the art that modulates the osmotic properties of the formulation. One skilled in the art may empirically determine the suitability of a given osmotic modulating agent for use in the inventive formulation. Illustrative examples of suitable types of osmotic modulating agents include, but are not limited to: salts, such as sodium chloride and sodium acetate; sugars, such as sucrose, dextrose, and mannitol; amino acids, such as glycine; and mixtures of one or more of these agents and/or types of agents. The osmotic modulating agent(s) may be present in any concentration sufficient to modulate the osmotic properties of the formulation.

Compositions comprising RDIs of the present invention can contain multivalent metal ions, such as calcium ions, magnesium ions and/or manganese ions. Any multivalent metal ion that helps stabilize the RDI composition and that will not adversely affect recipient individuals may be used. The skilled artisan, based on these two criteria, can determine suitable metal ions empirically and suitable sources of such metal ions are known, and include inorganic and organic salts.

Pharmaceutical compositions of the invention can also be a non-aqueous liquid formulation. Any suitable non-aqueous liquid may be employed, provided that it provides stability to the active agents (s) contained therein. Preferably, the non-aqueous liquid is a hydrophilic liquid. Illustrative examples of suitable non-aqueous liquids include: glycerol; dimethyl sulfoxide (DMSO); polydimethylsiloxane (PMS); ethylene glycols, such as ethylene glycol, diethylene glycol, triethylene glycol, polyethylene glycol ("PEG") 200, PEG 300, and PEG 400; and propylene glycols, such as dipropylene glycol, tripropylene glycol, polypropylene glycol ("PPG") 425, PPG 725, PPG 1000, PPG 2000, PPG 3000 and PPG 4000.

Pharmaceutical compositions of the invention can also be a mixed aqueous/non-aqueous liquid formulation. Any suitable non-aqueous liquid formulation, such as those described above, can be employed along with any aqueous liquid formulation, such as those described above, provided that the mixed aqueous/non-aqueous liquid formulation provides stability to the RDI(s) contained therein. Preferably, the non-aqueous liquid in such a formulation is a hydrophilic liquid. Illustrative examples of suitable non-aqueous liquids include: glycerol; DMSO; PMS; ethylene glycols, such as PEG 200, PEG 300, and PEG 400; and propylene glycols, such as PPG 425, PPG 725, PPG 1000, PPG 2000, PPG 3000 and PPG 4000.

Suitable stable formulations can permit storage of the active agents in a frozen or an unfrozen liquid state. Stable liquid formulations can be stored at a temperature of at least −70° C., but can also be stored at higher temperatures of at least 0° C., or between about 0.1° C. and about 42° C., depending on the properties of the composition. It is generally known to the skilled artisan that proteins and polypeptides are sensitive to changes in pH, temperature, and a multiplicity of other factors that may affect therapeutic efficacy.

In certain embodiments a desirable route of administration can be by pulmonary aerosol. Techniques for preparing aerosol delivery systems containing polypeptides are well known to those of skill in the art. Generally, such systems should utilize components that will not significantly impair the biological properties of the antibodies, such as the paratope binding capacity (see, for example, Sciarra and Cutie, "Aerosols," in *Remington's Pharmaceutical Sciences*, 18th edition, 1990, pp 1694-1712; incorporated by reference). Those of skill in the art can readily modify the various parameters and conditions for producing polypeptide aerosols without resorting to undue experimentation.

Other delivery systems can include time-release, delayed release or sustained release delivery systems. Such systems can avoid repeated administrations of RDIs, increasing convenience to the subject and the physician. Many types of release delivery systems are available and known to those of ordinary skill in the art. They include polymer base systems such as polylactides (U.S. Pat. No. 3,773,919; European Patent No. 58,481), poly(lactide-glycolide), copolyoxalates, polycaprolactones, polyesteramides, polyorthoesters, polyhydroxybutyric acids, such as poly-D-(−)-3-hydroxybutyric acid (European Patent No. 133, 988), copolymers of L-glutamic acid and gamma-ethyl-L-glutamate (Sidman, K. R. et al., Biopolymers 22: 547-556), poly (2-hydroxyethyl methacrylate) or ethylene vinyl acetate (Langer, R. et al., J. Biomed. Mater. Res. 15:267-277; Langer, R. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono- di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

Another type of delivery system that can be used with the methods and compositions of the invention is a colloidal dispersion system. Colloidal dispersion systems include lipid-based systems including oil-in-water emulsions, micelles, mixed micelles, and liposomes. Liposomes are artificial membrane vessels, which are useful as a delivery vector in vivo or in vitro. Large unilamellar vessels (LUV), which range in size from 0.2-4.0 μm can encapsulate large macromolecules within the aqueous interior and be delivered to cells in a biologically active form (Fraley, R., and Papahadjopoulos, D., Trends Biochem. Sci 6: 77-80).

Liposomes can be targeted to a particular tissue by coupling the liposome to a specific ligand such as a monoclonal antibody, sugar, glycolipid, or protein. Liposomes are commercially available from Gibco BRL, for example, as LIPOFECTIN and LIPOFECTACE, which are formed of cationic lipids such as N-[1-(2, 3 dioleyloxy)-propyl]-N,N,N-trimethylammonium chloride (DOTMA) and dimethyl dioctadecylammonium bromide (DDAB). Methods for making liposomes are well known in the art and have been described in many publications, for example, in DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88, 046; EP 143,949; EP 142,641; Japanese Pat. Appl. 83-118008; U.S. Pat. Nos. 4,485,045 and 4,544,545; and EP 102,324. Liposomes also have been reviewed by Gregoriadis, G., Trends Biotechnol., 3: 235-241).

Another type of vehicle is a biocompatible microparticle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System"). PCT/US/0307 describes biocompatible, preferably biodegradable polymeric matrices for containing an exogenous gene under the control of an appropriate promoter. The polymeric matrices can be used to achieve sustained release of the exogenous gene or gene product in the subject.

The polymeric matrix preferably is in the form of a microparticle such as a microsphere (wherein an agent is dispersed throughout a solid polymeric matrix) or a microcapsule (wherein an agent is stored in the core of a polymeric shell). Microcapsules of the foregoing polymers containing drugs are described in, for example, U.S. Pat. No. 5,075,109. Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery that is to be used. Preferably, when an aerosol route is used the polymeric matrix and RDIs are encompassed in a surfactant vehicle. The polymeric matrix composition can be selected to have both favorable degradation rates and also to be formed of a material, which is a bioadhesive, to further increase the effectiveness of transfer. The matrix composition also can be selected not to degrade, but rather to release by diffusion over an extended period of time. The delivery system can also be a biocompatible microsphere that is suitable for local, site-specific delivery. Such microspheres are disclosed in Chickering, D. E., et al., Biotechnol. Bioeng., 52: 96-101; Mathiowitz, E., et al., Nature 386: 410-414.

Both non-biodegradable and biodegradable polymeric matrices can be used to deliver the RDI compositions of the invention to the subject. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly (octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly (ortho)esters, poly(butic acid), poly(valeric acid), and poly (lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Combination Therapies for the Treatment of Bacterial Infection

A RDI composition of the invention may be used in combination with any therapy known in the art for the treatment of bacterial infection, for example *E. coli* extraintestinal infection, including but not limited to but not limited to meningitis, bacteremia, sepsis, UTI or pneumonia. Exemplary drugs that can be used in combination therapy include, but are not limited to antimicrobial agents, leukocyte transfusion or anti-inflammatory cytokines.

Combination Therapies for the Treatment of Inflammation

Compositions and methods of the invention can be used in combination with existing anti-inflammatory treatment modalities, including but not limited to, drug therapy, and administration with anti-inflammatory cytokines. Methods of the invention can optionally comprise contacting inflammatory cells with a RDI composition in combination with other anti-inflammatory drug treatments such as, but not limited to, antihistamines, non-steroidal anti-inflammatory agents (NSAIDs), eicosanoid receptor antagonists, cytokine antagonists, monoclonal antibodies, 3-hydroxymethylglutaryl-coenzyme A (HMG-CoA) reductase inhibitors, and corticosteroids (see, for example, Goodman and Gilman's *The Pharmacological Basis of Therapeutics*).

Antihistamines fall generally under three broad classes, according to the histamine receptor subtype they antagonize and display specificity for. Histamine H1 receptors are primarily responsible for the anti-inflammatory response, while H2 receptors are limited to gastric acid secretion. Histamine H1 receptor antagonists include, but are not limited to, carbinoxamine, clemastine, diphenhydramine, dimenhydrinate, pyrilamine, tripelennamine, chlorpheniramine, brompheniramine, chlorcyclizine, acrivastine, promethazine, as well as piperazines such as astemizole, levocabastine, hydroxyzine, cyclizine, cetirizine, meclizine, loratadine, fexofenadine, and terfenadine.

NSAIDs include the salicylate derivatives, para-aminophenol derivatives, indole and indene acetic acids, heteroaryl acetic acids, arylpropionic acids, anthranilic acids (also known in the art as fenamates), enolic acids, and alkanones. Salicylate derivates include aspirin, sodium salicylate, choline magnesium trisalicylate, salsalate, diflunisal, salicylsalicylic acid, sulfasalazine, and olsalazine, but are not limited to these drugs. Para-aminophenol derivates are exemplified by acetaminophen. Indomethacin, sulindac, and etodolac comprise indole and indene acetic acids, while heteroaryl acetic acids include tolmetin, diclofenac, and ketorolac. Examples of arylpropionic acids include ibuprofen, naproxen, flurbiprofen, ketoprofen, fenoprofen, and oxaprozin. Fenamates, include but are not limited to mefenamic acid and meclofenamic acid. Some examples of enolic acids include the oxicams piroxicm and tenoxicam, and pyrazolidinediones such as phenylbutazone and oxyphenthatrazone. Alkanones can comprise nabumetone.

Eicosanoid receptor antagonists include, but are not limited to, leukotriene modifiers, which can act as leukotriene receptor antagonists by selectively competing for LTD-4 and LTE-4 receptors. These compounds include, but are not limited to, zafirlukast tablets, zileuton tablets, and montelukast. Zileuton tablets function as 5-lipoxygenase inhibitors. Cytokine antagonists can comprise anti-TNF$\alpha$ antibodies, and fusion proteins of the ligand binding domain of the TNF$\alpha$ receptor and the Fc portion of human immunoglobulin G1. Other cytokine antagonists include recombinant human interleukin-1 receptor antagonist, recombinant human IFN$\alpha$, recombinant human IFN$\beta$, IL-4 muteins, soluble IL-4 receptors, immunosuppressants (such as tolerizing peptide vaccine), anti-IL-4 antibodies, IL-4 antagonists, anti-IL-5 antibodies, soluble IL-13 receptor-Fc fusion proteins, anti-IL-9 antibodies, CCR3 antagonists, CCR5 antagonists, VLA-4 inhibitors, downregulators of IgE, among others.

Corticosteroids cause a decrease in the number of circulating lymphocytes as a result of steroid-induced lysis of lymphocytes, or by alterations in lymphocyte circulation patterns (Kuby, J. (1998) In: *Immunology* 3$^{rd}$ Edition W.H. Freeman and Company, New York; Pelaia, G. et al. Life Sci. 72(14): 1549-61). Corticosteroids affect the regulation of nuclear factor κB (NF-κB) by inducing the upregulation of an inhibitor of NF-κE known as IκB, which sequesters NF-κB in the cytoplasm and prevents it from transactivating pro-inflammatory genes in the nucleus. Corticosteroids also reduce the phagocytic ability of macrophages and neutrophils, as well as reducing chemotaxis. Examples of corticosteroids are alclometasone, amcinonide, beclomethasone, betamethasone, clobetasol, clocortolone, cortisol, hydrocortisone, prednisolone, and prednisone, but are not limited to these examples.

Methods of the invention can optionally comprise contacting cells with RDI(s) in combination with other anti-inflammatory cytokines such as, but not limited to, interleukin-4 (IL-4), interleukin-10 (IL-10), interleukin-13 (IL-13), interleukin-16 (IL-16), interleukin-1 receptor antagonist (IL-1ra), interferon α (IFNα), transforming growth factor-β (TGF-β), among others. The cytokines may be administered together or separately in combination with RDI(s) in the compositions and methods described herein.

The balance between pro-inflammatory cytokines and anti-inflammatory cytokines determines the net effect of an inflammatory response. The type, duration, and also the extent of cellular activities induced by one particular cytokine can be influenced considerably by the nature of the target cells, the micro-environment of a cell, depending, for example, on the growth and activation state of the cells, the type of neighboring cells, cytokine concentrations, the presence of other cytokines, and even on the temporal sequence of several cytokines acting on the same cell.

Combination Therapy for the Treatment of a Pathogen Infection

In another embodiment, a RDI composition of the invention that targets a pathogen cell may be used in combination with any anti-pathogen therapy known in the art. Exemplary anti-pathogen therapies include antibiotics, antivirals, fungicides, nematicides, and parasiticides, or any other biocide. Parasiticides are agents that kill parasites directly and can be used in combination with the methods and compositions described herein. Such compounds are known in the art and are generally commercially available. Exemplary parasiticides useful for human administration include but are not limited to albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethoprim-sulfamethoxazole, and tryparsamide some of which are used alone or in combination with others.

Other anti-pathogen therapeutics useful in combination with a method of the invention include, but are not limited to, any one or more of the following: agent which reduces the activity of or kills a microorganism and includes but is not limited to Aztreonam; Chlorhexidine Gluconate; Imidurea; Lycetamine; Nibroxane; Pirazmonam Sodium; Propionic Acid; Pyrithione Sodium; Sanguinarium Chloride; Tigemonam Dicholine; Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Aziocillin Sodium; Bacanipicillin-Hydrochloride; Bacitracin; Bacitracin Methylene Disalicylate; Bacitracin Zinc; Bambennycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor, Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefinenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride, Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin lydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacil; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffunycin; Streptomycin Sulfate; Streptonicozid; Sulfabenz: Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium: Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin; Difloxacin Hydrochloride; Lauryl Isoquinolinium Bromide; Moxalactam Disodium; Ornidazole; Pentisomicin; and Sarafloxacin Hydrochloride.

Antibodies

This invention further comprises an antibody or antibodies reactive with the RDI protein or polypeptides or portion thereof. In this embodiment of the invention the antibodies are monoclonal or polyclonal in origin and are produced by conventional methodology (Kohler and Milstein (1975) Nature 256, 495-497; Campbell "Monoclonal Antibody Technology, the Production and Characterization of Rodent and Human Hybridomas" in Burdon et al. (eds.) (1985) "Laboratory Techniques in Biochemistry and Molecular Biology," Volume 13, Elsevier Science Publishers, Amsterdam; PCT patent applications: publication number WO 901443, WO 901443 and WO 9014424 and in Huse et al. (1989) Science 246:1275-1281). The protein or portions thereof used to generate the antibodies may be isolated from E. coli, recombinantly produced, or commercially synthesized (Merrifield, R. B. (1963) J. Amer. Soc. 85:2149). If the portion of the protein selected for generating antibodies is too short to be antigenic it may be conjugated to a carrier molecule to enhance the antigenicity of the peptide. Examples of carrier molecules, include, but are not limited to, human albumin, bovine albumin and keyhole limpet hemo-cyanin ("Basic and Clinical Immunology" (1991) Stites, D. P. and Terr A. I. (eds) Appleton and Lange, Norwalk Conn., San Mateo, Calif.).

The antibodies of this invention may be used in immunoassays to detect the novel proteins in biological samples. Examples of immunoassays that may be used include, but are not limited to, radioimmunoassay, Western blot assay, immunofluorescent assay, enzyme immunoassay, chemiluminescent assay, immunohistochemical assay and the like. (In "Principles and Practice of Immunoassay" (1991) Christopher P. Price and David J. Neoman (eds), Stockton Press, New York, N.Y.; Ausubel et al. (eds) (1987) in "Current Protocols in Molecular Biology" John Wiley and Sons, New York, N.Y.). Biological samples appropriate for such detection assays include, but are not limited to, blood samples, cerebral spinal fluid, urine, biopsy specimens, pathology specimens, and, necropsy specimens. Proteins may be isolated from biological samples by conventional methods described in (Ausubel et al., (eds) (1987) in "Current Protocols in Molecular Biology" John Wiley and Sons, New York, N.Y.).

The proteins or portions thereof of the invention may be used as a vaccine. The vaccine may be provided prior to any clinical indicia of bacterial meningitis or during an infection to enhance the patient's own immune response to the meningitic pathogens carrying virulence proteins but not probiotic bacteria. The vaccine, which acts as an immunogen may comprise one or more of the proteins of the invention or portions thereof. Vaccination can be conducted by conventional methods. For example, the immunogen can be used in a suitable diluent such as saline or water, or complete or incomplete adjuvants. Further, the immunogen may or may not be bound to a carrier to make the protein immunogenic. Examples of such carrier molecules include but are not limited to bovine serum albumin (BSA), keyhole limpet hemocyanin (KLH), tetanus toxoid, and the like. The immunogen also may be coupled with lipoproteins or administered in liposomal form or with adjuvants. The immunogen can be administered by any route appropriate such as intravenous, intraperitoneal, intramuscular, subcutaneous, and the like. The immunogen may be administered once or at periodic intervals until a significant titer of anti-GIMA immune cells or anti-GIMA antibody is produced. Alternatively the expression vectors of the invention may be utilized as vaccines. For example, an expression vector comprising all or part of the gene sequence for the GimA genes including ibeA, whose proteins have been shown to be immunogenic virulence factors can be used. The GimA genes can be cloned into a plasmid vector such as p'VR1020 (Vical, Inc., San Diego, Calif.). The vaccine may be tested in an animal model such as mice. This DNA vaccine can be delivered to mice by intradermal inoculation and the antibody titers in the antisera from the immunized mice measured by enzyme-linked immunosorbent assay. The elicited antibodies can also be tested by immunoblotting with GimA proteins including IbeA. Following the initial immunization and a few (e.g., 2-4) consecutive boosts, each at 2-week intervals, protection can be tested in a neonatal mouse model of E. coli meningitis.

The antibodies of the invention can also be administered to a subject as anti-meningitic bacterial agents. Preferably the antibodies administered are designed so to minimize an adverse immune response to the antibody itself (e.g., chimeric antibodies, humanized antibodies; Robinson et al., International Patent Application 184,187; Taniguchi M., European Patent Application 171,496; Morrison et al., European Patent Application 173,494; Neuberger et al., PCT Application WO 86/01533; Cabilly et al., 1987 Proc. Natl. Acad. Sci. USA 84:3439; Nishimura et al., 1987 Canc. Res. 47:999; Wood et al., 1985. Nature 314:446; Shaw et al., 1988 J. Natl. Cancer Inst. 80: 15553; Morrison S., 1985 Science 229:1202 and by Oi et al., 1986 BioTechniques 4:214.).

Kits

The invention also provides kits for immunizing a subject against a bacterial infection, the kit comprising a pharmaceutical composition as described herein. The invention provides kits for immunizing a subject against a bacterial infection, the kit comprising an immunogenic composition as described herein. The kits also contain instructions for use.

The invention provides kits for treating or preventing a bacterial infection in a subject, the kit comprising a pharmaceutical composition as described herein, and includes instructions for use.

EXAMPLES

It should be appreciated that the invention should not be construed to be limited to the examples that are now described; rather, the invention should be construed to include any and all applications provided herein and all equivalent variations within the skill of the ordinary artisan.

Example 1

Relationship Among E. coli Strains Isolated from Cerebrospinal Fluid

Based on the genome sequence information of the most common prototypic E. coli K1 strain for bacteremia and meningitis, strain RS 218 (018:K1), a comparative analysis of two genomes (clinical E. coli K1 strain RS 218 and laboratory E. coli K-12 strain MG 1655) was carried out. Based on the genome sequence alignment with E. coli strain MG 1655, 22 genomic islands from strain RS218 were identified that are larger than 10 kb and are absent in strain MG1655. Previous studies using comparative macrorestriction mapping and subtraction hybridization of the chromosomes of E. coli K1 (e.g., 018:K1 strains RS 218 and C5) compared to non-pathogenic E. coli have identified 500 kb spread over at least 12 chromosomal loci specific to E. coli K1 (92, 93). Mapping studies reveal that those E. coli loci are located at different regions of E. coli K1 chromosome. As described herein, 22 RDIs (termed after RS218-derived islands) are also shown to be located at different regions of E. coli K1 RS 218 chromosome. FIG. 1 is a genomic map of E. coli RS 218-derived islands (RDIs). The large circle represents the E. coli common backbone large circle into which are inserted 22 islands of RS 218-specific DNA, represented as smaller circles. The relative location to E. coli K-12 strain MG 1655 genome and size of each island are indicated in the map, where *0/100 minute mark.

Figure 2:
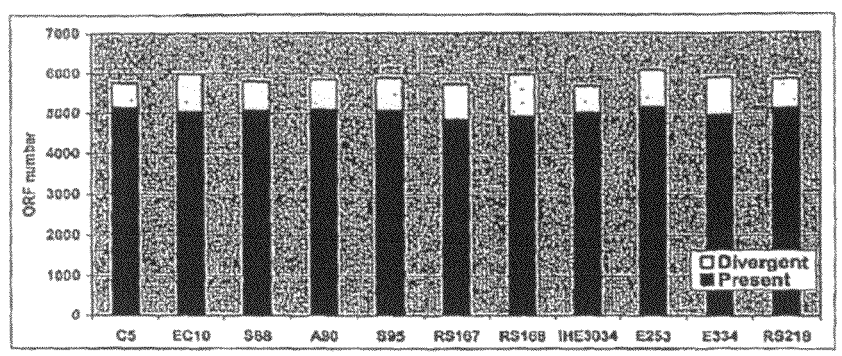
FIG. 2 is a graph showing the genome of 11 representative strains of E. coli K1.

Eleven strains of E. coli K1 were selected which were isolated from the cerebrospinal fluid (CSF) of patients with meningitis. These strains included serotypes that are shown to be common in E. coli meningitis, i.e., 01, 07, 012, 016, and 018. In addition, E. coli K1 isolates belonging to a new 045:K1 group were also included, and were shown to be predominant in neonates with E. coli meningitis from France (61). After data analysis, the ORFs of these 11 representative strains were estimated. FIG. 2 shows the genome of 11 representative strains of E. coli K1. The total ORF numbers in the genome of the 11 strains are close to each other, from 4852 (strain RS167) to 5147 ORFs (strain E253), as shown in FIG. 2. The total ORFs were calculated based on micro array hybridization. ORFs with intensity less than negative control value (median value of 95 negative control oligonucleotides) are considered as "absent" and ORFs with intensity greater than 1000 are considered as "present". If both channels cannot be determined using the above criteria, these ORFs were considered as "divergent". For the remaining ORFs, if channel A showed "absent" and the ratio of intensities (BfA) was less than 3.0, these ORFs in channel B were also considered as "absent", otherwise "divergent." If channel A showed "present" and the ratio of intensities (BfA) is less than 0.3, these ORFs in channel B were considered as "absent", otherwise the ORFs were considered as "present." Some strains may harbor specific ORFs, which may not be detectable by microarray, and thus the actual ORF numbers may be higher than those shown in FIG. 2. To validate the micro array data, 32 ORFs which have been sequenced either in strain RS218 or strain C5 were chosen for in silico analysis, shown in Table 1a below. The comparison showed consistency between microarray and in silico analysis, indicating that the microarray data are reliable.

TABLE 1a

| ID | Gene | Annotation | RS218 (3-6) | | C5 (1, 2) | |
|---|---|---|---|---|---|---|
| | | | CGH[a] | Blast[b,c,d] | CGH | Blast |
| AAL61901 | cdlD | Hypothetical protein | P | + | P | N/A |
| AAL61902 | cglC | Putative Betaine/Carnitine/Choline Transporters | P | + | P | N/A |
| AAL61900 | cglT | Putative transporter, MFS super family | D | + | P | N/A |
| Z4911 | chuA | Homo utilization/transport protein | P | N/A | P | ± |
| AAL61906 | gcxI | Putative hydroxypyruvate isomerase | P | + | P | N/A |
| AAL61903 | gcxK | Putative glycerate kinase | P | + | P | N/A |
| AAL61904 | gcxR | 2-hydroxy-3-oxopropionate reductase, also called tartronate semialdehyde reductase | P | + | P | N/A |
| AAF98391 | ibeA | Invasion protein ibeA | P | + | P | N/A |
| b0572 | ibeB | Invasion protein ibeB | P | + | P | N/A |
| AAL61907 | ibgR | Putative transcriptional regulator | P | + | P | N/A |
| AAL61908 | ibgT | Na+/H+ antiporter NhaC homolog | P | + | P | N/A |
| CAD66179 | iroB | Putative glucosyltransferase | P | N/A | P | + |

TABLE 1a-continued

| | | | RS218 (3-6) | | C5 (1, 2) | |
|---|---|---|---|---|---|---|
| ID | Gene | Annotation | CGH[a] | Blast[b,c,d] | CGH | Blast |
| C3698 | kpsM | Polysialic acid transport protein KpsM | P | + | P | ± |
| AAA24214 | kpsS | KpsS protein | P | + | P | ± |
| C3697 | kpsT | KpsT protein | P | + | P | ± |
| b1621 | malX | PT8 family enzyme IIC (N-terminal) | P | + | P | ± |
| AAA24211 | neuC | Polysialic acid biosynthesis protein P7 | P | + | P | ± |
| C5406 | ptnI | Putative phosphoendpyruvate-protein phosphotransferase, EI/HPr/EIIA | D | + | P | N/A |
| AAL83751 | puvA | Phage hypothetical protein | P | + | A | N/A |
| b2741 | rpoS | sigma S (sigma 38) factor of RNA, polymerase, majorsigma factor during stationary phase | P | + | P | N/A |
| Z4915 | shuX | ShuX-like protein | P | N/A | P | ± |
| AAA92657 | traJ | Positive regulator for DNA conjugation | P | + | P | ± |
| b3865 | yihA | Putative GTPase with nucleoside triP hydrolase domain | P | N/A | P | ± |
| b3955 | yijP | putative membrane protein | P | + | P | N/A |
| C5350 | | Putative arginine daiminase | P | N/A | P | + |
| C3785 | | Arylsulfate sulfotransferase | P | + | P | N/A |
| AAO43651 | | Putative phosphotransferase system protein | P | N/A | P | + |
| AAO43652 | | Putative phosphotransferase system protein | P | N/A | P | + |
| AAO43653 | | Putative phosphotransferase system protein | P | N/A | P | + |
| AAO43654 | | Putative phosphotransferase system protein | P | N/A | P | + |
| AAO43655 | | Phosphoglycerate dehydrogenase | P | N/A | P | + |
| AAO43656 | | Dihydrodipicolinate synthase | P | N/A | P | + |

Figure 3:
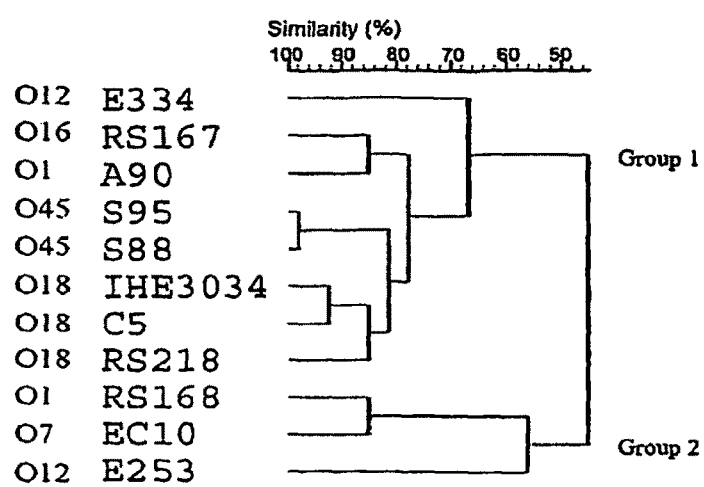
FIG. 3 is a schematic showing the clustering of 11 representative meningitis-causing E. coli K1 strains based on microarray data.

Next, the genetic relationship between the strains was examined. To evaluate the relationship among these 11 representative strains, hierarchical clustering was performed, using the data from genome comparative hybridization. The results are shown in FIG. 3. In FIG. 3, the clustering of 11 representative meningitis-causing E. coli K1 strains based on microarray data is shown. Data was imported from GenePix and manipulated and clustered, using established algorithms implemented in the software program Cluster (62). Average linkage clustering with centered correlation was used. Tree View software was used to generate visual representations of clusters. Clustering revealed that some E. coli K1 strains with the same 0 serotypes are closely related to each other. For example, 018:K1:H7 strains RS218, 11E3034 and C5 are closely related to each other and the two 045 strains, S88 and S95, are most closely related to each other. Clustering analysis also linked E. coli strains with different 0 serotypes. For example, strains ECI0 (07), RS168 (01) and E253 (012) were clustered together. Strain RS168, which belongs to 01, was found to be close to strain EC10 (07), not to strain A90 (01). Similarly, strains E252 and E334, belonging to 012, were clustered to different groups. Overall, strains EC10, RS168 and E253 represent a distinct cluster and appear to be most distantly related to the RS218 group. Here, based on genome similarity, the cluster that contains strains RS218, 11E3034, C5, RS167, A90, S88, S95 and E334 was named as Group 1, and the other strains was named as Group 2.

To examine phylogenetic grouping, all the 11 representative strains of E. coli 1K1 were determined for E. coli phylogenetic group by using a combination of two genes (chuA and yjaA) and an anonymous DNA fragment (TspE4C2) (63). The triplex PCR results showed that strains RS218, 11E3034, C5, A90, RS167, E334, S88 d S95 belong to group B2 while strains EC10 and RS168 are in group D and strain E253 is in group A.

Example 2

Examination of E. coli Virulence Factors

Next, the distribution of selected E. coli virulence factors printed on microarray among these 11 representative E. coli K1 strains was examined based on the available information that may be relevant to meningitis. The results are shown in Table 1b, below.

TABLE 1b

| | | Presence of virulence factors in strains | | | | | | | | | |
|---|---|---|---|---|---|---|---|---|---|---|---|
| ORFs | Function | RS215 | C5 | IHE3034 | S89 | S95 | A90 | RS187 | E334 | EC10 | RS165 | E253 |
| cnf1 | Cytotoxic necrotizing factor 1 | + | + | − | − | − | − | − | − | − | − | − |
| aslA | Arylsulfatase-like gene | + | +/− | +/− | +/− | +/− | +/− | + | + | +/− | +/− | + |
| fhuA | Forrichrome-iron receptor procursor, fluA | + | + | + | + | + | + | + | + | +/− | + | + |
| fyuA | Pesticinhyersinialactin receptor protein | + | +/− | + | +/− | + | + | + | + | + | + | + |
| hlyABCD | Homolysin | + | + | − | − | − | − | − | + | − | − | − |
| hlyE | Homolysin E | − | − | − | − | − | − | − | − | +/− | +/− | − |
| ibeA | Invasion ibeA | + | + | + | − | − | − | + | + | − | − | − |
| ibeB | Invasion ibeB | + | + | + | + | + | + | + | + | + | + | + |
| iha | Adhesin | − | − | − | − | − | − | + | + | + | + | + |
| iroN | Foric uptake proteins | + | + | + | + | + | + | + | − | − | − | − |
| iucABCD | iucABCD protein | − | − | − | + | + | + | − | + | + | + | + |
| iutA | iucA protein | − | − | − | − | − | − | − | + | + | + | + |
| malX | PTS family enzyme IC | + | + | + | + | + | + | + | + | + | + | + |
| ompA | Outer membrane protein | + | + | + | + | + | + | + | + | + | + | + |
| sfaffoc | S limbia | + | + | + | − | − | − | − | − | − | − | − |

TABLE 1b-continued

| | | Presence of virulence factors in strains | | | | | | | | | |
|---|---|---|---|---|---|---|---|---|---|---|---|
| ORFs | Function | RS215 | C5 | IHE3034 | S89 | S95 | A90 | RS187 | E334 | EC10 | RS165 | E253 |
| sfaG | FIC minor ingibitor | + | + | + | +/− | +/− | +/− | +/− | +/− | + | + | + |
| pepA | P limbia | + | − | − | + | + | + | +/− | + | + | + | + |
| hecA | Hemolysinhemagglutinin like protein | + | + | − | − | − | − | − | − | − | − | − |
| flu | Antigan 43 | + | + | + | + | + | + | +/− | + | − | + | + |
| hek | Adhesin/virulence factor | + | + | − | +/− | +/− | +/− | − | +/− | +/− | +/− | +/− |
| traJ | TraI protein | + | + | − | − | − | − | + | + | − | − | + |
| neu | K1 capsule | + | + | + | + | + | + | + | + | + | + | + |
| sit ABCD | Sit protains | + | + | + | + | + | + | + | + | + | + | + | a only microarray date are given; not PCR confirmation results.
b "+" means present; "−" means absent, "+/−" means divergent.

Figure 4A:
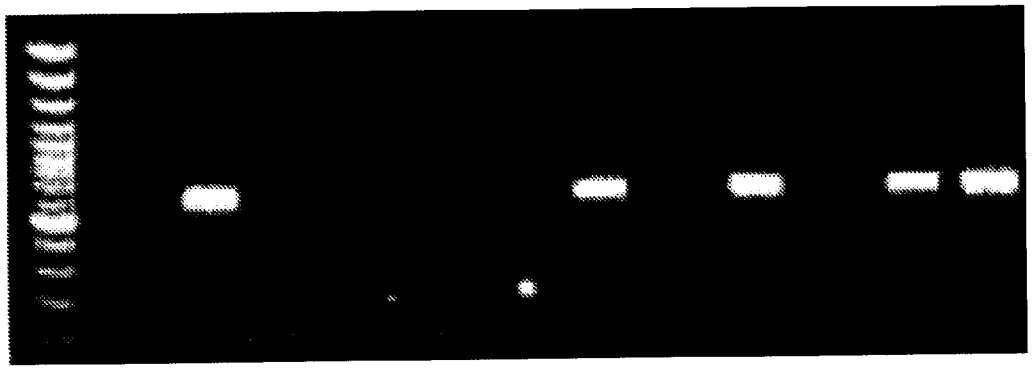
FIG. 4A to FIG. 4F show gels from PCR analysis. Selected genes were examined by PCR to confirm microarray data.
Figure 4B:
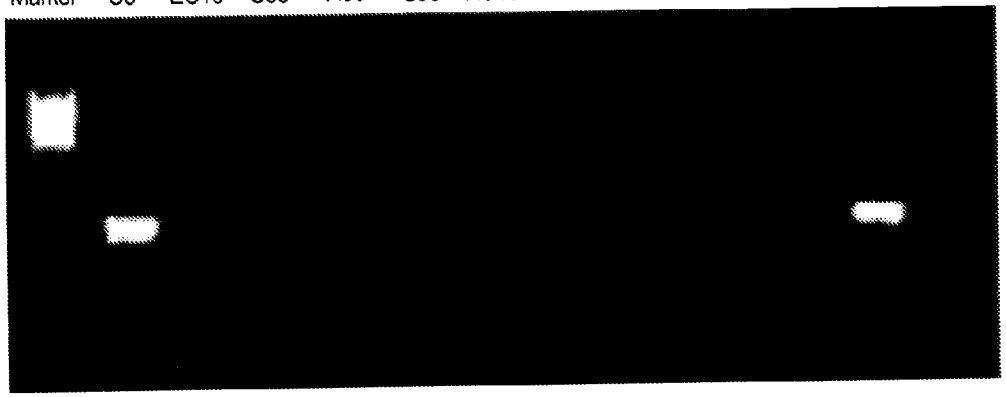
Figure 4C:
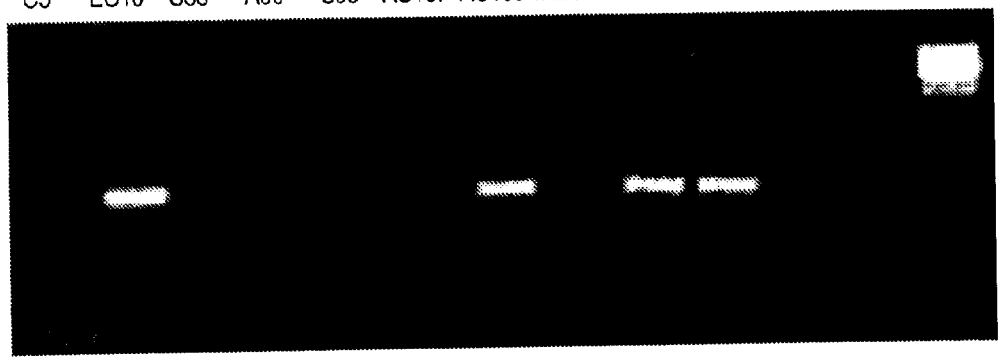
Figure 4D:
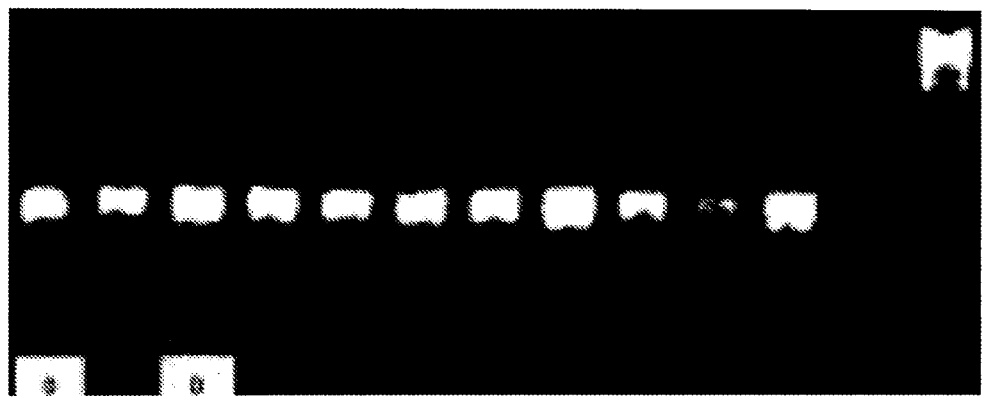
Figure 4E:
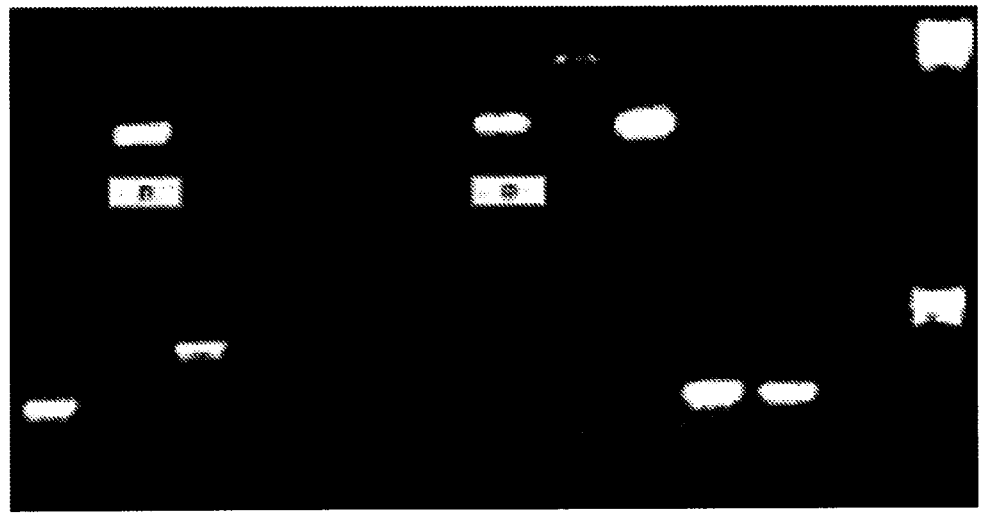
Figure 4F:
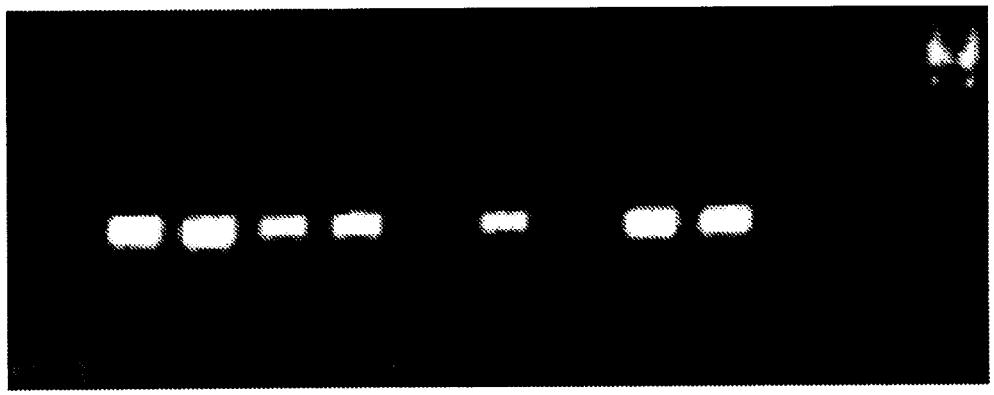

The gene, ibeA, previously identified from RS218 to contribute to invasion of human brain microvascular endothelial cells (HBMEC) in vitro and traversal of the blood brain barrier (BBB) in vivo (64), was also found to be present in strains C5, RS167,11E3034 and E334 by microarray analysis. This was confirmed by PCR analysis, shown in FIG. 4. In FIG. 4, selected genes were examined by PCR to confirm micro array data as follows: FIG. 4A: ibeA; FIG. 4B: cnfl; FIG. 4C: iha; FIG. 4D: fuA; FIG. 4E: hlyE and hlyA; FIG. 4F: iucA. PCR programs for each selected gene were optimized by using the same amount of genomic DNA as template. Microarray data of selected genes (P: present; A: absent; D: divergent) were shown in the bottom of each picture. Cytotoxic necrotizing factor 1 (CNF1) is a 115-kDa protein toxin produced by extraintestinal E. coli strains which include uropathogenic and meningitis-causing E. coli(65). A cnfl mutant had decreased virulence in mouse model of ascending UTI compared to the isogenic cnfl+strain (66). Previously, CNF1 has been shown to be a virulence factor contributing to E. coli K1 invasion of HBMEC in vitro and traversal of the BBB in vivo (116). Cnfl was found to be present only in 2 of the 11 strains (C5 and RS218) by both micro array and PCR analysis (as shown in 4B). Iron-regulated gene homologue adhesin (iha), an E. coli 0157:H7 outer membrane protein was shown to confer the adherence phenotype upon non-adherent laboratory E. coli and shown to be a virulence factor in uropathogenic E. coli (114). The iha gene encodes a 67 kDa protein in E. coli 0157:H7 similar to iron-regulated gene A (IrgA) of Vibrio cholera (22). Microarray and PCR analysis showed that iha is present in all group 2 strains (ECI0, RS168, E253) and only in one group 1 strain E334 (FIG. 4C). The yersiniabactin receptor (fuA) gene was the most highly prevalent iron utilization system in enteroaggregative E. coli (EAEC) and avian pathogenic E. coli (APEC) (19, 53). The fuA gene was found to be uniformly present in all 11 representative strains by micro array analysis, which was confirmed by PCR (FIG. 4D). The iuc (iron uptake chelate) gene locus encodes enzymes necessary for synthesis of the siderophore aerobactin, whereas the iutA (iron uptake transport) gene product represents the TonB dependent outer-membrane receptor for ferrcaerobactin. The first step in aerobactin synthesis is hydroxylation of L-lysine by IucD, whereas IucB is responsible for acetylation of N-hydroxylysine. Two N-acetyl-N-hydroxylysine molecules are then attached to the carboxylic groups of citric acid by IucC and probably IucA, resulting in aerobactin. The iuc was shown to be present in all strains, except for strains C5, RS167, 11E3034 and RS218, and PCR verified the micro array data (FIG. 4F). However, iutA is present in all group 2 strains (ECI0, RS168 and E253) and one group 1 strain E334. Hemolysin production was described in approximately 23% of the E. coli strains associated with neonatal meningitis (43), and the microarray data showed the presence of hlyABCD in strains C5, E334 and RS218, but not in others, as shown in Table 1. PCR analysis of hlyA also confirmed the microarray result, but revealed a different amplification product (about 1 kb compared with expected 550 bp product) in strain S88 (FIG. 4E). This 1 kb band from strain S88 was sequenced, and BLAS showed it is similar to ORF Z1789 (0157 EDL933), which encodes a putative ARC-type regulatory protein. The distribution of hlyE is completely different from that of hlyABCD. Only group 2 strains ECIO and RS168 showed the potential presence of hlyE by micro array analysis, as shown in Table 1, above. However, PCR and sequencing analysis showed that all group 2 strains (ECIO, RS168 and E253) harbor hlyE (FIG. 4E). These differences might be related to an oligo design problem from MWG (High Point, N.C.).

Lipoprotein

Lipoprotein is a major component of the outer membrane of Enterobacteriaceae. Lipoprotein induces pro inflammatory cytokine production in macrophages and lethal shock in LPS-responsive and non-responsive mice (67). Bacterial lipoproteins comprise a unique set of proteins modified at their amino-teIDinal cysteines by the addition of N-acyl and S-diacyl glyceryl groups (67). In E. coli, this lipid serves to anchor these proteins to the inner or outer membrane so that they can function at the lipid aqueous interface. These proteins can be identified by the presence of a leader with a common consensus sequence (9). The leader is typically between 15 and 40 amino acid residues in length and has at least one arginine or lysine in the first seven residues. The leader is cleaved by signal peptidase II on the amino teIDinal side of the cysteine residue, which is then enzymatically modified (67). The data revealed that about 100 lipoproteins are present in E. coli K-12 (46). 54 ORFs that encode lipoproteins or putative lipoproteins were printed on the microarray, and about half of them (20 of 54) are shown to be present in all representative strains of E. coli K1, as shown in Table 2 that follows.

TABLE 2

| ORFs | Function | Presence of ORFs in strains | | | | | | | | | | |
|------|----------|------|----|--------|-----|-----|-----|-------|------|------|-------|------|
| | | RS215 | C5 | IHE3034 | S89 | S95 | A90 | RS187 | E334 | EC10 | RS165 | E253 |
| ace24 | Hypothetical lipoprotein | + | + | + | + | + | + | + | + | − | − | +/− |
| apbE | Putative thiamine biosynthasis lipoprotein | + | + | + | + | + | + | + | + | + | + | + |
| blc | Outer membrane lipoprotein (lipocalin) | + | + | + | + | + | + | + | + | + | + | + |
| outF | Outer membrane lipoprotein | + | + | + | + | + | + | + | + | + | + | + |
| hmsF | Putative lipoprotein | + | + | + | + | + | + | + | + | + | − | + |
| lgt | Phosphatidylglyceri-prolipoprotein diacylglyceryl transferase | + | + | + | + | + | + | + | + | + | + | + |
| int | Apolipoprotein N-acytransferase | + | + | + | + | + | + | + | + | + | + | + |
| iolA | Outer membrane lipoprotein | + | + | + | + | + | + | + | + | + | + | + |
| ipp | Murgin lipoprotein | + | + | + | + | + | + | + | + | + | + | +/− |
| nipB | Lipoprotein-34 | + | + | + | + | + | + | + | + | + | + | + |
| nipC | Lipoprotein | + | + | + | + | + | + | + | + | + | + | + |
| nipD | Lipoprotein | + | + | + | + | + | + | + | + | + | + | + |
| nipl | Lipoprotein | + | + | + | + | + | + | + | + | + | + | + |
| ormB | Lipoprotein osmoticaly inducesis | + | + | + | + | + | + | + | + | + | + | + |
| ripAB | Minor lipoprotein | + | + | + | + | + | + | + | + | + | + | + |
| slyB | Putative outer membranes lipoprotein | + | + | + | + | + | + | + | + | + | + | + |
| spr | Suppressed thermosensitivity of try mutants at low osmodensity | + | + | + | + | + | + | + | + | + | + | + |
| racJ | Lipoprotein precursor | + | + | + | + | + | + | + | + | + | + | + |
| yaiL | Putative lipoprotein | + | + | + | + | + | + | + | + | + | + | + |
| yajG | Putative lipoprotein | + | + | +/− | +/− | +/− | + | + | +/− | +/− | +/− | +/− |
| yenR | Putative lipoprotein | + | + | + | + | + | + | + | + | + | + | + |
| yfiO | Putative lipoprotein with tatraticpeptide repeat (TPR) domain | + | + | + | + | + | + | + | + | + | + | + |
| yqnH | Putative Outer membrane lipoprotein | + | + | + | + | + | + | + | + | + | + | + |
| yhiU | Multidrug maintance protein | +/− | + | + | + | + | + | + | +/− | +/− | +/− | +/− | a only microarray date are given; not PCR confirmation results.
b "+" means present; "−" means absent, "+/−" means divergent.

For example, cutF (nlpE) encoding an outer membrane lipoprotein is involved in copper transport in *E. coli*, and a mutation of cutF results in an increased copper sensitivity in *E. coli* (28). CutF is shown to be present in all *E. coli* K1 strains. RlpA and rlpB encoding two lipoproteins are located in the leuS-dacA region (15 min) on the *E. coli* chromosome (63). A truncated rlpA gene in *E. coli* was able to rescue a conditionally lethal mutation in the prc gene (involved in C-terminal processing of penicillin-binding protein-3) (5). The prc mutants are sensitive to heat and osmotic stress (29). RipA is shown to be present in all *E. coli* K1 strains, as shown in Table 2. LoICDE, an ATP-binding cassette (ABC) transporter, releases outer membrane-specific lipoproteins from the inner membrane to form a complex between the released lipoproteins and the periplasmic molecular chaperone LoIA (51). LoIA was shown to release other outer membrane lipoproteins such as PaI, NIpB, SIp and RIA, whereas inner membrane lipoproteins AcrA and NIpA were not released even in the presence of LoIA (69), indicating that LoIA plays a critical role in the sorting of lipoproteins. LoIA is shown to be present in all 11 *E. coli* K1 strains (Table 2). An outer membrane lipoprotein encoded by nlpI may be important for the process of cell division in *E. coli* K-12 and has been shown to be involved in adherence to and invasion of intestinal epithelial cells by *E. coli* strain LF82 (4, 52). This nlpI is also found to be present in all the 11 *E. coli* K1 strains (Table 4). Interestingly, aec24 encoding a hypothetical lipoprotein is shown to be present in group 1 strains, but absent in group 2 strains.

Protease

Proteases were shown to be present in many pathogenic bacteria, where they play critical functions related to colonization and evasion of host immune defenses, or tissue damage during infection (47, 65). Proteolysis in *E. coli* serves to rid the cell of abnormal and misfolded proteins and to limit the time and amounts of availability of critical regulatory proteins. Most intracellular proteolysis is initiated by energy-dependent proteases, including Lon, ClpXP, and HflB (24). Oligos which represent 137 proteases were printed on the microarray. Approximately 70 percent of them (102 of 137) are shown to be present in all 11 representative strains. For the remaining proteases, some ORFs exhibit non-random distribution among representative strains. Of interest, vat. 2 encoding hemoglobin protease (55) is present in all strains in group 1, but absent from group 2 strains, as shown below in Table 3. Similarly, yeaZ encoding a putative glycoprotein endopeptidase is absent only in strains group 2 strains ECIO and RS168 (Table 3). The gene sohA encoding a putative protease, allows temperature-sensitive htrA mutant *E. coli* to grow at 42 (3). Microarray showed sohA is present in all group 2 strains and one strain RS167 from group 1 (Table 3).

TABLE 3

| ORFs | Function | Presence of ORFs in strains | | | | | | | | | | |
|---|---|---|---|---|---|---|---|---|---|---|---|---|
| | | RS215 | C5 | IHE3034 | S89 | S95 | A90 | RS187 | E334 | EC10 | RS165 | E253 |
| ampE | Putative transmembrane protein, putative protease | + | + | + | + | + | + | + | + | + | + | + |
| elpA | Serine protinase | + | + | + | + | + | + | + | + | + | + | + |
| degQ | Serine endoprotinase | + | + | + | + | + | + | + | + | + | + | + |
| degS | Periplasmic serine endoprotase | + | + | + | + | + | + | + | + | + | + | + |
| extE | Membrane-associated protease | + | + | + | + | + | + | + | + | + | + | + |
| envC | Periplasmic protease | + | + | | + | + | + | + | + | + | + | + |
| gcp | Putative O-singlycoprotein endopeptidase | + | + | + | + | + | + | + | + | + | + | + |
| hftB | ATP-dependant zinc metallo-protease | + | + | + | + | + | + | + | + | + | + | + |
| hsfU | ATPase component of the HsIUV protease | + | + | + | + | + | + | + | + | + | + | + |
| htrA | Periplasmic serine protease | + | + | + | + | + | + | + | + | + | + | + |
| hycI | Protense involved in processing C-terminal end of HycE | + | + | + | + | + | + | + | + | + | + | + |
| lap | Aminopeptidase in alkaline phosphatase isozyme conversion | + | + | + | + | + | + | + | + | + | + | + |
| lcpB | single peptidase I | +/− | +/− | +/− | +/− | +/− | − | − | +/− | +/− | +/− | − |
| lexA | Transcriptional repressor for SOS response (signal peptidase of LexA family) | + | + | + | + | + | + | + | + | + | + | + |
| lon | DNA-binding ATP-dependent protease La | + | + | + | + | + | + | + | + | − | − | + |
| lxpA | Prolipoprotein signal peptidase (SPase II) | + | + | + | + | + | + | + | + | + | + | + |
| map | Methionine aminopeptidase | + | + | + | + | + | + | + | + | + | + | + |
| mapA | Murein DD-endopeptidase | + | + | + | + | + | + | + | + | + | + | + |
| ampX | Outer membrane protease, receptor for phage OX2 | + | + | + | + | + | + | + | + | + | + | + |
| pbpG | D-Alanyl-D-alanine endopeptidase | + | + | + | + | + | + | + | + | + | + | + |
| pepA | Aminopeptidase A | + | + | + | + | + | + | + | + | + | + | + |
| prc | Carboxy-terminal protease | + | + | + | +/− | + | + | + | + | + | + | + |
| ptrA | Protease III | + | + | + | + | + | + | + | + | + | + | + |
| ptrS | Protease II | + | + | + | + | + | + | + | + | + | + | + |
| radA | Putative ATP-dependent protease | + | + | + | + | + | + | + | + | + | + | + |
| racA | DNA strand exchange and recombination protein with protease and nuclease activity | + | + | + | + | + | + | + | + | − | + | + |
| rcpR | putative prophage lambda endopeptidase | + | + | + | + | + | + | + | + | + | + | + |
| sohA | Putative protease; htrA suppressor protein | − | − | − | − | − | − | + | − | + | + | + |
| sppA | Protease IV, a signal peptide peptidase | + | +/− | +/− | +/− | +/− | +/− | +/− | +/− | + | + | +/− |
| sspB | Stringent starvasion protein B | + | + | + | + | + | + | + | + | + | + | + |
| sapA | protease I | + | + | + | + | + | + | + | + | + | + | + |
| vat.2 | Hemoglobin protease | + | + | + | + | + | + | + | + | − | − | − |
| yeaZ | Putative glycoprotein endopeptidase | + | + | + | + | + | + | + | + | − | − | + |
| yegQ | Putative protease | + | + | + | + | + | + | + | + | + | + | + |
| yghQ | Putative serine protease | + | + | + | + | + | + | + | + | + | + | + |
| yhdU | Putative protease | + | + | + | + | + | + | + | + | + | + | + |
| yhbV | Putative protease | + | + | + | + | + | + | + | + | + | + | + | a only microarray data are given; not PCR confirmation results.
b "+" means present; "−" means absent; "+/−" means divergent.

Outer Membrane Protein

There is increasing evidence that outer membrane proteins contribute to adhesion and invasion of the host cells in several gram-negative organisms. For example, outer membrane protein A (OmpA), a highly conserved protein in E. coli, was shown to contribute to E. coli K1 invasion of HBMEC and penetration into the central nervous system (66). 143 oligos which represent outer membrane proteins and outer membrane protein related proteins were printed onto the micro array. Microarray data showed that many outer membrane proteins were absent in group 1 (strains RS218, 11E3034, C5, RS167, A90, S88, S95 and E334), but present in group 2 (strains EC10, E253 and RS168) (Table 4). For example, ycbS encoding a putative outer membrane protein, yejO encoding a putative outer membrane protein with pectin lyase-like domain and yiaT encoding a putative outer membrane protein are present in all strains of group 2 but absent in group 1 strains. Similarly, sfmD encoding a putative outer membrane protein is present in all strains of group 2 but absent in group 1 strains. In contrast, some other outer membrane proteins are present only in group 1 strains. For example, bglH encoding a carbohydrate-specific outer membrane porin is one gene of bgl operon, which is responsible for uptake and fermentation of β-glucosides in E. coli (1). The results showed that bglH is present in all group 1 strains, but absent in group 2 strains except for strain E253 (Table 4).

TABLE 4

| ORFs | Function | Presence of ORFs in strains | | | | | | | | | | |
|------|----------|-------|----|--------|-----|-----|-----|-------|------|------|-------|------|
| | | RS218 | C5 | IHE3034 | S88 | S95 | A90 | RS167 | E334 | EC10 | RS168 | E253 |
| bglH | Carbohydrate-specific outer membrane porin in cyptic operon | + | + | + | + | + | + | + | + | − | − | + |
| btuB | Cobalamin transport, receptor for E colicine | + | + | + | + | + | + | + | + | + | + | + |
| cirA | Receptor for colicin I | + | + | + | + | + | + | + | + | + | + | + |
| saeH | Putativer outer membrane protein Important for attachment to cell | + | +/− | +/− | +/− | +/− | +/− | +/− | +/− | + | + | + |
| fadL | Transport of long-chain fatty acids | + | + | + | + | + | + | + | + | + | + | + |
| lecA | Receptor for ferric citrate | − | − | − | + | + | + | − | − | + | + | + |
| lepA | Receptor for ferric emrobactin and collcins B and D | + | + | + | + | + | + | + | + | + | + | + |
| transH | Putativer outer membrane protein | + | + | + | + | + | + | + | + | + | − | + |
| ntrA | Bacteriophage N4 receptor | +/− | − | − | − | − | − | + | + | + | + | + |
| nmpC | NmpC precursor | + | + | + | + | + | + | + | + | + | + | + |
| ompA | Outer membrane pore protein 3a | + | + | + | + | + | + | + | + | + | + | + |
| ompC | Outer membrane pore protein 1b | + | + | + | + | + | + | + | + | + | + | + |
| ompF | Outer membrane pore protein 1a | + | + | + | + | + | + | + | + | + | + | + |
| ompG | Outer membrane pore protein | + | + | + | + | + | + | + | + | + | + | + |
| ompN | Outer membrane pore protein N | + | + | + | + | + | + | + | + | + | + | + |
| ompT | Prolease VII, outer membrane protein 3b (a), putative porin | + | + | + | + | + | + | + | + | + | + | − |
| ompW | Colcin S4 receptor | + | + | + | + | + | + | + | + | + | + | + |
| pldA | Outer membrane phospholipase A | + | + | + | + | + | + | + | + | + | + | + |
| sfmD | Putative outer membrane protein | − | − | − | − | − | − | − | − | + | + | + |
| sip | Outer membrane protein, induced after carbon starvation | + | +/− | + | + | + | + | + | +/− | + | + | + |
| yaeT | Putative outer membrane antigen | +/− | +/− | +/− | +/− | +/− | +/− | +/− | + | +/− | +/− | + |
| yalV | Putative outer membrane protein with cAMP-binding domain | + | + | + | + | + | + | + | + | + | + | + |
| ybiL | Putative ferrisiderophore receptor | + | + | + | + | + | + | + | + | + | + | + |
| yobS | Putative outer membrane protein | − | − | − | − | − | − | − | − | + | + | + |
| ydeT | Putative outer membrane protein | − | + | + | − | + | + | + | +/− | + | + | − |
| yehB | Putative outer membrane protein | + | +/− | +/− | +/− | +/− | +/− | +/− | +/− | +/− | +/− | + |
| yejO | Putative outer membrane protein with pactin lysase-like domain | − | − | − | − | − | − | − | +/− | + | + | + |
| yflB | Putative outer membrane protein | + | + | + | + | + | + | + | + | + | + | + |
| yiaD | Putative outer membrane protein | + | + | + | + | + | + | + | + | + | + | + |
| yiaT | Putative outer membrane protein | − | − | − | − | − | − | − | +/− | + | + | + |
| ylcP | Putative outer membrane protein | + | + | + | + | + | + | + | + | + | + | + |
| yjhA | Conserved hypothetical protein, outer membrane domain | + | + | + | + | + | + | + | + | + | + | + |
| yjiK | Putative outer membrane protein | + | + | + | +/− | +/− | + | + | + | + | + | + |
| yncD | Putative outer membrane porin protein | + | + | + | + | + | + | + | + | + | + | + |
| yohG | Putative outer membrane protein | + | + | + | + | + | + | + | + | + | + | + |
| ypjA | Putative outer membrane protein with protein lysase-like domain | + | + | + | + | + | + | + | + | + | + | + |
| yitM | Putative outer membrane protein | + | + | + | + | + | + | + | + | + | + | + | a only microarray data are given, not PCR confirmation results.
b "+" means present; "−" means absens; "+/−" means divergent.

Secretion System

General secretory pathway (GSP) systems, which can export the majority of bacterial exoenzymes and toxins, have been identified in many gram negative bacteria, such as H. influenzae, V. cholerae, uropathogenic E. coli, and H. pylori (56, 60). Secretion by the GSP has been shown to play an important role in bacterial pathogenesis. For example, many virulence factors including extracellular toxins; pili, curli, adhesins, invasins, and proteases are exported to the extracellular environment via the GSP (62). The microarray data showed the presence of GSP operon (13 ORFs) in all group 1 strains, but not in group 2 strains except for strain E253. Table 5, shown below, summarizes the results.

TABLE 5

| | RS218 | C5 | IHE3034 | S88 | S95 | A90 | RS167 | E334 | EC10 | RS168 | E253 |
|---|---|---|---|---|---|---|---|---|---|---|---|
| sep[a] | − | − | − | − | − | − | − | − | − | − | − |
| esc[a] | − | − | − | − | − | − | − | − | − | − | − |
| epr[a] | − | − | − | − | − | − | − | − | + | + | + |
| epa[b] | − | − | − | − | − | − | − | − | + | + | + |
| eiv[b] | − | − | − | − | − | − | − | − | + | − | − |
| GSP[b,c] | + | + | + | + | + | + | + | + | − | − | + |

[a] PCR confirmation results.
[b] including all 13 ORFs of the GSP operon,
[c] only microarray data are given, not PCR confirmation results.
"+" means present;
"−" means absent.

Type III secretion systems allow *Yersinia* spp., *Salmonella* spp., *Shigella* spp., *P. aeruginosa* and enteropathogenic *E. coli* to adhere to the surface of eukarotic cells by injecting bacterial proteins across the two bacterial membranes and the eukaryotic cell membrane to destroy or subvert the target cell (11, 45). These systems consist of a secretion apparatus, made of approximately 25 proteins, and an array of proteins released by this apparatus. Some of these released proteins are "effectors," which are delivered into the cytosol of the target cell, whereas the others are "translocators," which help the effectors cross the membrane of the eukaryotic cell. Most of the effectors act on the cytoskeleton or on intracellular signaling cascades (12). A protein injected by the enteropathogenic *E. coli* serves as a membrane receptor for the docking of the bacterium itself at the surface of the cell (23). Interestingly, by using comparative genomic hybridization, it was found that all group 2 strains harbor type III secretion system locus, as shown in Table 5. This locus contains ORFs whose amino acid sequences show high degrees of similarity with those of the proteins that make up the type III secretion apparatus of the inv-spa-prg locus on a *Salmonella* SPI-1 pathogenicity island (61). This locus was designated ETT2 (*E. coli* type III secretion 2) and consisted of the epr, epa, and eiv genes. ETT2 was found in enteropathogenic *E. coli* and some non-O157 Shiga toxin producing *E. coli* (STEC) strains, but most of them contained a truncated portion of ETT2 (30). Strains RS168 and E253 harbor a part of ETT2 (epr and epa operon), but lack eiv genes. However, strain EC10 was found to harbor all the genes needed to encode type III secretion apparatus proteins. This is the first demonstration that type III secretion system is found to be present in *E. coli* K1 strains isolated from CSF.

Example 3

Identification and Annotation of *E. coli* RS218-Derived Islands (RDI)

Genome sequencing of the most common prototype *E. coli* K1 strain for bacteremia and meningitis, strain RS 218 (O18: K1:H7) provides new tools for identifying microbial determinants contributing to *E. coli* bacteremia such as comparative genomics and microbial DNA microarrays. As described herein, a comparative analysis of *E. coli* RS 218 genome was carried out and 22 *E. coli* RS 218-specific genomic islands that are larger than 10 kb and absent in laboratory *E. coli* K-12 strain MG 1655 were identified.

The presence and boundaries of *E. coli* RS 218-specific islands were determined with sequence alignment between published *E. coli* MG1655 genome and the sequence of *E. coli* RS 218. The island length cutoff was set as 10 kilobases, which subsequently generates 22 *E. coli* RS 218-specific sequence segments. These 22 *E. coli* RS 218-derived islands were termed RDIs. Prediction of open reading frames (ORFs) inside each island was conducted with a prokaryotic gene finder, EasyGene (109). Combining query results from InterPro and Genbank, each predicted ORF was assigned to the putative functions. The locations and size of RDIs relative to MG1655 are illustrated in FIG. 1.

Based on island boundary determined from genomic sequence comparison, RDI deletion mutants were constructed using markerless gene deletion method (110, 111) for RDI 21 and RDI 22, or one-step PCR gene inactivation method (112-115, 133) for the remaining RDIs. Deletions were confirmed by PCR and sequencing of PCR products. It is important to note that all of RDI-associated tRNAs were maintained intact in corresponding RDI deletion mutants. Deletion mutants were similar to the parent strain RS 218 regarding their growth kinetics in LB broth and their survival abilities in stationary phase.

Using RDI deletion mutants, it was found that four mutants deleted of RDIs 4, 7, 16, and 21 are defective in inducing a high-degree of bacteremia. RDI 16 encodes the genes responsible for the K1 capsule, which is a known determinant in *E. coli* RS 218 contributing to its survival in the bloodstream. The failure of RDI 16 deletion mutant was related to the loss of the K1 capsule. RDI 21 deletion resulted in increased expression of type 1 fimbriation, which was shown to be responsible for the lower degree of bacteremia with RDI 21 mutant (134, 135). A possibility is that the remaining two RDIs (4 and 7) contain novel microbial determinants contributing to *E. coli* bacteremia. In addition, RDIs 4 and 7 are shown to be prevalent (80-100%) in representative *E. coli* K1 strains possessing serotypes common in patients with bacteremia (e.g., O18:K1, O7:K1, O1:K1, O16:K1, and O12:K1).

Based on the genomic sequence alignment with *E. coli* MG1655, 22 genomic islands were identified that were present in meningitis-causing *E. coli* RS218, but absent in non-pathogenic *E. coli* MG1655 genome. Table 6a and Table 6b, shown below, are summaries of sizes of *E. coli* RS218-derived islands (RDI) and their distributions in other *E. coli* and related bacteria. The total length of these RS218-derived islands (RDI) was about 793 kb, which replaced about 80 kb of MG1655 specific sequences, resulting in approximately 713 kb larger chromosome size in RS218. This difference was 160 kb larger than the previously estimated genomic size difference between RS218 and MG1655 (~556 kb) (13). The strains included in genome comparison are *E. coli* strain CFT073, strain EDL933 and strain Sakai, *S. enterica* serovar Typhi strain Ty2 and strain CT18, *Y. pestis* strain KIM and strain CO92, and *Shigella flexneri* 2a strain 2457T and strain 301. As shown in Table 6a and 6b, the average of GC percentage (GC %) in *E. coli* RS218 genome is 50.63%. In the Table, '−' and '+' indicate absence and presence in the genome, respectively. '±' indicates that although the island is present in the genome, it contains large DNA segment insertions, deletions, or substitutions that are different from E. coli RS218. Table 6a is shown below.

TABLE 6a

| Islands | Size (kb) | Anchor tRNA | GC %[a] | Present in E. coli and related genomes[b,c] |
|---|---|---|---|---|
| RDI 1 | 28.9 | aspV | 51.52 | ±E. coli EDL933 and Sakai, ±Y. pestis KIM and CO92 |
| RDI 2 | 33.9 | | 51.05 | ±E. coli CFT073, ±S. enterica serovar Typhi Ty2 and CT18 |
| RDI 3 | 10.0 | | 49.73 | ±Y. pestis KIM and CO92 |
| RDI 4 | 61.7 | serX | 48.07 | ±E. coli CFT073 |
| RDI 5 | 47.4 | | 49.79 | ±E. coli CFT073 |
| RDI 6 | 46.9 | | 51.39 | ±E. coli CFT073, ±E. coli EDL933 and Sakai |
| RDI 7 | 14.9 | | 41.91 | – |
| RDI 8 | 38.0 | | 54.07 | ±S. enterica serovar Typhi Ty2 and strain CT18 |
| RDI 9 | 31.5 | asnT | 57.64 | +E. coli CFT073, +Y. pestis KIM and CO92 |
| RDI 10 | 54.4 | asnW | 53.07 | +E. coli CFT073 |
| RDI 11 | 42.4 | | 49.25 | +E. coli CFT073 |
| RDI 12 | 38.8 | argW | 46.83 | – |
| RDI 13 | 12.1 | | 50.49 | +E. coli CFT073 |
| RDI 14 | 43.7 | | 49.27 | – |
| RDI 15 | 36.2 | metZ | 50.13 | ±E. coli CFT073 |
| RDI 16 | 27.7 | pheV | 45.68 | ±E. coli CFT073 |
| RDI 17 | 16.1 | | 48.57 | +E. coli CFT073 |
| RDI 18 | 44.8 | | 50.72 | ±E. coli EDL933 and Sakai |
| RDI 19 | 13.7 | | 49.48 | +E. coli CFT073 |
| RDI 20 | 10.9 | | 48.86 | +E. coli CFT073 |
| RDI 21 | 116.5 | leuX | 46.22 | – |
| RDI 22 | 20.3 | | 46.11 | – |

[a] The average of GC percentage in E. coli RS218 genome is 50.63%.
[b] '–' and '+' indicate absence and presence in the genome, respectively. '±' indicates that although the island is present in the genome, it contains large DNA segment insertions, deletions, or substitutions that are different from E. coli RS218.
[c] The strains included in genome comparison are E. coli strain CFT073, strain EDL933 and strain Sakai, S. enterica serovar Typhi strain Ty2 and strain CT18, Y. pestis strain KIM and strain CO92, and Shigella flexneri 2a strain 2457T and strain 301.

TABLE 6b

| RDI/potential virulence factors | RB 218 (O18:K1) | C5 (O18:K1) | IHE 3034 (O18:K1) | EC 10 (O7:K1) | A90 (O1:K1) | RS 168 (O1:K1) | RS 167 (O16:K1) | E253 (O12:K1) | E 334 (O12:K1) |
|---|---|---|---|---|---|---|---|---|---|
| 4 | + | + | + | – | + | + | + | + | + |
| iroN | + | + | + | – | + | – | + | – | + |
| avf | + | + | + | – | + | + | + | + | + |
| hmuR | + | + | + | – | + | – | + | – | + |
| 7 | + | + | + | + | + | + | + | + | + |
| segment II | + | + | + | + | + | + | + | + | + |

+ or –: Most ORFs (>50%) from respective RDIs are present or absent, respectively (or presence or absence of individual genes or segment II)

As shown in the above Table 6b, RDI 7 is shown to be present in all 9 representative strains of E. coli K1, while RDI 4 is present in 8 strains (approximately 90%). Certain putative virulence factors from RDI 4 and RDI 7 can be potential candidates contributing to bacteremia (e.g., avf from RDI 4 and segment II from RDI 7, as shown in the Tables), and these potential candidates are also shown to be prevalent in representative E. coli K1 strains. These findings suggest that microbial determinants in RDIs 4 and 7 that contribute to bacteremia are likely to be prevalent in E. coli K1 strains isolated from patients with E. coli bacteremia.

Genomic islands are frequently associated with tRNA genes and contain mobility genes coding for integrases or transposases that are required for chromosomal integration and excision (8, 23). Among these 22 identified RDIs, five islands include a P4-family integrase and are directly adjacent to tRNAs (RDI 4-serX, RDI 9-asnT, RDI 10-asnW, RDI 12-argW, and RDI 21-leuX). In addition, three islands (RDI 8, 9, and 10) have higher GC percentages while five others (RDI 7; 12, 16, 21, and 22) have markedly lower GC percentages compared with the whole E. coli RS218 genome. This evidence suggests that these RS218-derived islands are acquired through horizontal gene transfer.

Next, sequence alignment was carried out. Meningitis and urinary tract infection (UTI) are two predominant forms of human extraintestinal E. coli infection. Sequence alignment of 22 RDI with sequence of UTI strain CFT073 genome revealed that seven of them (RDI 9, 10, 11, 13, 17, 19, and 20) were present in CFT073, as shown in Table 2. Six other RDIs (RDI 2, 4, 5, 6, 15, and 16) were also present in CFT073 genome but with insertion, deletion, or substitution of large DNA segments. In addition, these 22 RDIs were aligned with other E. coli and related microbes whose genomes were completely sequenced, such as Salmonella, Yersinia, and Shigella. Seven of the islands (RDI 1, 2, 3, 6, 8, 9, and 18) were also found in intestinal E. coli and other related bacteria. There were five islands (RDI 7, 12, 14, 21, and 22) that were specific to RS218 and absent in other genomes.

A detailed in silico analysis was performed on each predicted CDS located in the islands. Putative functions were assigned to each CDS based on sequence similarity with previously annotated genes. Virulence factor profiles vary among RDIs. Collectively, these virulence factors are comprised of several fimbrial and non-fimbrial adhesins, three types of protein secretion systems, different invasins, modulins, and cytotoxins, five iron acquisition systems, and varieties of other virulence factors. This is shown in Table 7, below, which is a summary of genetic features located in E. coli RS218-derived islands. These genomic islands may enhance the virulence potentials of E. coli RS218 for bacterial infection, for example for meningitis.

TABLE 7

| Functional categories | E. coli RS218-derived islands that harbor these genetic factors |
|---|---|
| Adhesins | Fimbrial adhesins: RDI 4 (S-fimbriae), RDI 7 (Type 1-like fimbriae fim2), RDI 21 (P-fimbriae, F17-like fimbriae) Non-fimbrial adhesins: RDI 4 (antigen 43), RDI 13 (SivH), RDI 21 (Hek, and hemagglutinin) |

TABLE 7-continued

| Functional categories | E. coli RS218-derived islands that harbor these genetic factors |
|---|---|
| Protein secretion systems | RDI 4 (T5SS for antigen 43), RDI 7 (Type II/III secretin), RDI 16 (T2SS), RDI 21 (T1SS for hemolysin) |
| Invasins, modulins, and effectors | RDI 1 (IcmF and IcmH), RDI 21 (CNF1), RDI 22 (IbeA) |
| Toxins | RDI 10 (peptide toxin), RDI 21 (α-hemolysin) |
| Iron uptake systems | RDI 4 (Iro system and hmu system), RDI 5 (Sit system), RDI 9 (Ybt system), RDI 11 (fec-like system) |
| Other virulence factors | RDI 7 (PuvA), RDI 12 (sia operon), RDI 16 (K1 capsule biosynthesis), RDI 20 (hip-like protein) |
| Metabolic genes | RDI 15 (sugar metabolism), RDI 17 (phosphor-sugar metabolism), RDI 19 (C4-dicarboxylate metabolism), RDI 20 (fatty acid metabolism), RDI 21 (D-serine catabolism), RDI 22 (dihydroxyacetone, glycerol, and glyoxylate metabolism) |
| Prophage genes | RDI 2, RDI 5, RDI 6, RDI 7, RDI 8, RDI 12, RDI 14, RDI 18 |

Example 4

Constructions and Characterization of RDI Deletion Mutants

Genomic sequence comparison generates a long list of putative virulence factors. Next, evidence on which of these virulence potentials are relevant to the pathogenesis of *E. coli* meningitis was determined. Based on in silico analysis results, 21 island deletion mutants out of 22 RDIs were constructed. It is noteworthy that all of island-associated anchor tRNAs were maintained intact in the corresponding island deletion mutants, shown previously in Table 6a and b. RDI 6 is an island composed of a CP-933-like cryptic prophage. Despite repetitive attempts, RDI 6 deletion mutants were not successfully created.

RDI deletion mutants were examined for their involvement in pathogenic steps critical to the development of *E. coli* meningitis. These include i) a high degree of bacteremia (i.e., their ability to survive and multiply in the bloodstream in neonatal rats), ii) association with HBMEC (i.e., their ability to bind HBMEC), and invasion of HBMEC (i.e., their ability to invade HBMEC). Attenuation of any of these phenotypes would indicate a direct or indirect involvement of the particular RDI in the pathogenesis of *E. coli* meningitis. Table 8a and 8b and Table 9, shown below, summarize this work. Table 8a and 8b show induction of bacteremia by RDI deletion mutants compared to the wild type *E. coli* RS218. Four island deletion mutants, RDI 4, RDI 7, RDI 16, and RDI 21, summarized in Table 8a, were found to be significantly impaired in the ability to survive in the bloodstream, and failed to cause a high-degree of bacteremia as compared to the wild type RS 218 in 5-day-old rat. Bacteremia in neonatal rats caused by wild type *E. coli* RS218 was 8.10±1.91 log CFU/ml of blood, as shown in Table 8. Further, RDI mutants induced significantly lower bacteremia compared to wild type *E. coli* RS218 (p-value <0.01).

As shown in Table 8a and b, RDI 4 deletion mutant was significantly defective in inducing a high-degree of bacteremia compared to the parent strain RS 218. Several putative virulence factors are located on the RDI4 island, such as S-fimbriae (encoded by sfa operon), iron acquisition system (iro operon), hemin/hemoglobin utilization gene (hmuR) and aidA-43-like virulence factor (avf). Previously it has been shown that sfa operon deletion mutant was not defective in induction of bacteremia compared to the parent strain (99), indicating that S fimbriae do not contribute to a high-degree of bacteremia.

TABLE 8a

| Strains | logCFU/ml of blood (mean ± SD)[a] | Potential virulence factors inside the island |
|---|---|---|
| ΔRDI 4 | 5.01 ± 1.11[b] | iro, hmuR, sfa, ag43 |
| ΔRDI 7 | 5.27 ± 2.31[b] | fim2, puvA, secretin |
| ΔRDI 16 | 2.10 ± 0.81[b] | kps, neu, gsp2 |
| ΔRDI 21 | <1.69[b,c] | hek, pap, F17-like fimbriae, cnf1, hly, hecA, dsd |

[a] Bacteremia in neonatal rats caused by wild type *E. coli* RS218 was 8.10 ± 1.91 logCFU/ml of blood.
[b] RDI mutants induced significantly lower bacteremia compared to wild type *E. coli* RS218 (p-value < 0.01).
[c] Bacterial counts in the bloodstream of 5-day old rats were below the detection limits.

TABLE 8B

| strains | Bacteremia (log CFU/ml of blood)[1] mean ± SD |
|---|---|
| RS 218 wild type | 8.10 ± 1.91 |
| RDI 1 | 7.46 ± 2.08 |
| RDI 2 | 8.64 ± 0.96 |
| RDI 3 | 7.09 ± 0.90 |
| RDI 4 | 5.01 ± 1.11* |
| RDI 5 | 7.91 ± 1.70 |
| RDI 6 | 8.14 ± 2.20 |
| RDI 7 | 5.27 ± 2.31* |
| RDI 8 | 8.02 + 1.98 |
| RDI 9 | 8.06 ± 1.70 |
| RDI 10 | 8.32 ± 1.07 |
| RDI 11 | 7.84 + 0.95 |
| RDI 12 | 7.36 ± 2.05 |
| RDI 13 | 8.71 ± 1.56 |
| RDI 14 | 8.30 + 1.18 |
| RDI 15 | 7.89 ± 1.31 |
| RDI 16 | 2.10 ± 0.81* |
| RDI 17 | 8.87 + 1.64 |
| RDI 18 | 8.45 + 1.63 |
| RDI 19 | 8.33 ± 2.31 |
| RDI 20 | 7.67 ± 1.42 |
| RDI 21 | <1.69* |
| RDI 22 | 8.12 ± 1.36 |

Table 9 shows HBMEC association and invasion rates of RDI deletion mutants compared to those of wild type *E. coli* RS218. Here, HBMEC-association rate of wild type *E. coli* RS218 was treated as 100%. *E. coli* HB101 was used as a negative control. Table 9 shows that RDI mutants exhibited significantly decreased HBMEC-association rates.

TABLE 9

| Strains | Relative HBMEC association rate % (mean ± SD)[a] | Relative HBMEC invasion rate % (mean ± SD)[c] | Potential virulence factors inside the island |
|---|---|---|---|
| ΔRDI 1 | 197.5 ± 34.6 | 47.5 ± 14.4[d] | icmF, icmH |
| ΔRDI 7 | 38.3 ± 10.2[b] | 35.3 ± 21.0[d] | fim2, puvA, secretin |
| ΔRDI 12 | 52.0 ± 1.4[b] | 146.7 ± 2.5 | siaL, siaO |
| ΔRDI 13 | 65.0 ± 6.8[b] | 59.3 ± 15.4[d] | ratA, sivHI |
| ΔRDI 20 | 41.7 ± 11.9[b] | 51.6 ± 26.6[d] | hip-like protein |
| ΔRDI 22 | 96.0 ± 11.3 | 51.8 ± 19.0[d] | ibeA |

[a]HBMEC-association rate of wild type E. coli RS218 was treated as 100%. E. coli HB101 was used as a negative control.
[b]RDI mutants exhibited significantly decreased HBMEC-association rates (adjusted p < 0.05, p-values were adjusted for multiple comparisons with the Benjamini and Hochberg procedure (48)).
[c]HBMEC-invasion rate of E. coli RS218 wild type was treated as 100%. E. coli HB101 was used as a negative control.
[d]RDI mutants exhibited significantly decreased HBMEC-invasion rates (adjusted p < 0.05, p-values were adjusted for multiple comparisons with the Benjamini and Hochberg procedure (48)).

The growth characteristics of these RDI mutants were also evaluated. The growth rates of all mutants were comparable to wild type E. coli RS218, except for the RDI 7 deletion mutant. The RDI 7 deletion mutant had a slow growth compared to the parental strain. The doubling time of this mutant is 55 minutes in static BHI broth at 37° C., compared to 32 minutes of E. coli RS218. Interestingly, this mutant is also defective in bacteremia induction and HBMEC association and invasion, as shown in Table 8 and Table 9. RDI 7 is located at terminus of E. coli genome and composed of a truncated fimbriae-like gene cluster and a filamentous prophage CUS-1 (24). It is unclear whether the slow growth of RDI 7 mutant is correlated with its other defects. Additional studies are required to elucidate the molecular basis of those defects associated with RDI 7 mutant.

Example 5

RDIs Role in Induction of Bacteremia

As detailed in Table 8 (a and b) above, four island deletion mutants, RDI 4, 7, 16, and 21 mutants exhibited impaired abilities to induce a high-degree bacteremia in 5-day old rats. Wild type E. coli RS218 caused bacteremia of approximately $10^8$ CFU/ml of blood in 5-day old rats 18 hours after subcutaneous injection of $10^6$ CFU. Bacterial counts in the blood of 5-day old rats infected with RDI 4 and 7 deletion mutants were decreased by more than 2 logs. It was shown that RDI 16 and 21 deletion mutants reduced the magnitude of bacteremia by more than 5 logs. In fact, there was no detectable bacteremia in any of the 5-day-old rats infected with RDI 21 deletion mutant.

RDI 4

RDI 4 is similar to a previously identified island in uropathogenic E. coli 536 known as PAI-III$_{536}$ (101). RDI 4 (61.7 kb) is shown to contain several putative virulence factors such as S-fimbriae (encoded by sfa operon) (97-99), iron acquisition system (iro operon) (100), hemin/hemoglobin utilization gene (hmuR) (100a, 101), and AIDA-like virulence factor (avf) (103, 149, 150), but it is unclear whether these microbial determinants contribute to a high-level bacteremia. Previous studies have shown that a single gene deletion of iroN from iro operon in another E. coli 018:K1 strain C5 isolated from the cerebrospinal fluid of a neonate with meningitis displayed a similar degree of reduction in bacteremia in neonatal rats (100), suggesting that iron acquisition operon iro may be responsible for decreased survival in the bloodstream for the RDI 4 deletion mutant. However, it has been found that mutant deleted of aidA-like virulence factor(avf) was defective in inducing a high-degree of bacteremia, similar to the defect of the RDI 4 deletion mutant, while mutant deleted of iroN induced a level of bacteremia similar to that of the parent strain RS218 (see Table 10). The AVF identified from RDI 4 of E. coli RS 218 is homologous to AIDA-I (an adhesin of diffuse-adhering E. coli) and antigen 43 from E: coli K-12 and belongs to an E. coli autotransporter family (102, 103, 149, 150). Based on predicted protein sequence, the AVF of E. coli strain RS 218 has been shown to possess an amino-terminal signal peptide, a passenger domain (or a domain) and a conserved translocator domain (or β domain) (see FIG. 5). The passenger domain (a domain) has been shown to confer the diverse effector function of the various autotransporters (150) and it is possible that a domain of AVF (aavf) is involved in induction of a high-degree of bacteremia. If verified, this is the first demonstration that AVF contributes to E. coli bacteremia.

Figure 5:
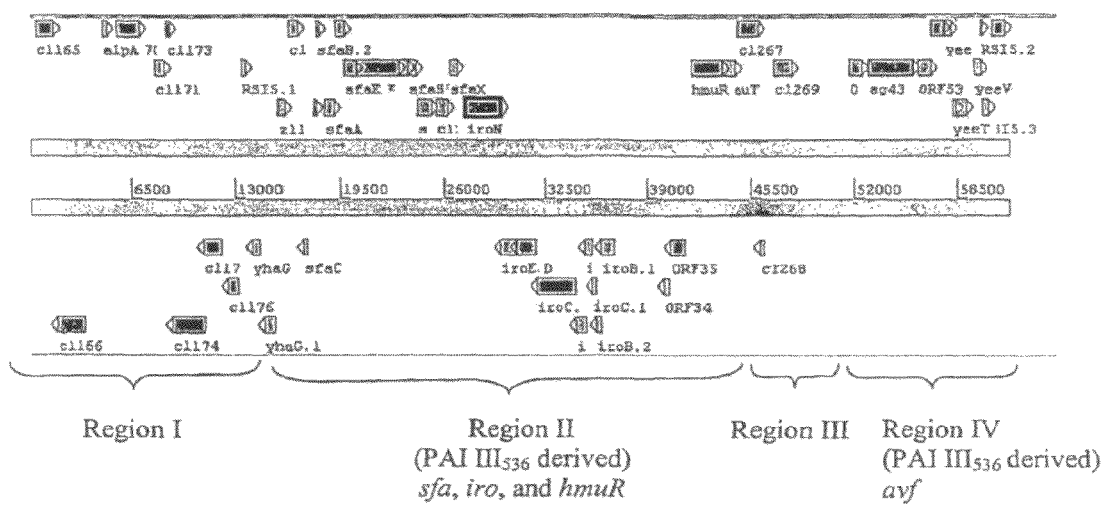
FIG. 5 is a schematic showing characteristics of RDI 4.

Characteristics of RDI 4 are presented in FIG. 5. Previous studies have shown that a single gene deletion of iroN from iro operon in another E. coli 018:K1 strain C5 displayed a similar degree of reduction in bacteremia in neonatal rats (100), suggesting that iroN may be responsible for decreased survival in the bloodstream. Mutants deleted of iroN, hmuR and avf were constructed by the one-step PCR inactivation method, known by one of skill in the art. These deletion mutants were similar to RS 218 and RDI 4 deletion mutant regarding their growth kinetics in LB and BHI broth and their survival abilities in stationary phase. The mutants were examined for their ability to induce a high-level of bacteremia compared to the parent strain RS218 and RDI 4 deletion mutant. Table 10, below, shows comparison of bacteremia among 5 groups of 5-day-old rats receiving RS 218, its RDI 4 deletion mutant or mutants deleted of iroN, avf or hmuR. As shown in Table 10, the mutant deleted of avf is significantly defective in induction of a high-degree of bacteremia, similar to the defect of the ΔRDI 4 mutant, while ΔiroN and ΔhmuR mutants were not significantly defective in induction of a high-degree of bacteremia compared to the parent strain RS218. These findings indicate that AVF is responsible for the defect of RDI 4 to induce a high-degree of bacteremia. This is the first demonstration that AVF contributes to a high-degree of bacteremia.

TABLE 10

| Strains (No. of animals) | Bacteremia (log CFU/ml of blood), mean + SD |
|---|---|
| RS 218 (n = 9) | 9.64 ± 1.13 |
| ΔRDI 4 (n = 13) | 5.36 ± 1.92* |
| ΔiroN (n = 13) | 8.61 ± 1.49 |
| Δavf (n = 11) | 3.04 ± 1.60* |
| ΔhmuR (n = 6) | 8.25 ± 2.34 |

*p < 0.001 compared to RS218, ΔiroN and ΔhmuR.

Figure 6:
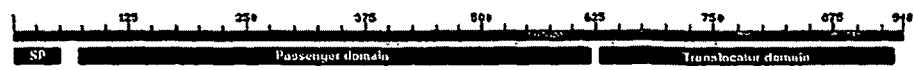
FIG. 6 is a schematic showing the preliminary structure analysis of AVF by BLAST. Signal peptide (SP), passenger and translocator domains are indicated.

The AVF identified from RDI 4 of E. coli RS 218 is homologous to AIDA-I (an adhesin of diffuse-adhering E. coli) and antigen 43 from E. coli K-12 (identities of 88% and 67%, respectively, based on amino acids sequence comparison) and belongs to an E. coli autotransporter family (26, 27, 73, 74). Based on predicted protein sequence, the AVF (termed after aidA-like virulence factor) of E. coli strain RS 218 has been shown to possess an amino-terminal signal peptide, a passenger domain (or a domain) and a conserved translocator domain (or β domain) (FIG. 6). In FIG. 6, the predicted protein sequence of AVF from E. coli strain RS 218 was analyzed using BLAST. Signal peptide (SP), passenger and translocator domains are indicated. The AIDA autotransporter has been shown to exhibit multiple potential roles in bacterial pathogenesis, which include a potential adhesin to different human cell types, bacterial aggregation and biofilm formation (128-130), but none of the autotransporters have been shown to contribute to bacteremia. If verified in this application, this will be the first demonstration of the role of the autotransporters such as AVF in *E. coli* bacteremia.

Figure 7:
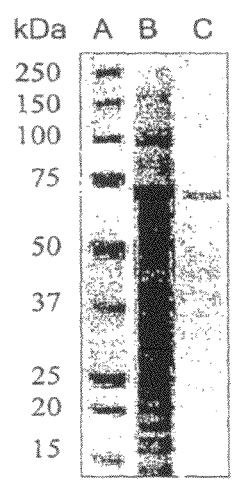
FIG. 7 is an SDS-PAGE gel showing purification of 6His-AVFa ('6His' disclosed as SEQ ID NO: 1. Lanes are as follows: A: Bio-Rad Precision prestained standards (kDa); B: Whole cell lysate induced by 0.1 mM IPTG; C: 6His-AVFa ('6His' disclosed as SEQ ID NO: 1) purified by Ni-NTA (~70KDa).

The passenger domain (α domain) has been shown to confer the diverse effector function of the various autotransporters (150) and it is speculated that a domain of AVF (aavf) is involved in induction of a high-degree of bacteremia. In order to study the role of AVF in *E. coli* bacteremia, an α domain of AVF (aavf) was prepared from RS 218 by the method described previously (121, 122, 124, 128, 129). The PCR amplified fragment encoding a domain of AVF (1.9 kb) using two primers (5'-ATGAAACGACATCTGAACACCAG-3' (SEQ ID NO: 2); 5'-ATATGGCCGGCCCGGAGCCTGC-CAGAATC CG-3' (SEQ ID NO: 3)) was ligated into pQE-80L (Qiagen) to create pQE80-AVFa. The expression of aavf was induced by IPTG in *E. coli* strain DH5a and the protein was purified as described previously (121, 122, 124, 128, 133). Briefly, overnight cultures grown in BHI broth were diluted 1:100 in 1 liter BHI and grown at 37° C. with shaking. IPTG was added at 0.1 mM final concentration at 0.6 of OD600. The bacteria were harvested by centrifugation at 4° C. after 3 hr induction at 30° C. followed by washing in PBS buffer. The pellet was resuspended in 10 ml buffer A (50 mM Tris/HCl pH 8.0, 300 mM NaCl) plus 0.1 mg/ml lysozyme, incubated 30 min on ice, and then lysed by sonication. Insoluble material was removed by centrifugation. The 6His-AVFa ('6His' disclosed as SEQ ID NO: 1) protein was affinity purified from the soluble lysate by overnight incubation at 4° C., with 5 ml Ni-NTA agarose (Qiagen). The lysate was loaded onto the disposable standing columns (Qiagen), each column was washed with 12 ml buffer A and 12 ml buffer B (50 mM Tris/HCl pH 8.0, 300 mM NaCl, 5 mM imidazole). Bound protein was eluted with 10 ml buffer C (50 mM Tris/HCl pH 8.0, 150 mM NaCl, 300 mM imidazole) and collected in 10 1 ml-fractions. 25 μl of each fraction was run on a 4-12% gradient SDS-PAGE gel, and fractions containing 6His-aavf ('6His' disclosed as SEQ ID NO: 1 were pooled, dialyzed against buffer E (10 mM Tris/HCl pH 8.0, 10 mM NaCl) using Slide-A-Lyzer dialysis cassettes (Pierce), and concentrated to 0.5 mg/ml with a Centricon YM-10 centrifugal concentrator (Millipore). Finally, the purified proteins were visualized on the 4-12% gradient SDS-PAGE gel stained by Coomassie Bright Blue. The results are shown in FIG. 7, lane C. FIG. 7 shows SDS-PAGE of purification of 6His-AVFa ('6His' disclosed as SEQ ID NO: 1). Additionally, purified aavf of AVF (about 5 mg from 1 liter-induced culture) will be used for generation of antibody in rabbits via commercial source.

RDI 7

Figure 8:
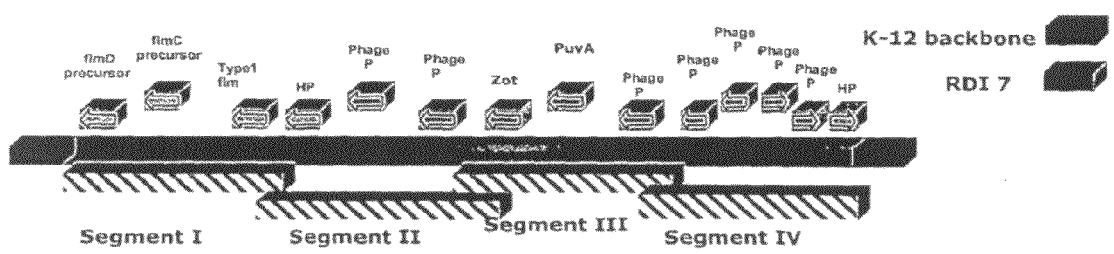
FIG. 8 is a schematic showing characteristics of RDI 7.

RDI 7 deletion mutant exhibited a significant defect in inducing a high-degree of bacteremia compared to the parent strain RS 218. RDI 7 is composed of a mosaic construct of *E. coli* CFT073 segment and a filamentous prophage CUS-1 (104). The left-hand CFT073 segment is composed of type 1 fimbriae-like genes that are extended into the backbone of *E. coli* K-12. On the right-hand side, prophage CUS-1 was integrated into dif locus and appears to be active in *E. coli* RS 218 (104). This filamentous prophage contains putative virulence factors such as puvA, zot, and several phage-related proteins (FIG. 8). FIG. 8 shows that RDI 7 is arbitrarily divided into four segments based on annotations. HP: hypothetical protein. P: protein. puvA was shown to be important for *E. coli* strain RS 218's survival in infant rat's spleen following intraperitoneal administration (105) and it may contribute to decreased magnitude of bacteremia with RDI 7 deletion mutant. However, it is likely that the inability of RDI 7 deletion mutant to induce a high-level of bacteremia is not related to the loss of puvA (Table 11, below). Table 11 shows a comparison of bacteremia among 6 groups of 5-day-old rats receiving strain RS 218. RDI 7 deletion mutant or mutants deleted of one of the four segments of RDI 7. RDI 7 was arbitrarily divided into four overlapping segments, as shown in FIG. 8. Deletions of individual segments were made by the one-step PCR method and deletion mutants were examined for their involvement in the induction of a high-degree of bacteremia, as previously described.

TABLE 11

| Strains (No. of animals) | Bacteremia (log CFU/ml of blood), mean ± SD |
|---|---|
| RS 218 (n = 7) | 8.59 ± 1.14 |
| Δ RDI 7 (n = 7) | 5.74 ± 2.01[a] |
| Δ segment I (n = 8) | 7.82 ± 2.06 |
| Δ segment II (n = 8) | 5.08 ± 1.50[a] |
| Δ segment III (n = 8) | 8.53 ± 0.93 |
| Δ segment IV (n = 8) | 8.09 ± 1.33 |

[a]Significantly less than RS 218 ($p < 0.05$). Experimental details are identical to those of Table 1

As shown in Table 11, deletion mutant of segment II is similar to that of RDI 7 in the inability to achieve a high-degree of bacteremia. These results differ from those of others (105) where puvA in segment III was shown to be important for *E. coli* RS 218's survival in infant rat's spleen. The potential targets in segment II will be identified to determine how RDI 7 deletion mutant is defective in induction of a high-degree bacteremia.

RDI 16

RDI 16 encodes the genes required for sialic acid biosynthesis (neu operon), polysialic acid assembly and exportation (kps operons), and a type II secretion system (gsp2 operon). The expressions of neu operon and kps operons are responsible for the K1 capsule biosynthesis. The K1 capsule is well known for its role in protecting bacteria from serum- and PMN-mediated killing (106). The degree of bacteremia caused by RDI 16 deletion mutant was consistent with previous reports using K1 capsule-negative *E. coli* (99), indicating that impaired ability of RDI 16 mutant to induce a high-degree of bacteremia is related to loss of the K1 capsule.

RDI 21

RDI 21 deletion mutant was shown to be defective in induction of a high-degree of bacteremia in neonatal rats. RDI 21 was the largest island (approx 117 kb) in *E. coli* K1 strain RS 218. Deletion of RDI 21, the largest genomic island detected in *E. coli* RS218, resulted in a most striking reduction in bacterial counts in the blood of neonatal rats. RDI 21 is located near leuX locus and is a mosaic construct of UTI strain *E. coli* 536 PAI-I, PAI-II, and RS218-derived DNA segments (107). Based on the insertion locus leuX and virulence factor profiles (i.e. presence of hek, pap, hly, and cnf1), RDI 21 is probably similar to previously described genetic island PAI-I$_{C5}$, although RDI 21 is about 20 kb larger in size (108). Spontaneous deletion of PAI-I$_{C5}$ in strain C5 resulted in a decreased magnitude of bacteremia (108). Recently, RDI 21 deletion mutant was found to be a type 1 fimbrial molecular switch locked-ON mutant due to constitutive expression of HbiF invertase (Y. Xie, Y. Yao, V. Kolisnychenko, C. Teng, K. S. Kim, Infect Immun 74:4039-4047, 2006). HbiF-dependent type 1 fimbriation was responsible for the failure of this mutant to induce bacteremia in infant rats.

In order to determine the microbial structures in RDI 21 that contribute to bacteremia, microarray analysis was carried out with *E. coli* DNA microarray as described herein (58). One of the most dramatic changes in RDI 21 deletion mutant was the induction of fim operon expression. The fimAICD-FGH genes in the fim operon were significantly induced 6- to 17-fold in RDI 21 deletion mutant compared to the parent strain RS 218 (58). These findings suggest that RDI 21 deletion mutant might be highly type 1 fimbriated.

Since type 1 fimbriae expression is phase variable, the status of molecular switch fimS in RDI 21 deletion mutant was examined. As expected, the wild type strain RS 218 was composed of a mixture of fimbriated and non-fimbriated cells when grown in BHI broth under static conditions. However, the fimS in RDI 21 deletion mutant was completely in switch-ON orientation under similar growth conditions (58). Growth conditions favorable for ON to OFF switch were examined; but without exception, fimS in RDI 21 deletion mutant was oriented in the switch-ON state under these experimental conditions (58). Type fimbriation using yeast aggregation assays was examined, and found that the ability of RDI 21 deletion mutant to aggregate yeast cells was similar to that of previously constructed fimS-locked-ON mutant of RS 218 (58). These findings indicate that RDI 21 deletion mutant is a fimS-locked-ON mutant and highly type 1 fimbriated.

Whether type 1 fimbriation in RDI 21 deletion mutant is related to its failure to induce a high-degree of bacteremia was explored. To examine the role of type 1 fimbriation in induction of a high-degree of bacteremia, the previously constructed type 1 fimbriation and non-fimbriation mutants of RS 218, fimS-ON and fimS-OFF, respectively, were examined for their ability to induce a high-level of bacteremia in the described infant rat model.

*E. coli* K1 fimS-ON mutant did not induce a high-degree of bacteremia, which was identical to the result obtained with RDI 21 deletion mutant (58). These findings indicate that type 1 fimbriation in RDI 21 deletion mutant is most likely responsible for its failure to induce a high-level of bacteremia in infant rats.

Next, deletion of fim operon from RDI 21 deletion mutant was carried out, and it was found that type 1 fimbria-negative mutant of RDI 21 deletion mutant exhibited an ability to induce a high-degree of bacteremia, similar to that of the parent strain RS 218 (log CFU/ml of blood, mean±SD, 8.15±0.60 compared to 8.59±2.70, respectively). These findings indicate that the failure of RDI 21 deletion mutant to induce a high-degree of bacteremia is due to its high type 1 fimbriation.

Example 6

RDIs Role in Adherence to and Invasion of HBMEC

Six island deletion mutants, RDI 1, 7, 12, 13, 20, and 22 were defective in their abilities to bind and/or invade HBMEC, as shown in Table 9. Compared with those of the wild type *E. coli* RS218, RDI 7, 12, 13, and 20 deletion mutants exhibited HBMEC association rates ranging from 38 to 65%. Similarly, compared with those of the wild type *E. coli* RS218, RDI 1, 7, 12, 13, 20 and 22 deletion mutants exhibited HBMEC invasion rates ranging from 35 to 59%.

RDI 1

RDI 1 deletion mutant exhibited a defect only in HBMEC invasion, suggesting this island contributes to *E. coli* RS218 internalization into HBMEC. RDI 1 is identical to the previously identified island in avian pathogenic *E. coli* BEN2908PAI-I (Genbank access number AY395687). This island contains an IAHP (IcmF associated homologous protein) gene cluster, a widely distributed set of genes among gram-negative bacteria (109-111). Two genes icmF and icmH (dotU) are highly prevalent in the IAHP cluster. Defect in either or both of these genes in *Legionella* resulted in defects in entry and intracellular growth in human macrophages, and avoiding fusion with endosomal compartments (109, 110, 112). However, deletion of these genes in *E. coli* RS218 did not result in HBMEC invasion defect (data not shown).

RDI 12

RDI 12 deletion mutant exhibited a HBMEC association defect without a defect in invasion of HBMEC. RDI 12 is a prophage island unique to *E. coli* RS218, also referred as CUS-3 prophage (113). Most of CDSs in RDI 12 are phage-related, excepting of siaL (encoding an endo-sialidase) and siaO (encoding an O-acetyltransferase) genes. Contributions of sialidase to host cell adherence were demonstrated in *Streptococcus pneumoniae*, where this enzyme desialylated host proteins and exposed host surface for bacterial binding (114, 115). However, deletion of siaL gene in *E. coli* RS218 did not affect its ability to bind to HBMEC (data not shown). The basis for the contribution of RDI 21 to HBMEC association is unclear.

RIM 13 and RDI 20

RDI 13 and 20 deletion mutants exhibited both HBMEC association and invasion defects, suggesting that RDI 13 and 20 contribute to HBMEC adherence and subsequently affect HBMEC invasion. RDI 13 is present in CFT073 genome and homologous to a widely distributed pathogenic island in several subspecies of *Salmonella enterica* (116). RDI 13 is composed of ratA and sivHI operon. SivH protein is an intestinal colonization factor for *Salmonella* (116). sivH was shown to contribute to *Salmonella* colonization of the Peyer's patches in the BALB/c mice. RDI 20 is composed of two transcriptional units, a hip-like operon and fatty acid metabolic genes. The hip-like operon contains two CDSs, organized similarly to the toxin-antitoxin organization in hip operon. It remains to be determined which factors in RDI 13 and RDI 20 are involved in *E. coli* RS218 adherence to HBMEC.

RDI 22

RDI 22 deletion mutant exhibited a defect only in HBMEC invasion, suggesting this island contributes to *E. coli* RS218 invasion into HBMEC. RDI 22 has been sequenced and previously identified as the GimA island (117). The ibeA gene is located in this island. IbeA is a previously identified determinant responsible for RS218 invasion of HBMEC in vitro and traversal of the blood-brain barrier in vivo (118, 119). Thus, HBMEC invasion defect of RDI 22 deletion mutant is likely to be the result of ibeA deletion.

Recently, a comparative genomic hybridization (CGH) was performed on nine representative *E. coli* K1 strains isolated from blood and CSF including strain RS218 using an *E. coli* DNA microarray (120). This DNA microarray was designed based on publicly available genomic sequences, such as *E. coli* K-12 strain MG1655, two O157:H7 strains, uropathogenic strain CFT073, as well as meningitis-causing or uropathogenic *E. coli* specific virulence gene and pathogenicity island sequences from Genbank (121, 122). The distribution of those pathogenic RDIs among those *E. coli* K1 strains is summarized in Table 6. As expected, RDI 16 is present in all of *E. coli* K1 strains because this island harbors the K1 capsule biosynthesis gene cluster. The other pathogenic RDIs are largely existed in phylogenetic group B2. For example, RDI 1, 7, 13, 20, and 22 appear to be widely distributed among this group of *E. coli* K1 strains. Previously studies using PCR, dot blot, and Southern blot suggest that PAI III$_{536}$-like, PAI II$_{196}$-like, and GimA-like ectochromosomal DNA domains (ECDNA) are highly prevalent among 018:K1 strains, the most common serogroup in meningitis-causing *E. coli* worldwide (123). Based on their virulence signatures, those ECDNAs are corresponding to RDI 4, 21, and 22, respectively. The distribution of these three islands among O18:K1 strains based on CGH is consistent with previous findings (124), and is shown in Table 12, below. In Table 12, '−' and '+' indicate absence (defined as less than 40% positive probe hybridization) and presence (defined as greater than 60% positive probe hybridization) of RDIs in the genome, respectively. '±' indicates that the island is partially present in the genome (defined as 40-60% positive probe hybridization). The epidemiological distribution of RDI 12 has recently been evaluated using PCR and this island is also highly prevalent in meningitis-causing *E. coli* O18:K1 strains (37).

Figure 9:
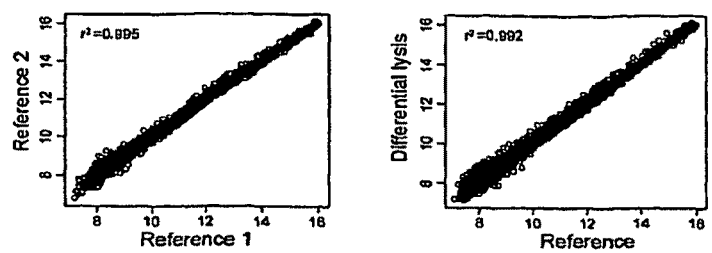
FIG. 9 is a panel of two graphs showing E. coli K1 gene expression pattern during RNA isolation.

One aliquot was immediately extracted (reference sample), while the other was treated with RLT buffer (QIAGEN INC, USA) for 5 minutes to simulate the differential lysis protocol. The reference and the RLT-treated RNA samples were compared using *E. coli* DNA microarray as described previously (114, 115, 117). The expression profile after 5 minute treatment with RLT buffer was nearly identical to that of untreated *E. coli* RS218, as shown in FIG. 9, right panel. FIG. 9 shows that *E. coli* K1 gene expression pattern is preserved during RNA isolation by the differential lysis protocol. No genes were detected whose expression changes were equal to, or greater than, 2-fold or were identified as differentially expressed based on two independent experiments (at cutoff of adjusted p-value≤0.01). Furthermore, the correlation coeffi-

TABLE 12

| | | | Pathogenic RDIs,[a] (no. [%])[b] | | | | | | | | |
|---|---|---|---|---|---|---|---|---|---|---|---|
| Strain | Phylog roup | Serotype | RDI 1 (11 [52]) | RDI 4 (41 [87]) | RDI 7 (6 [50]) | RDI 12[c] (0) | RDI 13 (4 [100]) | RDI 16 (15 [60]) | RDI 20 (9 [90]) | RDI 21 (88 [83]) | RDI 22 (12 [86]) |
| RS218 | B2 | O18:K1 | + | + | + | + | + | + | + | + | + |
| C5 | B2 | O18:K1 | + | + | + | NA | + | + | + | + | + |
| IHE3034 | B2 | O18:K1 | + | + | + | NA | + | + | + | − | + |
| E334 | B2 | O12:K1 | + | ± | ± | NA | + | + | + | ± | + |
| A90 | B2 | O1:K1 | + | ± | + | NA | + | + | + | − | − |
| RS167 | B2 | O16:K1 | + | − | + | − | − | + | + | − | + |
| EC10 | D | O7:K1 | − | − | − | NA | − | + | ± | ± | − |
| RS168 | D | O1:K1 | − | − | − | − | − | + | ± | − | − |
| E253 | A | O12:K1 | − | − | − | NA | − | + | ± | − | − |

In summary a comprehensive analysis of *E. coli* RS218 genome was conducted. 22 *E. coli* RS218-derived genomic islands that are absent in laboratory *E. coli* strain MG1655 were identified. A total of nine islands (i.e. RDI 1, 4, 7, 12, 13, 16, 20, 21, and 22) that are involved in the pathogenic steps of *E. coli* meningitis, such as induction of a high degree of bacteremia and *E. coli* binding to and invasion of HBMEC were found. These results provide a framework for future discovery and analysis of microbial determinants contributing to bacteremia and meningitis caused by *E. coli* K1 strain RS218.

Example 7

Isolation of Bacterial RNA from Infected Blood

An important technical issue in the expression analysis of bacterial pathogens is the extraction of adequate quantities of intact bacterial RNA. The quality and the biological significance of microarray data is entirely dependent upon the structural integrity and the biological quality of the RNA (137). As such, consideration should be given to prevent transcriptional changes associated with preparative procedures of bacterial RNA. For example, before carrying out gene expression analysis using *E. coli* DNA microarray of *E. coli* K1 associated with human brain microvascular endothelial cells (HBMEC), a differential lysis protocol for bacterial RNA isolation was developed and validated (117). In this method, RNA directly extracted from an early log-phase culture of *E. coli* K1 was compared with RNA extracted by the differential lysis protocol from a parallel aliquot of the same culture.

Briefly, *E. coli* K1 strain RS218 in early log phase was prepared by the method described as follows: *E. coli* was grown overnight in a shaker (210 rpm) at 37° C. in BHI broth (BD BIOSCIENCES, San Jose, Calif. USA); the culture was then diluted 10-fold in BHI broth, incubated for 30 additional minutes under the same conditions and split in two aliquots.

cient (r2) between fluorescent intensities from two channels was essentially indistinguishable between a reference-reference self-hybridization (0.995, FIG. 9, left) versus the hybridization between RLT-treated and reference samples (0.992, FIG. 9, right). The DNA microarray analysis demonstrated that the bacterial gene expression profile was not altered during the application of this extraction method. Thus, bacterial RNA isolated using this method is suitable for microarray analysis.

Figure 10:
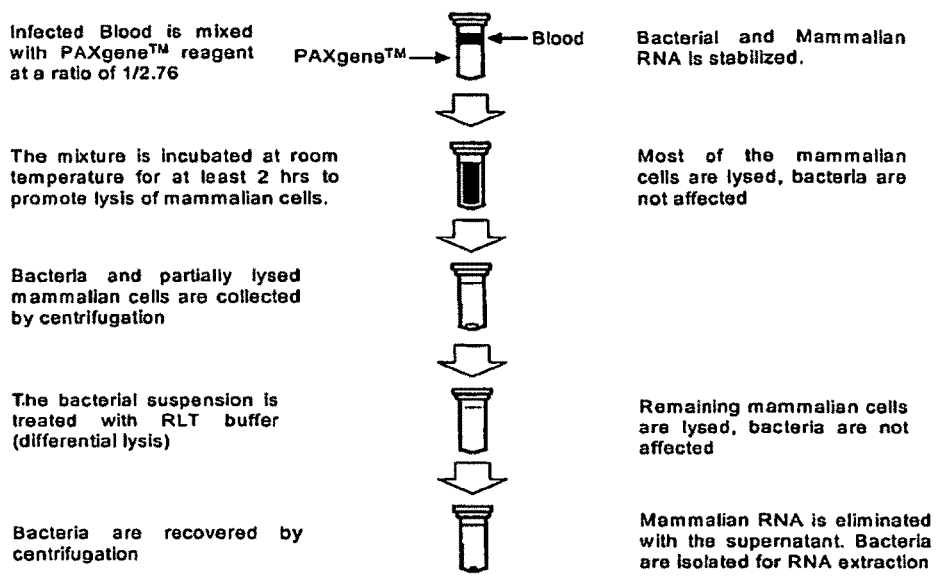
FIG. 10 is a schematic showing the protocol for bacterial RNA isolation from rat blood.

Blood is a complex tissue and its biomass engulfs the infecting bacteria and makes RNA purification difficult and time consuming. Orihuela et al. (143) designed a protocol that uses RNAprotect™ Bacteria reagent (Qiagen Inc., USA) to stabilize bacterial RNA in blood while lysing at the same time the mammalian cells. This protocol was applied to the isolation of *Streptococcus pneumoniae* RNA from infected mice blood (143). The same approach is presented as a schematic as shown in FIG. 10, and was used in the in vivo model of *E. coli* K1 bacteremia. Briefly, 1 ml of adult rat blood containing 1-1.5×10⁸ *E. coli* K1 strain RS218/ml was collected and immediately mixed with RNAprotect™ Bacteria (Qiagen Inc., USA) at a ratio of 35:1 (vol/vol; RNAprotect/blood) by vortexing for 5 seconds. The mixture was centrifuged at 825×g for 10 min to remove debris and at 15,000×g for 15 min to pellet the bacteria. RNA was then extracted using the RIBOPURE-Bacteria Kit (Ambion, Foster City, Calif., USA). RIBOPURE-Bacteria Kit includes zirconia-silica beads for bead beating with a special vortex adapter (Ambion). The use of bead beating was necessary as efficient lysis of *E. coli* RS218 required mechanical disruption of the cell wall.

Figure 11:
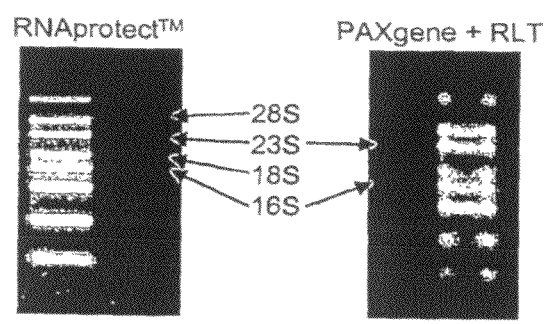
FIG. 11 is two panels of agarose gel electrophoresis gels.

Bacterial RNA extracted by this protocol was heavily contaminated with mammalian RNA (FIG. 11). This may be due to the fact that RNAPROTECT BACTERIA is a reagent for RNA stabilization only and has not been designed to obtain a complete and efficient lysis of mammalian cells. Moreover, the mammalian RNA was partially degraded, seen by a low 28S/18S ratio. Intact mammalian RNA can be eliminated from a bacterial RNA preparation using hybridization capture (MICROBENRICH; Ambion, Foster City, Calif., USA) by means of specific oligonucleotides that bind to mammalian ribosomal and polyadenylated RNAs. Unfortunately, degraded RNA might lack the necessary homologous regions and may not be removed by hybridization capture. This degraded mammalian RNA could interfere with the subsequent microarray experiment by competing with bacterial RNA during cDNA synthesis and labeling, impeding a correct quantification of the starting amount of bacterial RNA and limit the total amount of RNA to be used for probe generation.

Besides being of poor quality, the sample collected contained a very low amount of bacteria RNA, which is consistent with the observation of Orihuela et al. (143) where high titers of bacteria (>108 CFU/ml) in body fluids are required to obtain good RNA yields. Alternative methods can be used for isolating the bacterial RNA from an in vivo model and a novel method based on using PAXGENE Blood RNA Tubes (PreAnalytix, Hombrechtikon, CH). PAXGENE Blood RNA Tubes contain a proprietary blend of reagents based on a patented RNA stabilization technology. Component from this blend protect RNA molecules from degradation by RNases and prevent induction of gene expression in blood cells. The PAXGENE reagent had not been previously tested for bacteria. The first step was, therefore, to use E. coli DNA microarray to verify if the PAXGENE reagent could be used to stabilize RNA in E. coli K1. A 0.5 ml aliquot from an overnight 37° C. static culture of E. coli RS218 in BHI broth was centrifuged at 1500×g for 5 minutes, resuspended in 5 ml of fetal bovine serum (Omega Scientific) and incubated for 30 additional minutes. The culture was then split in two aliquots of 2.5 ml each. One aliquot was immediately extracted for use as the reference sample using RIBOPURE-Bacteria Kit while the other was processed as for an infected blood sample using PAXGENE Blood RNA Tube, as shown in FIG. 10. The tube was incubated at room temperature for 2 hours according to the instructions provided by PreAnalytix. In a real application of the PAXGENE system to blood, the erythrocytes, which represent the more abundant cellular fraction in blood, would be lysed during this incubation. Bacteria were recovered by centrifugation, resuspended in RLT buffer (Qiagen Inc.) and vortexed for 30 seconds. This step was added to eliminate the remaining mammalian cells and did not affect E. coli K1. Bacteria were recovered again by centrifugation and RNA was extracted using RiboPure™-Bacteria Kit.

RNA obtained with this technique was analyzed using the Agilent bioanalyzer. The 23S/16S rRNA ratio was 1.8, indicating that no degradation of the bacterial RNA had occurred. To verify that the RNA sample was not biased during the preparative procedure, the reference RNA sample and RNA sample extracted using this blood protocol were compared using the E. coli DNA microarray. The expression profile of the bacterial sample extracted using the blood protocol was nearly identical to that of the reference sample. No genes were detected whose expression changes were equal to or greater than 2-fold or were identified as differentially expressed based on two independent experiments (at cutoff of adjusted p-value≤0.01). Based on these findings, PAXGENE reagent was effective in stabilizing E. coli K1 RNA and the protocol appears to be suitable for extracting E. coli K1 strain RS 218 total RNA from infected rat blood without biasing the gene expression profile.

This protocol for bacterial RNA extraction from infected blood was applied in an in vivo model of E. coli bacteremia. E. coli K1 strain RS218 was injected subcutaneously to 5-day-old pathogen-free Sprague-Dawley rats as previously described (87, 88, 96, 99, 107, 108, 125). Briefly, an E. coli RS218 overnight 37° C. static culture in BHI broth was diluted 10-fold in BHI broth and incubated for 3 additional hours under the same conditions. Bacteria were centrifuged at 1500×g for 5 minutes and resuspended in PBS (pH=7.4, Invitrogen) to OD620=0.2 (108 CPU/ml). Aliquots containing 106 CFU were prepared and injected subcutaneously to 3 pups. Blood was collected 18 hours post-injection when the animals had developed the maximum non-lethal level of bacteremia. Approximately 100 ml of whole blood containing approximately $10^7$ E. coli CFU was collected from each animal. The 3 blood specimens were pulled together and extracted using the PAXGENE-based blood protocol as described above. The quality of the RNA sample was assessed by agarose gel electrophoresis (FIG. 11) and using the Agilent 2100 bioanalyzer. The molecular weight and the relative amount of the different species of rRNA indicated that the sample was free of host RNA contamination. Moreover the 23S/16S rRNA ratio was 1.79, indicating little or no degradation of the bacterial RNA. A sample prepared as described above yielded approximately 2 mg of RNA as determined by measuring the absorbance at 260 and 280 nm (A260/A280=2.1). Thus, the sample obtained with this blood protocol based on PAXGENE Blood RNA Tube is suitable for microarray analysis.

The experiments reported herein were carried out using the following materials and methods.

Bacterial Strains

E. coli RS218$^{str}$ is a spontaneous streptomycin-resistant mutant of E. coli RS218 (O18:K1:H7), isolated from the cerebrospinal fluid of a neonate with E. coli meningitis (14). E. coli E44 is a spontaneous rifampin-resistant mutant of E. coli RS218. E. coli K-12 strain HB101 is a laboratory strain and used as a negative control for in vitro infection experiments.

Strains S88 and S95 were obtained from E. Bingen (49) and 11E3034 from T K. Korhonen (50). The remaining E. coli strains were described previously (51, 52). Bacteria were grown overnight at 37.0 in Luria Broth. A summary of various E. coli K1 strains that are contemplated for use with any of the methods of the invention presented herein are shown below in Table 13:

TABLE 13

| Strain | Serotype | Virulence[a] | Origin | Reference |
|---|---|---|---|---|
| RS218 | O18:K1:H7 | virulent | N. America | (32, 40, 64) |
| C5 | O18:K1:H7 | virulent | N. America | (41) |
| IHE3034 | O18:K1:H7 | virulent | Finland | (49) |
| EC10 | O7:K1 | virulent | N. America | (42) |
| A90 | O1:K1:H7 | virulent | Finland | (42) |
| RS167 | O16:K1:H6 | virulent | N. America | (42) |
| RS168 | O1:K1:H- | virulent | N. America | (42) |
| S88 | O45:K1 | virulent | France | (7) |
| S95 | O45:K1 | virulent | France | (7) |
| E253 | O12:K1 | virulent | N. America | (13) |
| E334 | O12:K1 | virulent | N. America | (13) |

[a]based on their ability to cause bacteremia and meningitis in 5-day-old rats.

Identification of E. coli RS218-Derived Islands

The presence and boundaries of gram negative bacterial islands can be determined using sequence alignment. For example, E. coli RS218-derived islands were determined with sequence alignment between published E. coli MG1655 genome and the draft sequence of E. coli RS218. Using this method, one of skill in the art can use the published E. coli MG1655 genome to determine RDIs or homologues to RDIs from other bacterial strains using simple sequence alignment.

For practical reasons, the minimal island length cutoff was set as 10 kilobases, which subsequently generated 22 E. coli RS218-derived sequence segments. These 22 E. coli RS218-derived islands were termed as RDIs. Prediction of coding sequences (CDSs) inside each island was conducted with a prokaryotic gene finder, EasyGene (15). Combining query results from InterPro and Genbank, each predicted CDS was assigned to the putative functions.

Construction of E. coli RS218 Island Deletion Mutants

RDI deletion mutants can be constructed using a method termed the "scarless" deletion method, which is described in the art (16). Using this method to construct any deletion mutant, deletion alleles are constructed with PCR and cloned into a suicide vector carrying antibiotic resistance gene and the recognition site of meganuclease I-SceI. This suicide plasmid is then integrated into any bacterial genome. In preferred embodiments, the bacterial genome is a gram-negative bacterial genome. Gram-negative bacteria have been described herein. In further embodiments the bacteria is chosen from a bacteria from Table 13. Integration occurs by homologous recombination between the mutant and wild-type alleles. Subsequently, meganuclease I-SceI gene from helper plasmid is induced to stimulate the resolution of this chromosomal cointegrate by introducing a unique double-strand break into the chromosome. This resolution via intramolecular recombination of the allele pair resulted in either a mutant or a wild type chromosome, which is distinguished by allele-specific PCR screening. Both deletions are then confirmed by PCR with screening primers and sequencing of PCR products.

As an example of this method, but not to limit the invention, RDI 21 and 22 deletion mutants were constructed using "scarless" deletion method (16). Briefly, deletion alleles were constructed with PCR and cloned into a suicide vector carrying antibiotic resistance gene and the recognition site of meganuclease I-SceI. This suicide plasmid was then integrated into E. coli RS218 genome by homologous recombination between the mutant and wild-type alleles. Subsequently, meganuclease I-SceI gene from helper plasmid was induced to stimulate the resolution of this chromosomal cointegrate by introducing a unique double-strand break into the chromosome. This resolution via intramolecular recombination of the allele pair resulted in either a mutant or a wild type chromosome, which was distinguished by allele-specific PCR screening. Both deletions were confirmed by PCR with screening primers and sequencing of PCR products.

Since the "scarless" deletion method is relatively time-consuming and labor-intensive, other RDIs were deleted, except of RDI 9, 10, 15 using a simpler "one-step PCR" approach (17). Briefly, each RDI was replaced with a chloramphenicol cassette that was PCR-synthesized with long primers based on the antibiotic-resistance gene in template plasmid. Both primers had 50-nt extensions that were homologous to boundaries of the targeting island. After electroporation into E. coli RS218, the island was replaced with chloramphenicol cassette via homologous recombination, which was facilitated by λ Red system (18). Subsequently, chloramphenicol was used to identify mutants and confirmation of correct island replacement was conducted as described above.

RDI 9, 10 and 15 could not be deleted from E. coli RS218 using the above described methods. Subsequently, RDI 9, 10 and 15 deletion mutants were constructed using an adapted P1 transduction-mediated DNA fragment replacement approach (19). Briefly, each RDI corresponding fragment in E. coli MG1655 was replaced with kanamycin resistance cassette using the "one-step PCR" gene inactivation method as described above (17). The P1 bacteriophage transducing lysates of the constructed E. coli MG1655 mutants were made with P1 bacteriophage growth on each K-12 mutant in soft agar and used to infect E. coli E44 wild type. After infection, kanamycin was used to screen E. coli E44 mutants. The resulting RDI deletion mutants were confirmed with loss of specific marker genes inside corresponding islands and integration of K-12 flanking DNA fragments in E. coli E44.

DNA Isolation, Labeling and Hybridization.

E. coli strains were grown overnight in brain heart infusion broth (53) at 3TC with shaking. 1.S ml of overnight culture was centrifuged for S min at 4'C at high speed in a table-top centrifuge (Eppendorf, Westbur, N.Y.). Supernatants were discarded, and cell pellets were resuspended in an equal volume of TE buffer (10 mM Tris, 1 mM EDTA; pH 8.0). Briefly, genomic DNA was isolated and labeled as described previously with a modification (54, 55). Genomic DNA was digested completely with EcoRV (New England Biolabs, Beverly, Mass.) and purified by using the QIAquick PCR purification kit (QIAGEN, Valencia, Calif.). Digested DNA (2 µg) was mixed with 4 µg random hemmer (Invitrogen, Carlsbad, Calif.) and S µl NEB buffer 2 (New England Biolabs, Beverly, Mass.) in a total volume of 44 then denatured at 95'C for 10 min and followed by snap cooling on ice. 5 µl of dNTP mixture (5 mM dATP, 5 mM dCTP, 5 mM dGTP, 1 mM dTTP, 4 mM aa-dUTP) and 1 µl Klenow enzyme (New England Biolabs) were added and the labeling was carried out for 12 h at 37° C. The products were purified by using the QIAquick PCR purification kit (QIAGEN), eluted in 10 µl water and dissolved with either Cy3 or CyS mono-functional NHS ester (Amersham Biosciences, Piscataway, N.J.) in 2 µl DMSO. 2 µl dye solution and 1 µl labeling buffer (1M sodium bicarbonate, pH 9.3) were added to the purfied aminemodified DNA. The mixture was incubated in the dark at room temperature for 1 hour. The labels were purified by using the QIAquick PCR purification kit (QIAGEN). The purified Cy3- and CyS-coupled labels were combined and concentrated by centrifugation in a spin filter (Nanosep, molecular weight cutoff, 30,000; PaIl, An Arbor, Mich.). The concentrated DNA was resuspended in SO µl hybridization buffer (Pronto! Universal 10 hybridization kit; Corning, N.Y.). The hybridization mixture was then denatured at 95"C for 2 min. The mixture was applied onto the array under a LifterSlip cover slip (Erie Scientific, Portsmouth, N.H.). The assembled slide was placed in a hybridization chamber (Coming, Park Acton, Mass.) and incubated at 42'C for 16 to 18 h. Following hybridization, slides were extensively washed for 1 min in 2×SSC (1×SSC is 0.15 M NaCl plus 0.015 M sodium citrate), 0.1% SDS at 42'C; 5 min in 2×SSC, 0.1% SDS at 42'C; 10 min in 1×SSC at room temperature; and 2 min in 0.1×SSC at room temperature twice. Each experiment was run as a competitive hybridization by using Cy3-labeled DNA from one of the 10 strains and Cy-5-labeled DNA from strain RS218. Then, experiments were repeated by reversing dyes.

Array Scanning and Analysis

Arrays were scanned by using GenePix 4000B micro array scanner (Axon Instruments, Fremont, Calif.) with 100% scan power and PMT voltage set for each array to minimize saturated pixels and approximately equalize signal intensities in the two channels. Image processing and data extraction were performed by using GenePix Pro 6.0 (Axon Instruments). Spots were excluded from analysis because of high local background fluorescence and slide abnormalities. To equalize the two channels, the median of intensity of each channel on each slide were normalized to 1000). To determine cut-off value for "present" versus "absent" or "divergent", ORFs with intensity less than negative control value (median value of 95 negative control oligonucleotides) are considered as "absent" and ORFs with intensity greater than 1000 (validated by PCR) are considered as "present". If both channels can not be determined by above criteria, these ORFs were considered as "divergent". For remaining ORFs, if channel A showed "absent" and the ratio of intensities (B/A) is less than 3.0, these ORFs in channel B are also considered as "absent", otherwise "divergent", if channel A showed "present" and the ratio of intensities (BI A) is less than 0.3, these ORFs in channel B were considered as "absent", otherwise "present".
Hierarchical Clustering Data imported from GenePix was manipulated and clustered, using established algorithms implemented in the software program Cluster (56). Average linkage clustering with centered correlation was used. TreeView software generated visual representations of clusters (57).

PCR Confirmation of Micro Array Data

Table 14 (Forward primers disclosed as SEQ ID NOS 4-11, respectively, in order of appearance and reverse primers disclosed as SEQ ID NOS 12-19, respectively, in order of appearance)

TABLE 14

| Genes | Sequence | |
|---|---|---|
| | Forward | Reverse |
| cnf1 | ggactcgaggtggtggtcta | cgttgatggctcaggaaaat |
| aslA | gcgtgatgttcatgtcaacc | atccgccagatctacaatgc |
| fyuA | ggctataccaccgctgaaac | acccggttaccgtgatacaa |
| hlyA | cttaggaaaggcaggcagtg | acttatcggcaatggacagg |
| hlyE | cccgcagcaatagaatagga | ccgcagatggagcattagat |
| ibeA | agaaacggcaaaatcaatgg | actcggtgaccgtactccag |
| iha | tgcaggctgacagaatcatc | ccggctatgagaaaaagctg |
| iucA | accactctctcccggcttat | gtagagggaacgggaagagg |

Triplex PCR for Phylogenetic Grouping

The above 11 representative strains of E. coli K1 were also examined for E. coli phylogenetic group by using a combination of two genes (chuA and yjaA) and an anonymous DNA fragment (TspE4C2). PCR was carried out as described previously (58).

Tissue Cultures and In Vitro Infection Experiments

Both primary and immortalized human brain microvascular endothelial cells (HBMEC) were cultured and used for bacterial association and invasion assays as described previously (20, 21). Briefly, for association assays, confluent HBMEC in 24-well tissue culture plates (Corning Costar, Corning, N.Y.) were incubated with $10^7$ E. coli at a multiplicity of infection of 100 for 90 minutes at 37° C. Monolayers were washed three times with PBS and lysed with sterile water for 30 minutes at room temperature. The released bacteria were enumerated by plating on sheep blood agar plates. Results were calculated as a percent of the initial inoculums and expressed as percent relative association rate compared to percent association rate of strain RS218" or E44. The association rates of RS218$^{str}$ or E44 ranged between 14.3% and 22.0% and E. coli K-12 strain HB101 consistently showed <0.1% association.

For invasion assays, HBMEC monolayers were incubated with $10^7$ E. coli for 90 minutes as described above. Monolayers were washed once and then incubated with experimental medium containing gentamicin (100 µg/ml) for 1 hour to kill extracellular bacteria. The monolayers were washed with PBS for three times, lysed with sterile water, and the released internalized bacteria were enumerated as described above. Results were expressed as percent relative invasion rate compared to percent invasion rate of strain RS218$^{str}$ or E44. The invasion rates of RS218" or E44 ranged between 0.1 and 0.6% and E. coli K-12 strain HB101 showed <0.01% invasion.

Animal Model of E. coli Bacteremia E. coli bacteremia were induced in 5-day-old rats by subcutaneous injection of E. coli as previously described (94-96, 99, 107, 108). Briefly, the bred, pathogen-free pregnant Sprague-Dawley rats with timed conception were purchased from Charles Rivers Breeding Laboratories (Wilmington, Mass.). At 5 days of age, all members of each litter were randomly divided into designated experimental groups to receive subcutaneously $10^6$ CFU of E. coli RS218", or E44, or its deletion mutants. At 18 hours after bacterial inoculation, blood specimens were obtained for quantitative cultures as previously described (99). Bacterial counts in the blood of 5-day old rats infected with either E. coli RS218$^{str}$ or E44 were found to be similar and the data was combined. These animal experiments were approved by the Johns Hopkins University Animal Care and Use Committee and carried out in accordance with institutional guidelines.

Microarray Descriptions

A total of 8144 50-mers oligonucleotides from E. coli and 95 negative control from human and Arabidopsis thaliana were spotted in replicate onto ami co silane slides. The oligonucleotides that are targeting backbone genes in E. coli genomes were derived from a commercially designed oligonucleotide set, which covers every ORF present in E. coli strain MG1655, and enterohaemorrhagic E. coli (EHEC) 0157:H7 strains EDL933 and Sakai (altogether 6268 50-mers). The ExPEC-specific (extraintestinal pathogenic E. coli) oligonucleotide probes were derived from uropathogenic E. coli strain CFT073 and meningitis-causing E. coli strains (RS218 and C5) sequences that were different from and/or absent in E. coli backbone (1876 50-mers). In principle, oligonucleotides from the commercial source were constructed in accumulative fashions, i.e., oligonucleotides targeting every ORF present in MG1655 were constructed and 0157:H7 specific probes were added subsequently. Similarly, ExPEC-specific 50-mer oligonucleotide probes were designed and constructed to adapt existing oligonucleotides set to the usages in meningitis causing or uropathogenic E. coli. The majority of conserved backbone ORFs or E. coli strain-specific ORFs were targeted with single probes. ORFs that were shared among different E. coli but appeared to be hyper-variable were usually targeted with two or more oligonucleotide probes.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the instant invention and the following claims.

REFERENCES

The following specific documents, also incorporated herein by reference, are indicated in the above discussion and examples by a number in parentheses corresponding the below numerical listing.
1. Glode M P, Sutton A, Robbins J B, et al. Neonatal meningitis due of *Escherichia coli* K1. J Infect Dis 1977; 136 Suppl:S93-7
2. Glode M P, Sutton A, Moxon E R and Robbins J B. Pathogenesis of neonatal *Escherichia coli* meningitis: induction of bacteremia and meningitis in infant rats fed *E. coli* K1. Infect Immun 1977; 16:75-80
3. Kim K S. Pathogenesis of bacterial meningitis: from bacteraemia to neuronal injury. Nat Rev Neurosci 2003; 4:376-85
4. Dietzman D E, Fischer G W and Schoenknecht F D. Neonatal *Escherichia coli* septicemia-bacterial counts in blood. J Pediatr 1974; 85:128-30
5. Kim K S. *Escherichia coli* translocation at the blood-brain barrier. Infect Immun 2001; 69:5217-22
6. Pfister H W, Fontana A, Tauber M G, Tomasz A and Scheid W M. Mechanisms of brain injury in bacterial meningitis: workshop summary. Clin Infect Dis 1994; 19:463-79
7. Scheid W M, Koedel U, Nathan B and Pfister H W. Pathophysiology of bacterial meningitis: mechanism(s) of neuronal injury. J Infect Dis 2002; 186 Suppl 2:S225-33
8. Dobrindt U, Hochhut B, Hentschel U and Hacker J. Genomic islands in pathogenic and environmental microorganisms. Nat Rev Microbiol 2004; 2:414-424
9. Hentschel U, Hacker J. Pathogenicity islands: the tip of the iceberg. Microbes Infect 2001; 3:545-8
10. Hacker J, Camiel E. Ecological fitness, genomic islands and bacterial pathogenicity. A Darwinian view of the evolution of microbes. EMBO Rep 2001; 2:376-81
11. Welch R A, Burland V, Plunkett G, 3rd, et al. Extensive mosaic structure revealed by the complete genome sequence of uropathogenic *Escherichia coli*. Proc Natl Acad Sci USA 2002; 99:17020-4
12. Blattner F R, Plunkett G, 3rd, Bloch C A, et al. The complete genome sequence of *Escherichia coli* K-12. Science 1997; 277:1453-74
13. Rode C K, Melkerson-Watson L J Johnson A T and Bloch C A. Type-specific contributions to chromosome size differences in *Escherichia coli*. Infect Immun 1999; 67:230-6
14. Silver R P, Aaronson W, Sutton A and Schneerson R. Comparative analysis of plasmids and some metabolic characteristics of *Escherichia coli* K1 from diseased and healthy individuals. Infect. Immun. 1980; 29:200-206
15. Larsen T S, Krogh A. EasyGene—a prokaryotic gene finder that ranks ORFs by statistical significance. BMC Bioinformatics 2003; 4:21
16. Kolisnychenko V, Plunkett G, 3rd, Herring C D, et al. Engineering a reduced *Escherichia coli* genome. Genome Res 2002; 12:640-7
17. Datsenko K A, Wanner B L. One-step inactivation of chromosomal genes in *Escherichia coli* K-12 using PCR products. Proc Natl Acad Sci USA 2000; 97:6640-5
18. Murphy K C. Use of bacteriophage lambda recombination functions to promote gene replacement in *Escherichia coli*. J Bacteriol 1998; 180:2063-71
19. Bloch C A, Thome G M and Ausubel F M. General method for site-directed mutagenesis in *Escherichia coli* O18ac:K1:H7: deletion of the inducible superoxide dismutase gene, sodA, does not diminish bacteremia in neonatal rats. Infect Immun 1989; 57:2141-8
20. Stins M, Prasadarao N, Ibric L, Wass C, Luckett P and Kim K. Binding characteristics of S fimbriated *Escherichia coli* to isolated brain microvascular endothelial cells. Am J Pathol 1994; 145:1228-1236
21. Prasadarao N, Wass C, Weiser J, Stins M, Huang S and Kim K. Outer membrane protein A of *Escherichia coli* contributes to invasion of brain microvascular endothelial cells. Infect. Immun. 1996; 64:146-153
22. Kim K S, Itabashi H, Gemski P, Sadoff J, Warren R L and Cross A S. The K1 capsule is the critical determinant in the development of *Escherichia coli* meningitis in the rat. 3 Clin Invest 1992; 90:897-905
23. Schmidt H, Hensel M. Pathogenicity islands in bacterial pathogenesis. Clin Microbiol Rev 2004; 17:14-56
24. Gonzalez M D, Lichtensteiger C A., Caughlan R and Vimr E R. Conserved filamentous prophage in *Escherichia coli* 018:K1:H7 and *Yersinia pestis* biovar orientalis. J Bacteriol 2002; 184:6050-5
25. Dobrindt U, Blum-Oehler G, Hartsch T, et al. S-Fimbria-encoding determinant sfa(I) is located on pathogenicity island III (536) of uropathogenic *Escherichia coli* strain 536. Infect Immun 2001; 69:4248-56
26. Negre V L, Bonacorsi S, Schubert S, Bidet P, Nassif X and Bingen E. The siderophore receptor IroN, but not the high-pathogenicity island or the hemin receptor ChuA, contributes to the bacteremic step of *Escherichia coli* neonatal meningitis. Infect Immun 2004; 72:1216-20
27. Baumler A J, Norris T L, Lasco T, et al. IroN, a novel outer membrane siderophore receptor characteristic of *Salmonella enterica*. J Bacteriol 1998; 180:1446-53
28. Hantke K, Nicholson G, Rabsch W and Winkelmann G. Salmochelins, siderophores of *Salmonella enterica* and uropathogenic *Escherichia coli* strains, are recognized by the outer membrane receptor IroN. Proc Natl Acad Sci USA 2003; 100:3677-82
29. Bister B, Bischoff D, Nicholson G J, et al. The structure of salmochelins: C-glucosylated enterobactins of *Salmonella enterica*. Biometals 2004; 17:471-81
30. Vermeulen C, Cross A, Byrne W R and Zollinger W. Quantitative relationship between capsular content and killing of K1-encapsulated *Escherichia coli*. Infect Immun 1988; 56:2723-30
31. Dobrindt U, Blum-Oehler G, Nagy G, et al. Genetic structure and distribution of four pathogenicity islands (PAI I(536) to PAI IV(536)) of uropathogenic *Escherichia coli* strain 536. Infect Immun 2002; 70:6365-72
32. Houdouin V, Bonacorsi S, Brahimi N, Clermont O, Nassif X and Bingen E. A Uropathogenicity Island Contributes to the Pathogenicity of *Escherichia coli* Strains That Cause Neonatal Meningitis. Infect. Immun. 2002; 70:5865-5869
33. VanRheenen S M, Dumenil G and Isberg R R. IcmF and DotU are required for optimal effector translocation and trafficking of the *Legionella pneumophila* vacuole. Infect Immun 2004; 72:5972-82
34. Sexton J A, Miller J L, Yoneda A, Kehl-Fie T E and Vogel J P. *Legionella pneumophila* DotU and IcmF are required for stability of the Dot/Icm complex. Infect Immun 2004; 72:5983-92
35. Das S, Chaudhuri K. Identification of a unique IAHP (IcmF associated homologous proteins) cluster in *Vibrio cholerae* and other proteobacteria through in silico analysis. In Silico Biol 2003; 3:287-300
36. Zusman T, Feldman M, Halperin E and Segal G. Characterization of the icmH and icmF genes required for *Legionella pneumophila* intracellular growth, genes that are present in many bacteria associated with eukaryotic cells. Infect Immun 2004; 72:3398-409
37. Deszo E L, Steenbergen S M, Freedberg D I and Vimr E R. *Escherichia coli* K1 polysialic acid O-acetyltransferase gene, neuO, and the mechanism of capsule form variation involving a mobile contingency locus. Proc Natl Mad Sci USA 2005; 102:5564-9
38. Tong H H, Liu X, Chen Y, James M and Demaria T. Effect of neuraminidase on receptor-mediated adherence of *Streptococcus pneumoniae* to chinchilla tracheal epithelium. Acta Otolaryngol 2002; 122:413-9
39. Tong H H, Blue L E, James M A and DeMaria T F. Evaluation of the Virulence of a *Streptococcus pneumoniae* Neuraminidase-Deficient Mutant in Nasopharyngeal Colonization and Development of Otitis Media in the Chinchilla Model. Infect. Immun. 2000; 68:921-924
40. Kingsley R A, Humphries A D, Weening E H, et al. Molecular and phenotypic analysis of the C S54 island of *Salmonella enterica* serotype typhimurium: identification of intestinal colonization and persistence determinants. Infect Immun 2003; 71:629-40
41. Huang S H, Chen Y H, Kong G, et al. A novel genetic island of meningitic *Escherichia coli* K1 containing the ibeA invasion gene (GimA): functional annotation and carbon-source— regulated invasion of human brain microvascular endothelial cells. Funct Integr Genomics 2001; 1:312-22
42. Huang S H, Wan Z S, Chen Y H, Jong A Y and Kim K S. Further characterization of *Escherichia coli* brain microvascular endothelial cell invasion gene ibeA by deletion, complementation, and protein expression. J Infect Dis 2001; 183:1071-8
43. Prasadarao N V, Wass C A, Huang S H and Kim K S. Identification and characterization of a novel Ibe10 binding protein that contributes to *Escherichia coli* invasion of brain microvascular endothelial cells. Infect Immun 1999; 67:1131-8
44. Yao Y, Xie Y and Kim K S. Genomic comparison of *E. coli* K1 strains isolated from the cerebrospinal fluid of patients with meningitis. Infection and Immunity 2006; in press
45. Teng C H, Cai M, Shin S, et al. *Escherichia coli* K1 RS218 interacts with human brain microvascular endothelial cells via type 1 fimbria bacteria in the fimbriated state. Infect Immun 2005; 73:2923-31
46. Di Cello F, Xie Y, Paul-Satyaseela M and Kim K S. Approaches to Bacterial RNA Isolation and Purification for Microarray Analysis of *Escherichia coli* K1 Interaction with Human Brain Microvascular Endothelial Cells. J. Clin. Microbiol. 2005; 43:4197-4199
47. Bonacorsi S, Clermont O, Houdouin V, et al. Molecular analysis and experimental virulence of French and North American *Escherichia coli* neonatal meningitis isolates: identification of a new virulent clone. J Infect Dis 2003; 187:1895-906
48. Benjamini Y, Hochberg Y. Controlling the false discovery rate: a practical and powerful approach to multiple testing. J. Roy. Statist. Soc. Ser. 1995; B 57:289-300
49. Bonacorsi, S., O. Clermont, V. Houdouin, C. Cordevant, N. Brahimi, A. Marecat, C. Tinsley, X. Nassif, M. Lange, and E. Bingen. 2003. Molecular analysis and experimental virulence of French and North American *Escherichia coli* neonatal meningitis isolates: identification of a new virulent clone. J Infect D is 187:1895-906.
50. Meier, C., T. A. Oelschlaeger, H. Merkert, T. K. Korhonen, and J. Hacker. 1996. Ability of *Escherichia coli* isolates that cause meningitis in newborns to invade epithelial and endothelial cells. Infect Imun 64:2391-9.
51. Cross, A. S., K. S. Kim, D. C. Wright, J. C. Sadoff, and P. Gemski. 1986. Role oflipopolysaccharde and capsule in the sero resistance of bacteremic strains of *Escherichia coli*. J Infect Dis 154:497-503.
52. Kim, K. S., Jane H. Kang and Alan S. Cross. 1986. The role of capsular antigens in seru resistance and in vivo virulence of *Escherichia coli*. FEMS Microbiology Letters 35:275-278.
53. Teng, C. H., M. Cai, S. Shin, Y. Xie, K. J. Kim, N. A. Khan, F. Di Cello, and K. S. Kim. 2005. *Escherichia coli* K1 RS218 interacts with human brain microvascular endothelial cells via type i fimbria bacteria in the fimbriated state. Infect Imun 73:2923-31.
54. Frederick M. Ausubel, R. B., Robert E. Kingston. 1992. 1992. Short protocols in molecular biology.
55. Robbins, J. B., G. H. McCracken, Jr., E. C. Gotschlich, F. Orskov, I. Orskov, and L. A. Hanson. 1974. *Escherichia coli* K1 capsular polysaccharide associated with neonatal meningitis. N Engl J Med 290:1216-20.
56. Eisen, M. B., P. T. Spellman, P. O. Brown, and D. Botstein. 1998. Cluster analysis and display of genome-wide expression patterns. Proc Natl Acad Sci USA 95:14863-8.
57. Rippere-Lampe, K. E., A. D. O'Brien, R. Conran, and H. A. Lockman. 2001. Mutation of the gene encoding cytotoxic necrotizing factor type 1 (cnf1) attenuates the virulence ofuropathogenic *Escherichia coli*. Infect Imun 69:3954-64.
58. Clermont, O., S. Bonacorsi, and E. Bingen. 2000. Rapid and simple determination of the *Escherichia coli* phylogenetic group. Appl Environ Microbiol 66:4555-8.
59. Bonacorsi, S., O. Clermont, V. Houdouin, C. Cordevant, N. Brahimi, A. Marecat, C. Tinsley, X. Nassif, M. Lange, and E. Bingen. 2003. Molecular analysis and experimental virulence of French and North American *Escherichia coli* neonatal meningitis isolates: identification of a new virulent clone. J Infect D is 187:1895-906.
60. James R. Johnson and Thomas A. Russo. 2002. Uropathogenic *Escherichia coli* as Agents of Diverse Non-Urinary Tract Extraintestinal Infection. J Infect Dis. 186: 859-864.
61. Salama, N., K. Guilemin, T. K. McDaniel, G. Sherlock, L. Tompkins, and S. Falkow. 2000. A whole-genome micro array reveals genetic diversity among *Helicobacter pylori* strains. Proc Natl Acad Sci USA 97: 14668-73.
62. Eisen, M. B., P. T. Spellman, P. O. Brown, and D. Botstein. 1998. Cluster analysis and display of genome-wide expression patterns. Proc Natl Acad Sci USA 95:14863-8.
63. Robbins, J. B., G. H. McCracken, Jr., E. C. Gotschlich, F. Orskov, I. Orskov, and L. A. Hanson. 1974. *Escherichia coli* K1 capsular polysaccharide associated with neonatal meningitis. N Engl J Med 290:1216-20.
64. Huang, S. H., Z. S. Wan, Y. H. Chen, A. Y. Jong, and K. S. Kim. 2001. Further characterization of *Escherichia coli* brain microvascular endothelial cell invasion gene ibeA by deletion, complementation, and protein expression. J Infect D is 183:1071-8.
65. Boquet, P. 2001. The cytotoxic necrotizing factor 1 (CNF1) from *Escherichia coli*. Toxicon 39:1673-80.
66. Rippere-Lampe, K. E., A. D. O'Brien, R. Conran, and H. A. Lockman. 2001. Mutation of the gene encoding cytotoxic necrotizing factor type 1 (cnf1) attenuates the virulence ofuropathogenic *Escherichia coli*. Infect Imun 69:3954-64.
67. Nemani P V, Huang S H, Wass C A and Kim K S. Identification and characterization of a novel Ibe10 binding protein contributing to *E. coli* invasion of brain microvascular endothelial cells. Infect Immun 67:1131-1138, 1999.

68. Di Cello F, Xie Y, Paul-Satyaseela M and Kim K S. Approaches to bacterial RNA isolation and purification for microarray analysis of *Escherichia coli* K1 interaction with human brain microvascular endothelial cells. J. Clin. Micro. 43:4197-4199, 2005.
69. Kim K S, Cross A S, Zollinger W and Sadoff J: Prevention and therapy of experimental *E. coli* infection with monoclonal antibody. Infect Immun 50:734-737, 1985.
70. Cross A S, Kim K S, Wright D C, Sadoff J C and Gemski P: Role of lipopolysaccharide and capsule in the serum-resistance of bacteremic strains of *E. coli*. J Infect Dis 154:497-503, 1986.
71. Nemani P V, Huang S H, Wass C A and Kim K S. Identification and characterization of a novel Ibe10 binding protein contributing to *E. coli* invasion of brain microvascular endothelial cells. Infect Immun 67:1131-1138, 1999.
72. Teng C H, Cai M, Shin S, Xie Y, Kim K J, Khan N A, Di Cello F and Kim K S. *Escherichia coli* K1 RS218 interacts with human brain microvascular endothelial cells via type 1 fimbria phase-on bacteria. Infect Immun 73:2923-2931, 2005.
73. Yao Y, Xie Y and Kim K S. Genomic comparison of *E. coli* strains isolated from the cerebrospinal fluid of patients with meningitis. Infect Immun 74:2196-2206, 2006.
74. Teng C H, Xie Y, Shin S, Di Cello F, Maneesh P, Cai M and Kim K S. Effects of ompA deletion on *Escherichia coli* K1 strain RS218's type 1 fimbria expression and association with human brain microvascular endothelial cells. Infect Immun 74:5609-5616, 2006
75. Xie Y, Kolisnychenko V, Paul-Satyassela M, Elliot S, Parthasarathy G, Yao Y, Plunkett G, Blottner F R and Kim K S. Identification and characterization of *E. coli* RS 218-derived islands in the pathogenesis of *E. coli* meningitis. J Infect Dis 194:358-364, 2006.
76. Xie Y, Yao Y, Kolisnychenko V, Teng C, Kim K S. HbiF regulates type 1 fimbriation independent of FimB and FimE. Infect Immun 74:4039-4047, 2006.
77. Teng C H, Xie Y, Shin S, Di Cello F, Maneesh P, Cai M and Kim K S. Effects of ompA deletion on *Escherichia coli* K1 strain RS218's type 1 fimbria expression and association with human brain microvascular endothelial cells. Infect Immun 74:5609-5616, 2006
78. Wisplinghoff H, Bischoff T, Tallent S M, Seifert H, Wenzel R P, Edmond M B. Nosocomial bloodstream infections in US hospitals: analysis of 24,179 cases from a prospective nationwide surveillance study. Clin Infect Dis 39:309-17, 2004.
79. Biedenbach D J, Moet G J, Jones R N. Occurrence and antimicrobial resistance pattern comparisons among bloodstream infection isolates from the SENTRY Antimicrobial Surveillance Program (1997-2002). Diagn Microbiol Infect Dis 50:59-69, 2004.
80. Stoll B J, Hansen N, Fanaroff A A, Wright L L, Carlo M A, Ehrenkranz R A, Lemons J A, Donovan E F, Atrak A R, Tyson J E, Oh W, Bauer C R, Korones S B, Shankaran S, Laptook A R, Stevenson D K, Papile L, Poole W K. Changes in pathogens causing early-onset sepsis in very-low-birth-weight infants. N Engl J Med 347:240-247, 2002
81. Sannes M R, Kuskowski M A, Owens K, Gajewski A, Johnson J R. Virulence factor profiles and Phylogenetic background of *Escherichia coli* isolates from veterans with bacteremia and uninfected Control subjects. J Infect Dis 190:2121-2128, 2004
82. Khayr W F, CarMichael M J, Dubanpwoch C, Latif R, Waiters L. Bacteremia in veterans administration nursing home patients. Amer J Therapeu 11:251-257, 2004
83. Baine W B, Yu W, Summe J P. The epidemiology of hospitalization of elderly Americans for septicemia Or bacteremia in 1991-1998: application of medicare claims data. Ann Epidemiol 11:118-126, 2001
84. Jackson L A, Benson P, Neuzil K M, Grandjean M, Marino I L. Burden of community-onset *Escherichia coli* bacteremia in seniors. J Infect Dis 191:1523-1529, 2005
85. Russo T A, Johnson J R. Medical and economical impact of extraintestinal infections due to *Escherichia Coli*: focus on an increasingly important endemic problem. Microbes Infect 5:449-456, 2003
86. Berkley J A, Lowe B S, Mwangi I, Williams T, Bauni E, Mwarumba S, et al. Bacteremia among children admitted to a rural hospital in Kenya. N Eng J of Med 352:39-47, 2005.
87. Cross A S, Kim K S, Wright D C, Sadoff J C, Gemski P. Role of lipopolysaccharide and capsule in the serum-resistance of bacteremic strains of *E. coli*. J Infect Dis 154:497-503, 1986.
88. Kim K S, Kang J H, Cross A S. The role of capsular antigens in serum resistance and in vivo virulence of *Escherichia coli*. FEMS Microbiol Lett 35:275-278, 1986.
89. Soderstrom T, Hansson G, Larson G. The *Escherichia coli* K1 capsule shares antigenic determinants with the human ganglioside GM3 and GD3. N Eng J Med 15:726-7, 1984.
90. Finne J, Bitter-Suermann D, Goridis C, Finne U. An IgG monoclonal antibody to group B meningococci cross-reacts with developmentally regulated polysialic acid units of glycoproteins in neural and extraneural tissues. J Immunol 138:4402-7, 1987.
91. Cross A, Artenstein A, Que J, Fredeking T, Furer E, Sadoff J C, Cryz S J Jr. Safety and immunogenicity of a polyvalent *Escherichia coli* vaccine in human volunteers. J Infect Dis 170:834-40, 1994.
92. Rode C K, Melkerson-Watson L J, Johnson A T, Bloch C A. Type-specific contributions to chromosome size differences in *Escherichia coli*. Infect Immun 67:230-236, 1999.
93. Bonacorsi S P P, Clermont O, Tinsley C, Le Gall I, Beaudoin J-C, Elion J, Nassif X, and Bingen E. Identification of regions of the *Escherichia coli* chromosome specific for neonatal meningitis-associated strains. Infect Immun 68:2096-2101, 2000.
94. Cross A S, Kim K S, Wright D C, Sadoff J C, Gemski P. Role of lipopolysaccharide and capsule in the serum-resistance of bacteremic strains of *E. coli*. J Infect Dis 154:497-503, 1986.
95. Kim K S, Kang J H, Cross A S. The role of capsular antigens in serum resistance and in vivo virulence of *Escherichia coli*. FEMS Microbiol Lett 35:275-278, 1986.
96. Kim K S, Itabashi H, Gemslci P, Sadoff J, Warren R L, Cross A S. The K1 capsule is the critical determinant in the development of *Escherichia coli* meningitis in the rat. J Clin Invest 90:897-905, 1992.
97. Stins M, Prasadarao N, Ibric L, Wass C, Luckett P, Kim K. Binding characteristics of S fimbriated *Escherichia coli* to isolated brain microvascular endothelial cells. Am J Pathol 145:1228-1236.
98. Prasadarao N V, Wass C A, Kim K S. Identification and characterization of S fimbria-binding sialoglycoproteins on brain microvascular endothelial cells. Infect Immun 65:2852-2860, 1997.
99. Wang Y, Wen Z G, Kim K S. Role of S fimbriae in *E. coli* K1 binding to brain microvascular endothelial cells in vitro and penetration into the central nervous system in vivo Microb Pathogenesis 37:287-293, 2004.
100. Negre V L, Bonacorsi S, Schubert S, Bidet P, Nassif X, Bingen E. The siderophore receptor IroN, but not the high-pathogenicity island or the hemin receptor ChuA, contributes to the bacteremic step of Escherichia coli neonatal meningitis. Infect Immun 72:1216-1220, 2004.

100a. Thompson J M, Jones H A, Perry R D. Molecular characterization of the hemin uptake locus (hmu) from *Yersinia pestis* and analysis of hmu mutants for heroin and hemoprotein utilization. Infect Immun 67:3879-3892, 1999.

101. Nienaber A, Hennecke H, Fischer H M. Discovery of a haem uptake system in the soil bacterium *Bradyrhizobium japonicum*. Mol Microbiol 41:787-800, 2001.

102. Klemm P, Hjerrild L, Gjermansen M, Schembri M A. Structure-function analysis of the self-recognizing Antigen 43 autotransporter protein from *Escherichia coli*. Mol Microbiol 51:283-296, 2004.

103. Benz I and Schmidt M A. Cloning and expression of an adhesin (AIDA-I) involved in diffuse adherence of enteropathogenic *Escherichia coli*. Infect Immun 57:1506-1511, 1989.

104. Gonzalez M D, Lichtensteiger C A, Caughlan R, Vimr E R. Conserved filamentous prophage in *Escherichia coli* O18:K1:H7 and *Yersinia pestis* biovar orientalis. J Bacteriol 184:6050-6055, 2002.

105. Gonzalez M D, Lichtensteiger C A, Vimr E R. Adaptation of signature-tagged mutagenesis to *Escherichia coli* K1 and the infant-rat model of invasive disease. FEMS Microbiol Lett 198:125-128, 2001.

106. Houdouin V, Bonacorsi S, Brahimi N, Clermont O, Nassif X, Bingen E. A uropathogenicity island contributes to the pathogenicity of *Escherichia coli* strains that cause neonatal meningitis. Infect Immun 70:5865-5869, 2002.

107. Kim K S, Kang H I, Cross A S, Kaufman B, Zollinger W, Sadoff J. Functional activities of monoclonal antibodies to O-side chain of *Escherichia coli* lipopolysaccharides in vitro and in vivo. J Infect Dis 157:47-53, 1988.

108. Schiff D E, Wass C A, Cryz S J, Cross A S, Kim K S. Estimation of protective levels of anti-0 specific lipopolysaccharide IgG antibody against experimental K1 *Escherichia coli* infection. Infect Immun 61:975-980, 1993.

109. Larsen T S, Krogh A. Easy-Gene-a prokaryotic gene finder that ranks ORFs by statistical significance. Bioinformatics 4:21, 2003.

110. Posfai G, Kolisnychenko V, Bereczki Z, Blattner F R. Markerless gene replacement in *Escherichia coli* stimulated by a double-strand break in the chromosome. Nucleic Acids Res 27:4409-4415, 1999.

111. Kolisnychenko V, Plunkett G, 3rd, Herring C D, Feher T, Posfai J, Blattner F R, Posfai G. Engineering a reduced *Escherichia coli* genome. Genome Res 12:647, 2002.

112. Datsenko K A, Wanner B L. One-step inactivation of chromosomal genes in *Escherichia coli* K-12 using PCR products. Proc Natl Acad Sci USA 97:6640-6645, 2000.

113. Kim K J, Elliott S A, DiCello F, Stins M F, Kim K S. The K1 capsule modulates trafficking of *E. coli*-containing vacuoles and enhances intracellular bacterial survival in human brain microvascular endothelial cells. Cell Microbial 5:245-252, 2003.

114. Teng C H, Cai M, Shin S, Xie Y, Kim K J, Khan N A, Di Cello F, Kim K S. *Escherichia coli* K1 RS218 interacts with human brain microvascular endothelial cells via type 1 fimbria phase-on bacteria. Infect Immun 73:2923-2931, 2005.

115. Yao Y, Xie Y and Kim K S. Genomic comparison of *E. coli* strains isolated from the cerebrospinal fluid of patients with meningitis. Infect Immun 74:2196-2206, 2006.

116. Dobrindt U, Hochhut B, Hentschel U, Hacker J. Genomic islands in pathogenic and environmental microorganisms. Nat Rev Microbiol 2:414-424, 2004.

117. Di Cello F, Xie Y, Paul-Satyaseela M, Kim K S. Approaches to bacterial RNA isolation and purification for microarray analysis of *Escherichia coli* K1 interaction with human brain microvascular endothelial cells. J. Clin. Micro. 43:4197-4199, 2005.

118. Badger J B, Wass C A, Kim K S. Identification of *E. coli* K1 genes contributing to human brain microvascular endothelia cell invasion by differential fluorescence induction. Mol Micro 36:174-182, 2000.

119. Badger J, Wass C. Weissman S, Kim K S. Application of signature-tagged mutagenesis for the identification of *E. coli* K1 genes that contribute to invasion of the blood-brain barrier. Infect Immun 68:5056-5061, 2000.

120. Hoffman J A, Badger J L, Zhang Y, Huang S H, Kim K S. *E. coli* K1' aslA contributed to invasion of brain microvascular endothelial cells in vitro and in vivo. Infect Immun 68:5062-5067, 2000.

121. Huang S H, Wan Z S, Chen Y H, Jong A Y, Kim K S. Further characterization of *Escherichia coli* brain endothelial cell invasion gene ibeA by deletion, complementation and protein expression. J Infect Dis 183:1071-1078, 2001.

122. Nemani P V, Huang S H, Wass C A, Kim K S. Identification and characterization of a novel Ibe10 binding protein contributing to *E. coli* invasion of brain microvascular endothelial cells. Infect Immun 67:1131-1138, 1999.

123. Nemani P V, Wass C A, Kim K S. Endothelial cell GlcNAcB1-4 GlcNAc epitopes for outer membrane protein A traversal of *E. coli* across the blood-brain barrier. Infect Immun 64:154-160, 1996.

124. Huang S H, Wass C A, Fu Q, Nemani P V, Stins M and Kim K S: *E. coli* invasion of brain microvascular endothelial cells in vitro and in vivo: Molecular cloning and characterization of *E. coli* invasion gene ibe10. Infect Immun 63:4470-4475, 1995.

125. Kim K S, Cross A S, Zollinger W and Sadoff J: Prevention and therapy of experimental *E. coli* infection with monoclonal antibody. Infect Immun 50:734-737, 1985.

126. Kim K S, Cross A S, Kaufman B, Zollinger W and Sadoff J: Murine hybridoma antibodies enhance bactericidal activity of human cord blood against K1 *E. coli* strains. Pediatr Res 28:667-670, 1990.

127. Reed L J, Meunch H. A simple method of estimating fifty percent endpoints. Amer J Hygiene 27:493-497, 1938

128. Khan N A, Shin S, Chung J W, Kim K J, Elliot S, Wang Y and Kim K S. Outer membrane protein A and cytotoxic necrotizing factor-1 use diverse signaling mechanisms for *Escherichia coli* K1 invasion of human brain microvascular endothelial cells. Micro Pathogenesis 35:35-42, 2003.

129. Cohen J. Statistical power analysis for the behavioral sciences. 2nd Edition, Hillsdale, N.J., 179-213, 1988.

130. Krcmery V, Spanik S, Mrazova M, Trupl J, Grausova S, gery E, Kukuckova E, Sulcova M, Krupova I, Koren P. Bacteremias caused by *Escherichia coli* in cancer patients-analysis of 65 episodes. Int J Infect Dis 6:69-73, 2002

131. Velasco E, Byington R, Martins C S, Schmirmer M, Dias L C, Conclaves V M. Bloodstream infectionSurveillance in a cancer center a prospective look at clinical microbiology aspects. Clin Microbiol Infect 10:542-549, 2004

132. Khan N A, Kim Y, Shin S and Kim K S. FimH-mediated *Escherichia coli* K1 invasion of human brain microvascular endothelial cells. Cell Microbiol 9:169-178, 2007

133. Parthasarathy G, Yao Y and Kim K S. Flagella promote *Escherichia coli* K1 association with and invasion of human brain microvascular endothelial cells. Infect Immun (in press)

134. Xie Y, Yao Y, Kolisnychenko V, Teng C, Kim K S. HbiF regulates type 1 fimbriation independent of FimB and FimE. Infect Immun 74:4039-4047, 2006

135. Xie Y, Kolisnychenko V, Paul-Satyassela M, Elliot S, Parthasarathy G, Yad Y, Plunkett G, Blottner F R and Kim K S. Identification and characterization of *E. coli* RS 218-derived islands in the pathogenesis of *E. coli* meningitis. J Infect Dis 194:358-364, 2006.

136. Fasano A, Baudry B, Pumplin D W, Wasserman S S, Tall B D, Ketley J M, Kaper J B. *Vibrio cholerae* produces a second enterotoxin, which affects intestinal tight junctions, Proc Natl Acad Sci USA 88:5242-5246, 1991.

137. Mangan, J. A., Monahan, I. M., and Butcher, P. D., Gene expression during host-pathogen interactions: approaches to bacterial mRNA extraction and labeling for microarray analysis, in Functional Microbial Genomics, B. W. Wren and N. Dorrel, Editors. Academic press: London. p. 137-51, 2002

138. Eriksson, S., Lucchini, S., Thompson, A., Rhen, M., and Hinton, J. C., Unravelling the biology of macrophage infection by gene expression profiling of intracellular *Salmonella enterica*. Mol Micro 47:103-18, 2003.

139. Dietrich, G., Kurz, S., Hubner, C., Aepinus, C., Theiss, S., Guckenberger, M., Panner, U., Weber, 3., and Frosch, M., Transcriptome analysis of *Neisseria meningitidis* during infection. J Bacteriol 18: 155-64, 2003.

140. Staudinger, B. J., Oberdoerster, M. A., Lewis, P. J., and Rosen, H., mRNA expression profiles for *Escherichia coli* ingested by normal and phagocyte oxidase-deficient human neutrophils. J Clin Invest 110: 1151-63, 2002.

141. Voyich, J. M., Sturdevant, D. E., Braughton, K. R., Kobayashi, S. D., Lei, B., Virtaneva, K., Dorward, D. W., Musser, J. M., and DeLeo, F. R., Genome-wide protective response used by group A *Streptococcus* to evade destruction by human polymorphonuclear leukocytes. Proc Natl Acad Sci USA 100: 1996-2001, 2003.

142. Grifantini, R., Bartolini, E., Muzzi, A., Draghi, M., Frigimelica, E., Berger, J., Ratti, G., Petracca, R., Galli, G., Agnusdei, M., Giuliani, M. M., Santini, L., Brunelli, B., Tettelin, H., Rappuoli, R., Ranrlazzo, F., and Grandi, G., Previously unrecognized vaccine candidates against group B meningococcus identified by DNA microarrays. Nat Biotechnol 20: 914-21, 2002.

143. Orihuela, C. J., Raclin, J. N., Sublett, J. E., Gao, G., Kaushal, D., and Tuomanen, E. I., Microarray analysis of pneumococcal gene expression during invasive disease. Infect Immun 72: 5582-96, 2004.

144. Hinton, J. C., Hautefort, I., Eriksson, S., Thompson, A., and Rhen, M., Benefits and pitfalls of using microarrays to monitor bacterial gene expression during infection. Curr Opin Microbiol 7: 277-282, 2004.

145. Schnappinger, D., Ehrt, S., Voskuil, M. I., Liu, Y., Mangan, J. A., Monahan, I. M., Dolganov, G., Efron, B., Butcher, P. D., Nathan, C., and Schoolnik, G. K., Transcriptional Adaptation of *Mycobacterium tuberculosis* within Macrophages: Insights into the Phagosomal Environment. J Exp Med 198: 693-704, 2003

146. Bernstein, J. A., Khodursky, A. B., Lin, P. H., Lin-Chao, S., and Cohen, S. N., Global analysis of mRNAdecay and abundance in *Escherichia coli* at single-gene resolution using two-color fluorescent DNA microarrays. Proc Natl Acad Sci USA 99:9697-702, 2002.

147. Selinger, D. W., Saxena, R. M., Cheung, K. J., Church, G. M., and Rosenow, C., Global RNA half-life analysis in *Escherichia coli* reveals positional patterns of transcript degradation. Genome Res 13: 216-23, 2003.

148. Mohanty, B. K. and Kushner, S. R., Analysis of the function of *Escherichia coli* poly(A) polymerase I in RNA metabolism. Mol Micro 34:1094-108, 1999.

149. Sherlock O, Schembri M A, Reisner A, Klemm P. Novel roles for the AIDA adhesin from diarrheagenic *E. coli*: cell aggregation and biafilm formation. J Bacteriol 186:8058-8065, 2004

150. Henderson I R, Navarro-Garcia F, Desvaux M, Fernandez R C, AlaAldeen D. Type V protein secretion pathway: the autotransporter story. Micro Mol Biol Rev 68:692-744, 2004

151. Mckenzie G J, Craig N L. Fast, easy and efficient site-specific insertion of transgenes into enterobacterial chromosomes using Tn7 without need for selection of the insertion event. BMC Microbiol 6:39, 2006

152. Prasadarao N V, Wass C A, Hacker J, Jann K, Kim K S. Adhesion of S-fimbriated *Escherichia coli* to brain glycolipids mediated by sfaA gene-encoded protein of S-Fimbriae. Biol Chem 268:10363-10363, 1993.

153. Rubinsztein-Dunlop S, Guy B, Lissolo L, Fischer H. Identification of two new *Helicobacter pylori* surface proteins involved in attachment to epithelial cell lines. J Med Microbiol 54:427-434, 2005.

154. Kolberg J, Aase A, Bergmann S, Herstad T, Rodal G, Frank R, Rohde M, Hammerschmidt S. *Streptococcus pneumoniae* enolase is important for plasminogen bidnging despite low abundance of enolase protein on the bacterial cell surface. Microbiology 152:1307-1317, 2006

155. Nemani P V, Wass C, Stins M F, Weiser J, Huang S H and Kim K S: Outer membrane protein A of *E. coli* contributes to invasion of brain microvascular endothelial cells. Infect Immun 64:146-153, 1996.

156. Shin S, Lu G, Cai M and Kim K S. *Escherichia coli* outer membrane protein A adheres to human brain microvascular endothelial cells. Biochem. Biophys. Res. Commun. 330: 1199-1204, 2005.

157. Kim K S, Cross A S and Sadoff J: Monoclonal antibody to the O-side chain of *Escherichia coli* lipopolysaccharides enhances the efficacy of cefotaxime against experimental K1 *Escherichia coli* infection caused by a homologous 0 serotype. Serodiagnosis Immunotherapy In Infect Dis 4: 95-99. 1990

158. Kim K S: Comparison of cefotaxime, imipenem-cilastatin, ampicillin-gentamicin and ampicillin-chloramphenicol in the treatment of experimental *E. coli* bacteremia and meningitis. Antimicrobial Agents Chemother 28:433-436, 1985.

159. Teng C H, Xie Y, Shin S, Di Cello F, Maneesh P, Cai M and Kim K S. Effects of ompA deletion on *Escherichia coli* K1 strain RS218's type 1 fimbria expression and association with human brain microvascular endothelial cells. Infect Immun 74:5609-5616, 2006

160. Pfaffl M W, Horgan G W, Dempfle L. Relative expression software tool (REST) for group-wise comparison and statistical analysis of relative expression results in real-time PCR. Nucleic Acids Res 30:e36, 2002

161. Durant L, Metals A, Soulama-Mouze C, Genevard 3, Nassif X, Escaich S. Identification of candidates for a subunit vaccine against extraintestinal pathogenic *Escherichia coli*. Infect Immun 75:1916-1925, 2007.

What is claimed is:

1. A method for immunizing a subject against a bacterial infection, the method comprising administering to the subject one or more isolated polypeptides or an isolated mRNA or synthetic nucleic acid encoding the one or more polypeptides, wherein the one or more polypeptides are encoded by one or more *Escherichia coli* (*E. coli*)-derived island (RDI) sequences selected from the group consisting of RDI 1, RDI 4, RDI 7, RDI 12, RDI 13, RDI 16, RDI 20, RDI 21 and RDI 22, thereby immunizing the subject against the bacterial infection.

2. The method of claim 1, wherein the bacterial infection is an *E. coli* infection.

3. The method of claim 2, wherein the *E. coli* infection is an extraintestinal *E. coli* infection.

4. The method of claim 3, wherein the extraintestinal *E. coli* infection is selected from the group consisting of: bacteremia, sepsis, meningitis, urinary tract infection and pneumonia.

5. The method of claim 1, wherein the method stabilizes, reduces the symptoms of, or ameliorates a disease or disorder characterized by the bacterial infection.

6. The method of claim 1, wherein the RDI sequence is derived from an *E. coli* strain selected from the group consisting of RS 218, C5, IHE3034, RS167, A90, S88 and S95.

7. A method of modulating an immune response in a subject in need thereof, the method comprising administering to the subject the one or more isolated polypeptides or the isolated mRNA or synthetic nucleic acid encoding the one or more polypeptides of claim 1, thereby modulating the immune response in the subject.

* * * * *

SEQUENCE LISTING

<160> NUMBER OF SEQ ID NOS: 19

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgaaacgac atctgaacac cag                                         23

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atatggccgg cccggagcct gccagaatcc g                                31

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggactcgagg tggtggtcta                                             20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcgtgatgtt catgtcaacc                                             20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
ggctatacca ccgctgaaac                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cttaggaaag gcaggcagtg                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cccgcagcaa tagaatagga                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agaaacggca aaatcaatgg                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgcaggctga cagaatcatc                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
accactctct cccggcttat                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cgttgatggc tcaggaaaat                                              20
```

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atccgccaga tctacaatgc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acccggttac cgtgatacaa                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
acttatcggc aatggacagg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccgcagatgg agcattagat                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
actcggtgac cgtactccag                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccggctatga gaaaaagctg                                              20
```

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtagagggaa cgggaagagg                                                    20
```